US012708252B2

(12) United States Patent
Tilson et al.

(10) Patent No.: US 12,708,252 B2
(45) Date of Patent: Aug. 18, 2026

(54) ENDOSCOPE SHEATH APPARATUSES

(71) Applicant: NEPTUNE MEDICAL INC., Burlingame, CA (US)

(72) Inventors: Alexander Q. Tilson, Burlingame, CA (US); Thomas Hsiu, Palo Alto, CA (US); Niklas J. Helmick, San Jose, CA (US); Stephan T. Hoffmann, Danville, CA (US); Eugene Duval, Menlo Park, CA (US); Christopher J. Hasser, Lotus, CA (US); James M. Hayes, La Honda, CA (US); Elias Eleftheriades, Redwood City, CA (US); Kai Pohlhammer, San Ramon, CA (US)

(73) Assignee: Neptune Medical Inc., Burlingame, CA (US)

( * ) Notice: Subject to any disclaimer, the term of this patent is extended or adjusted under 35 U.S.C. 154(b) by 0 days.

(21) Appl. No.: 18/325,974

(22) Filed: May 30, 2023

(65) Prior Publication Data

US 2023/0346204 A1 Nov. 2, 2023

Related U.S. Application Data

(63) Continuation of application No. PCT/US2023/066293, filed on Apr. 27, 2023.

(Continued)

(51) Int. Cl.

*A61B 1/00* (2006.01)
*A61B 1/012* (2006.01)
*A61B 90/00* (2016.01)

(52) U.S. Cl.

CPC ...... *A61B 1/00142* (2013.01); *A61B 1/00055* (2013.01); *A61B 1/00057* (2013.01);

(Continued)

(58) Field of Classification Search

CPC .......... A61B 1/000142; A61B 1/00137; A61B 1/018; A61B 1/00135; A61B 1/0008;

(Continued)

(56) References Cited

U.S. PATENT DOCUMENTS

| | | | |
|---|---|---|---|
| 2,268,321 | A | 12/1941 | Flynn |
| 2,767,705 | A | 10/1956 | Moore |

(Continued)

FOREIGN PATENT DOCUMENTS

| | | | |
|---|---|---|---|
| AU | 2013207571 | B2 | 8/2013 |
| CN | 2613655 | Y | 4/2004 |

(Continued)

OTHER PUBLICATIONS

Dow, Dow white paper: Can you estimate moduius from durometer hardness for silicones: Yes, but you only roughly and you must choose your modulus carefully!; 5 pages; retrieved from the internet (https://www.dow.com/content/dam/doc/documents/en-us/tech-art/11/11-37/11-3716-01-durometer-hardness-for-silicones.pdf) on Jan. 18, 2023.

(Continued)

*Primary Examiner* — Michael J Carey
*Assistant Examiner* — Megan Elizabeth Monahan
(74) *Attorney, Agent, or Firm* — Shay Glenn LLP

(57) ABSTRACT

Sheaths that may be used with endoscopes, and in particular, robotic endoscopes and/or telescoping endoscopes, as well as method of using these sheaths to prevent cross-contamination between patients and contamination of the endoscope are described. These sheaths include both an outer sheath for covering the outside of the endoscope and one or more inner sheaths for covering a lumen of the endoscope, and are configured so as not to interfere with the flexibility or operation of the endoscope. These sheaths may reduce or eliminate the need for endoscope cleaning.

24 Claims, 51 Drawing Sheets

Related U.S. Application Data

(60) Provisional application No. 63/335,720, filed on Apr. 27, 2022.

(52) U.S. Cl.
CPC ...... *A61B 1/00128* (2013.01); *A61B 1/00137* (2013.01); *A61B 1/012* (2013.01); *A61B 2090/064* (2016.02); *A61B 2090/081* (2016.02)

(58) Field of Classification Search
CPC . A61B 1/00119; A61B 1/00103; A61B 1/005; A61B 2017/00296
See application file for complete search history.

(56) References Cited

U.S. PATENT DOCUMENTS 3,459,229 A 8/1969 Croft
3,466,220 A 9/1969 Allinikov et al.
3,859,986 A 1/1975 Okada et al.
3,998,216 A 12/1976 Hosono
4,066,071 A 1/1978 Nagel
4,141,364 A 2/1979 Schultze
4,151,800 A 5/1979 Dotts et al.
4,160,451 A 7/1979 Chittenden
4,176,662 A 12/1979 Frazer
4,425,919 A 1/1984 Alston, Jr.
4,551,140 A 11/1985 Shinohara
4,690,131 A 9/1987 Lyddy, Jr. et al.
4,696,544 A 9/1987 Costella
4,717,379 A 1/1988 Ekholmer
4,741,326 A * 5/1988 Sidall ................ A61B 1/00142 600/125
4,794,412 A 12/1988 Casey et al.
4,794,912 A 1/1989 Lia
4,815,450 A 3/1989 Patel
4,817,613 A 4/1989 Jaraczewski et al.
4,890,602 A 1/1990 Hake
4,893,613 A 1/1990 Hake
4,913,369 A 4/1990 Lia et al.
4,959,058 A 9/1990 Michelson
4,961,738 A 10/1990 Mackin
4,967,732 A 11/1990 Inoue
4,997,084 A 3/1991 Opie et al.
5,018,436 A 5/1991 Evangelista et al.
5,019,121 A 5/1991 Krauter
5,037,386 A 8/1991 Marcus et al.
5,037,404 A 8/1991 Gold et al.
5,050,585 A * 9/1991 Takahashi ................ A61B 1/12 600/459
5,105,819 A 4/1992 Wollschlager et al.
5,123,421 A 6/1992 Sinofsky
5,125,143 A 6/1992 Takahashi
5,174,276 A 12/1992 Crockard
5,183,471 A 2/1993 Wilk
5,188,595 A 2/1993 Jacobi
5,193,525 A 3/1993 Silverstein et al.
5,201,908 A 4/1993 Jones
5,251,611 A 10/1993 Zehel et al.
5,337,733 A 8/1994 Bauerfeind et al.
5,342,299 A 8/1994 Snoke et al.
5,360,440 A 11/1994 Andersen
5,419,310 A 5/1995 Frassica et al.
5,447,148 A 9/1995 Oneda et al.
5,496,292 A 3/1996 Burnham
5,531,685 A 7/1996 Hemmer et al.
5,531,719 A 7/1996 Takahashi
5,547,455 A 8/1996 McKenna et al.
5,549,542 A 8/1996 Kovalcheck
5,577,992 A 11/1996 Chiba et al.
5,591,137 A 1/1997 Stevens
5,601,588 A 2/1997 Tonomura et al.
5,603,991 A 2/1997 Kupiecki et al.
5,607,435 A 3/1997 Sachdeva et al.
5,624,381 A 4/1997 Kieturakis
5,632,734 A 5/1997 Galel et al.
5,637,075 A 6/1997 Kikawada
5,662,587 A 9/1997 Grundfest et al.
5,662,621 A 9/1997 Lafontaine
5,746,692 A 5/1998 Bacich et al.
5,749,828 A 5/1998 Solomon et al.
5,759,151 A 6/1998 Sturges
5,779,624 A 7/1998 Chang
5,782,811 A 7/1998 Samson et al.
5,823,961 A 10/1998 Fields et al.
5,876,329 A 3/1999 Harhen
5,882,347 A 3/1999 Mouris Laan et al.
5,891,112 A 4/1999 Samson
5,906,591 A 5/1999 Dario et al.
5,916,145 A * 6/1999 Chu .................. A61B 1/00154 600/124
5,916,147 A 6/1999 Boury
5,951,539 A 9/1999 Nita et al.
5,961,526 A 10/1999 Chu et al.
5,976,074 A 11/1999 Moriyama
6,090,099 A 7/2000 Samson et al.
6,159,187 A 12/2000 Park et al.
6,162,171 A 12/2000 Ng et al.
6,165,123 A 12/2000 Thompson
6,179,776 B1 1/2001 Adams et al.
6,190,357 B1 2/2001 Ferrari et al.
6,203,493 B1 3/2001 Ben-Hain
6,217,565 B1 4/2001 Cohen
6,217,566 B1 4/2001 Ju et al.
6,276,661 B1 8/2001 Laird
6,296,644 B1 10/2001 Surat et al.
6,309,346 B1 10/2001 Farhadi
6,352,503 B1 3/2002 Matsu et al.
6,364,878 B1 4/2002 Hall
6,368,315 B1 4/2002 Gillis et al.
6,408,682 B2 6/2002 Greszler
6,468,203 B2 10/2002 Belson
6,485,409 B1 11/2002 Voloshin et al.
6,503,225 B1 1/2003 Kirsch et al.
6,517,477 B1 2/2003 Wendlandt
6,547,724 B1 4/2003 Soble et al.
6,572,538 B2 6/2003 Takase
6,572,590 B1 6/2003 Stevens et al.
6,579,277 B1 6/2003 Rabiner et al.
6,610,007 B2 8/2003 Belson et al.
6,612,982 B1 9/2003 Ouchi
6,616,628 B2 9/2003 Hayzelden
6,620,126 B2 9/2003 Unsworth et al.
6,623,424 B2 9/2003 Hayakawa et al.
6,712,832 B2 3/2004 Shah
6,726,677 B1 4/2004 Flaherty et al.
6,730,020 B2 5/2004 Peng et al.
6,780,151 B2 8/2004 Grabover et al.
6,783,491 B2 8/2004 Saadat et al.
6,790,173 B2 9/2004 Saadat et al.
6,793,621 B2 9/2004 Butler et al.
6,793,661 B2 9/2004 Hamilton et al.
6,800,056 B2 10/2004 Tartaglia et al.
6,869,393 B2 3/2005 Butler
6,899,673 B2 5/2005 Ogura et al.
6,908,428 B2 6/2005 Aizenfeld et al.
6,911,004 B2 6/2005 Kim et al.
6,923,754 B2 8/2005 Lubock
6,960,162 B2 11/2005 Saadat et al.
6,974,411 B2 12/2005 Belson
6,984,203 B2 1/2006 Tartaglia et al.
7,056,283 B2 6/2006 Baror et al.
7,060,199 B2 6/2006 Woydt et al.
7,172,552 B2 2/2007 Wendlandt
7,214,230 B2 5/2007 Brock et al.
7,273,469 B1 9/2007 Chan et al.
7,288,101 B2 10/2007 Deem et al.
7,291,127 B2 11/2007 Eidenschink
7,354,427 B2 * 4/2008 Fangrow ............... A61J 1/2082 604/416
7,365,509 B2 4/2008 Park et al.
7,438,712 B2 10/2008 Chouinard
7,511,733 B2 3/2009 Takizawa et al.
7,537,562 B2 5/2009 Takano

(56) References Cited

U.S. PATENT DOCUMENTS 7,559,916 B2 7/2009 Smith et al.
7,591,782 B2 9/2009 Fujikura
7,598,652 B2 10/2009 Kornbluh et al.
7,658,738 B2 2/2010 Nobis et al.
7,695,428 B2 4/2010 Machida
7,736,323 B2 6/2010 Von Weymarn-Scharli
7,749,196 B2 7/2010 Osborne et al.
7,837,615 B2 11/2010 Le et al.
7,850,725 B2 12/2010 Vardi et al.
7,901,347 B2 3/2011 Sekiguchi et al.
7,909,755 B2 3/2011 Itoi
7,918,819 B2 4/2011 Karmarkar et al.
7,918,845 B2 4/2011 Saadat et al.
7,931,661 B2 4/2011 Saadat et al.
7,935,047 B2 5/2011 Yoshida et al.
7,947,000 B2 5/2011 Vargas et al.
7,957,790 B2 6/2011 Kleen
7,970,455 B2 6/2011 Zilberstein et al.
7,988,621 B2 8/2011 Smith et al.
8,047,236 B2 11/2011 Perry
8,075,476 B2 12/2011 Vargas
8,092,374 B2 1/2012 Smith et al.
8,109,953 B1 2/2012 King, III et al.
8,123,739 B2 2/2012 McQueen et al.
8,125,755 B2 2/2012 Garcia et al.
8,192,422 B2 6/2012 Zubiate et al.
8,206,287 B2 6/2012 Matsuo
8,226,548 B2 7/2012 Kucklick
8,241,208 B2 8/2012 Jiang et al.
8,241,299 B2 8/2012 Hibner
8,246,575 B2 8/2012 Viola
8,257,257 B2 9/2012 Takizawa et al.
8,262,677 B2 9/2012 Goto
8,298,161 B2 10/2012 Vargas
8,313,014 B2 11/2012 Bettuchi
8,361,090 B2 1/2013 Belson
8,366,606 B2 2/2013 Watanabe et al.
8,388,519 B2 3/2013 Garcia et al.
8,439,825 B2 5/2013 Sekiguchi
8,460,179 B2 6/2013 Ikeda et al.
8,485,968 B2 7/2013 Weimer et al.
8,496,648 B2 7/2013 Rogers
8,506,479 B2 8/2013 Piskun et al.
8,517,923 B2 8/2013 Belson et al.
8,545,491 B2 10/2013 Abboud et al.
8,550,989 B2 10/2013 Dohl et al.
8,556,804 B2 10/2013 Smith et al.
8,663,096 B2 3/2014 Viola
8,663,196 B2 3/2014 Kassab et al.
8,708,894 B2 4/2014 Smith et al.
8,721,530 B2 5/2014 Ohline et al.
8,753,312 B2 6/2014 Bowe et al.
8,777,844 B1 7/2014 Sadanand
8,920,369 B2 12/2014 Salahieh et al.
8,969,639 B2 3/2015 Xu et al.
8,992,420 B2 3/2015 Maahs et al.
9,011,318 B2 4/2015 Choset et al.
9,066,655 B2 6/2015 Stefanchik et al.
9,114,228 B2 8/2015 Zook et al.
9,125,653 B2 9/2015 Kovach
9,155,451 B2 10/2015 Smith et al.
9,192,284 B2 11/2015 Hirsch et al.
9,192,288 B2 11/2015 Okaniwa
9,211,140 B2 12/2015 Lauryssen et al.
9,220,398 B2 12/2015 Woodley et al.
9,226,825 B2 1/2016 Starksen et al.
9,241,611 B2 1/2016 Konno
9,254,123 B2 2/2016 Alvarez et al.
9,282,993 B1 3/2016 Cohen et al.
9,295,511 B2 3/2016 Smith et al.
9,333,287 B2 5/2016 Nitsan et al.
9,358,073 B2 6/2016 Piligian et al.
9,364,955 B2 6/2016 Oyola et al.
9,386,910 B2 7/2016 West
9,498,108 B1 11/2016 Lombardi
9,498,198 B2 11/2016 Hu et al.
9,505,125 B2 11/2016 Zubiate et al.
9,585,546 B2 3/2017 Surti et al.
9,610,068 B2 4/2017 Kappel et al.
9,649,473 B2 5/2017 Gregorich et al.
9,763,562 B2 9/2017 Avitsian et al.
9,814,372 B2 11/2017 Smith et al.
9,913,570 B2 3/2018 Kucharski et al.
9,937,324 B2 4/2018 Kim et al.
9,993,142 B2 6/2018 Salman et al.
10,092,291 B2 10/2018 Voegele et al.
10,307,042 B2 6/2019 Lombardi
10,463,495 B2 11/2019 Rogers et al.
10,625,413 B1 4/2020 McPherson
10,682,108 B1 6/2020 Ma et al.
10,959,607 B2 3/2021 Rogers et al.
11,006,975 B1 5/2021 Cohen et al.
11,020,214 B2 6/2021 Gupta et al.
11,122,971 B2 9/2021 Tilson et al.
11,135,398 B2 10/2021 Tilson et al.
11,219,351 B2 1/2022 Tilson et al.
11,478,608 B2 10/2022 Tilson et al.
11,554,248 B1 1/2023 Tilson et al.
11,724,065 B2 8/2023 Tilson et al.
2001/0041881 A1 11/2001 Sarge et al.
2002/0049423 A1 4/2002 Howell et al.
2002/0107478 A1 8/2002 Wendlandt
2002/0161355 A1 10/2002 Wollschlager
2003/0023259 A1 1/2003 Dubrul et al.
2003/0035048 A1 2/2003 Shipp
2003/0036748 A1 2/2003 Cooper et al.
2003/0083546 A1 5/2003 Butler et al.
2003/0122374 A1 7/2003 Ouchi et al.
2003/0153866 A1 8/2003 Long et al.
2003/0208220 A1 11/2003 Worley et al.
2003/0216681 A1 11/2003 Zhang et al.
2003/0216691 A1 11/2003 Jacobson
2003/0225379 A1 12/2003 Schaffer et al.
2004/0019252 A1 1/2004 Hirata
2004/0044350 A1 3/2004 Martin et al.
2004/0092960 A1 5/2004 Abrams et al.
2004/0186349 A1 9/2004 Ewers et al.
2004/0186350 A1 9/2004 Brenneman et al.
2004/0242958 A1 12/2004 Fujikawa et al.
2004/0243227 A1 12/2004 Starksen et al.
2004/0260236 A1 12/2004 Manning et al.
2005/0004523 A1 1/2005 Osborne et al.
2005/0005363 A1 1/2005 Giori et al.
2005/0010237 A1 1/2005 Niazi
2005/0085829 A1 4/2005 Kraemer et al.
2005/0113643 A1 5/2005 Hale et al.
2005/0154258 A1 7/2005 Tartaglia et al.
2005/0165275 A1 7/2005 Von Felten et al.
2005/0165366 A1 7/2005 Brustad et al.
2005/0203340 A1 9/2005 Butler et al.
2005/0251998 A1 11/2005 Or et al.
2005/0261581 A1 11/2005 Hughes et al.
2005/0272974 A1 12/2005 Iddan
2005/0277966 A1 12/2005 Ewers et al.
2006/0015010 A1 1/2006 Jaffe et al.
2006/0041188 A1 2/2006 Dirusso et al.
2006/0047183 A1 3/2006 Park
2006/0058582 A1 3/2006 Maahs et al.
2006/0063973 A1 3/2006 Makower et al.
2006/0089530 A1 4/2006 Tartaglia
2006/0106285 A1 5/2006 Boulais et al.
2006/0111611 A1 5/2006 Eizenfeld et al.
2006/0129130 A1 6/2006 Tal et al.
2006/0178560 A1 8/2006 Saadat et al.
2006/0192465 A1 8/2006 Kombluh et al.
2006/0199999 A1 9/2006 Ikeda et al.
2006/0235457 A1 10/2006 Belson
2006/0235458 A1 10/2006 Belson
2006/0258906 A1 11/2006 Binmoeller
2006/0264707 A1 11/2006 Kinney
2006/0264821 A1 11/2006 Vo et al.
2006/0287666 A1 12/2006 Saadat et al.
2007/0015965 A1 1/2007 Cox et al.
2007/0038025 A1 2/2007 Yoshida

(56) References Cited

U.S. PATENT DOCUMENTS

| | | | |
|---|---|---|---|
| 2007/0045504 A1 | 3/2007 | Wollschlager | |
| 2007/0088367 A1 | 4/2007 | Weymarn-Scharti | |
| 2007/0100414 A1 | 5/2007 | Licata et al. | |
| 2007/0106302 A1 | 5/2007 | Ortiz | |
| 2007/0118015 A1 | 5/2007 | Wendlandt | |
| 2007/0135803 A1 | 6/2007 | Belson | |
| 2007/0156018 A1 | 7/2007 | Krauter et al. | |
| 2007/0213591 A1 | 9/2007 | Aizenfeld et al. | |
| 2007/0219411 A1 | 9/2007 | Dejima et al. | |
| 2007/0239252 A1 | 10/2007 | Hopkins et al. | |
| 2007/0250113 A1 | 10/2007 | Hegeman et al. | |
| 2007/0250149 A1 | 10/2007 | Oepen et al. | |
| 2007/0255101 A1 | 11/2007 | Bar Or | |
| 2007/0260121 A1 | 11/2007 | Bakos et al. | |
| 2007/0282358 A1 | 12/2007 | Remiszewski et al. | |
| 2008/0009669 A1 | 1/2008 | Ozawa et al. | |
| 2008/0051635 A1 | 2/2008 | Tanaka et al. | |
| 2008/0058722 A1 | 3/2008 | Oepen et al. | |
| 2008/0091073 A1 | 4/2008 | Park | |
| 2008/0103440 A1 | 5/2008 | Ferren et al. | |
| 2008/0139887 A1 | 6/2008 | Fitzpatrick | |
| 2008/0172037 A1 | 7/2008 | Huang et al. | |
| 2008/0188928 A1 | 8/2008 | Salahieh et al. | |
| 2008/0200762 A1 | 8/2008 | Stokes et al. | |
| 2008/0214893 A1 | 9/2008 | Tartaglia et al. | |
| 2008/0234546 A1 | 9/2008 | Kawano et al. | |
| 2008/0242928 A1 | 10/2008 | Kawano et al. | |
| 2008/0249362 A1 | 10/2008 | Jiang et al. | |
| 2008/0262300 A1 | 10/2008 | Ewers et al. | |
| 2008/0262301 A1 | 10/2008 | Gibbons et al. | |
| 2008/0275299 A1 | 11/2008 | Park | |
| 2008/0318456 A1 | 12/2008 | Yow et al. | |
| 2008/0319266 A1 | 12/2008 | Poll et al. | |
| 2009/0023983 A1 | 1/2009 | Stefanchik | |
| 2009/0048483 A1 | 2/2009 | Yamamoto | |
| 2009/0062611 A1 | 3/2009 | Toyama | |
| 2009/0062837 A1 | 3/2009 | Gasche et al. | |
| 2009/0062872 A1 | 3/2009 | Chin et al. | |
| 2009/0104250 A1 | 4/2009 | Boyden et al. | |
| 2009/0112063 A1 | 4/2009 | Bakos et al. | |
| 2009/0112064 A1 | 4/2009 | Levey et al. | |
| 2009/0131752 A1 | 5/2009 | Park | |
| 2009/0157068 A1 | 6/2009 | Kallel et al. | |
| 2009/0187163 A1 | 7/2009 | Uihlein | |
| 2009/0240202 A1 | 9/2009 | Drasler et al. | |
| 2009/0248041 A1 | 10/2009 | Williams et al. | |
| 2009/0259200 A1 | 10/2009 | Lampropoulos et al. | |
| 2009/0264704 A1 | 10/2009 | Shtul | |
| 2010/0010308 A1 | 1/2010 | Braun et al. | |
| 2010/0010437 A1 | 1/2010 | Miles et al. | |
| 2010/0010504 A1 | 1/2010 | Simaan et al. | |
| 2010/0016663 A1 | 1/2010 | Maisch et al. | |
| 2010/0036363 A1 | 2/2010 | Watanabe et al. | |
| 2010/0069712 A1 | 3/2010 | Yamaya | |
| 2010/0069716 A1 | 3/2010 | Chin et al. | |
| 2010/0076451 A1 | 3/2010 | Zwolinski et al. | |
| 2010/0087711 A1 | 4/2010 | Edwards | |
| 2010/0137686 A1 | 6/2010 | Meron et al. | |
| 2010/0145151 A1 | 6/2010 | Fukunaga et al. | |
| 2010/0160735 A1 | 6/2010 | Bakos | |
| 2010/0185172 A1 | 7/2010 | Fabro | |
| 2010/0204546 A1 | 8/2010 | Hassidov et al. | |
| 2010/0268025 A1 | 10/2010 | Belson | |
| 2010/0331625 A1 | 12/2010 | Rosemurgy et al. | |
| 2010/0331820 A1 | 12/2010 | Prisco et al. | |
| 2011/0015729 A1 | 1/2011 | Jimenez et al. | |
| 2011/0023888 A1 | 2/2011 | Vazales et al. | |
| 2011/0040282 A1 | 2/2011 | Uihlein | |
| 2011/0046442 A1* | 2/2011 | Matsushita | A61B 1/0055 600/114 |
| 2011/0049282 A1 | 3/2011 | Danielsson | |
| 2011/0054253 A1 | 3/2011 | Jordá Albiñana et al. | |
| 2011/0087070 A1 | 4/2011 | Tilson et al. | |
| 2011/0196392 A1 | 8/2011 | Saadat et al. | |
| 2011/0237888 A1 | 9/2011 | Matsushita | |
| 2011/0245611 A1 | 10/2011 | Yeh et al. | |
| 2011/0263938 A1 | 10/2011 | Levy | |
| 2011/0282149 A1 | 11/2011 | Vargas et al. | |
| 2011/0288553 A1 | 11/2011 | Jansen et al. | |
| 2011/0301414 A1 | 12/2011 | Hotto et al. | |
| 2011/0306950 A1 | 12/2011 | Cucin | |
| 2011/0319714 A1 | 12/2011 | Roelle et al. | |
| 2012/0004676 A1 | 1/2012 | Vargas | |
| 2012/0022329 A1 | 1/2012 | Wagh et al. | |
| 2012/0041291 A1 | 2/2012 | Ferren et al. | |
| 2012/0095448 A1 | 4/2012 | Kaji | |
| 2012/0095548 A1 | 4/2012 | Gregorich et al. | |
| 2012/0108902 A1 | 5/2012 | Frassica et al. | |
| 2012/0130173 A1 | 5/2012 | Lutze et al. | |
| 2012/0143005 A1 | 6/2012 | Yeh et al. | |
| 2012/0143006 A1 | 6/2012 | Avitsian et al. | |
| 2012/0165607 A1 | 6/2012 | Ashida et al. | |
| 2012/0165792 A1 | 6/2012 | Ortiz et al. | |
| 2012/0172651 A1 | 7/2012 | Cutrer | |
| 2012/0209062 A1 | 8/2012 | Qiao | |
| 2012/0209292 A1 | 8/2012 | Devengenzo et al. | |
| 2012/0277528 A1 | 11/2012 | Qiao | |
| 2012/0277729 A1 | 11/2012 | Melsheimer | |
| 2013/0023920 A1 | 1/2013 | Terliuc et al. | |
| 2013/0131641 A1 | 5/2013 | Jimenez et al. | |
| 2013/0190565 A1 | 7/2013 | Gora et al. | |
| 2013/0274553 A1 | 10/2013 | Piskun | |
| 2013/0289478 A1* | 10/2013 | Kim | A61B 1/00078 604/95.04 |
| 2013/0304179 A1 | 11/2013 | Bialas et al. | |
| 2013/0333472 A1 | 12/2013 | Georgeson | |
| 2013/0338440 A1 | 12/2013 | Sinai et al. | |
| 2014/0005683 A1 | 1/2014 | Stand et al. | |
| 2014/0073853 A1* | 3/2014 | Swisher | A61J 15/0026 600/104 |
| 2014/0081169 A1 | 3/2014 | Gerding et al. | |
| 2014/0088459 A1 | 3/2014 | Roush et al. | |
| 2014/0142393 A1 | 5/2014 | Piskun et al. | |
| 2014/0155702 A1 | 6/2014 | Tilson et al. | |
| 2014/0155783 A1 | 6/2014 | Starksen et al. | |
| 2014/0171736 A1 | 6/2014 | Stigall et al. | |
| 2014/0188054 A1 | 7/2014 | Iijima et al. | |
| 2014/0207083 A1 | 7/2014 | Pessin | |
| 2014/0243796 A1 | 8/2014 | Tegg et al. | |
| 2014/0243873 A1 | 8/2014 | Franklin | |
| 2014/0275860 A1 | 9/2014 | Rottenberg et al. | |
| 2014/0276601 A1 | 9/2014 | Edward | |
| 2014/0276642 A1 | 9/2014 | Cully et al. | |
| 2014/0309587 A1 | 10/2014 | Kim et al. | |
| 2014/0309661 A1 | 10/2014 | Sheps et al. | |
| 2014/0343358 A1 | 11/2014 | Hameed et al. | |
| 2014/0371718 A1 | 12/2014 | Alvarez et al. | |
| 2014/0371764 A1 | 12/2014 | Oyola et al. | |
| 2015/0018616 A1 | 1/2015 | Kumoyama | |
| 2015/0038919 A1 | 2/2015 | Bramwell et al. | |
| 2015/0073216 A1 | 3/2015 | Papay | |
| 2015/0073342 A1 | 3/2015 | Pacheco et al. | |
| 2015/0073409 A1 | 3/2015 | Watson et al. | |
| 2015/0094656 A1 | 4/2015 | Salahich et al. | |
| 2015/0119640 A1 | 4/2015 | Reydel | |
| 2015/0126814 A1 | 5/2015 | Mesallum et al. | |
| 2015/0133729 A1 | 5/2015 | Reydel | |
| 2015/0142013 A1 | 5/2015 | Tanner et al. | |
| 2015/0148602 A1 | 5/2015 | Hill et al. | |
| 2015/0148606 A1 | 5/2015 | Rottenberg et al. | |
| 2015/0164314 A1 | 6/2015 | Peterson | |
| 2015/0216589 A1 | 8/2015 | Wittenberger et al. | |
| 2015/0276097 A1 | 10/2015 | Carlson et al. | |
| 2015/0313445 A1 | 11/2015 | Davidson et al. | |
| 2015/0335387 A1 | 11/2015 | Atzinger et al. | |
| 2015/0342608 A1 | 12/2015 | Hernandez | |
| 2015/0369325 A1 | 12/2015 | Bureau et al. | |
| 2016/0007832 A1 | 1/2016 | Shimada | |
| 2016/0015259 A1 | 1/2016 | Mody et al. | |
| 2016/0038002 A1 | 2/2016 | Peters et al. | |
| 2016/0058268 A1 | 3/2016 | Salman et al. | |
| 2016/0066773 A1 | 3/2016 | Cooper et al. | |
| 2016/0096004 A1 | 4/2016 | Gerrans et al. | |
| 2016/0129547 A1 | 5/2016 | Duescher et al. | |

(56) References Cited

U.S. PATENT DOCUMENTS

| | | | |
|---|---|---|---|
| 2016/0136393 | A1 | 5/2016 | Tsai et al. |
| 2016/0174829 | A1 | 6/2016 | Reydel |
| 2016/0198935 | A1 | 7/2016 | Choi et al. |
| 2016/0206425 | A1 | 7/2016 | Madrid et al. |
| 2016/0270870 | A1 | 9/2016 | Kowshik |
| 2016/0279388 | A1 | 9/2016 | Barrish et al. |
| 2016/0287059 | A1 | 10/2016 | Ha et al. |
| 2016/0302818 | A1 | 10/2016 | Weisenburgh et al. |
| 2016/0309989 | A1 | 10/2016 | Sato et al. |
| 2016/0324412 | A1 | 11/2016 | Hassidov et al. |
| 2017/0023154 | A1 | 1/2017 | Jaeker et al. |
| 2017/0156567 | A1 | 6/2017 | Kaneko |
| 2017/0157363 | A1 | 6/2017 | Barrish et al. |
| 2017/0312920 | A1 | 11/2017 | Yip et al. |
| 2017/0333681 | A1 | 11/2017 | Di Caprio et al. |
| 2017/0340862 | A1 | 11/2017 | Calabrese et al. |
| 2017/0360281 | A1 | 12/2017 | Ponsky |
| 2018/0015257 | A1 | 1/2018 | Krolik et al. |
| 2018/0043134 | A1 | 2/2018 | Alvarez et al. |
| 2018/0064366 | A1 | 3/2018 | Sweeney et al. |
| 2018/0078282 | A1 | 3/2018 | Takemoto |
| 2018/0085559 | A1 | 3/2018 | Laby et al. |
| 2018/0126144 | A1 | 5/2018 | Furnish et al. |
| 2018/0132705 | A1 | 5/2018 | Higuchi |
| 2018/0184885 | A1 | 7/2018 | St. George |
| 2018/0249893 | A1 | 9/2018 | Yeung et al. |
| 2018/0256876 | A1 | 9/2018 | Furnish et al. |
| 2018/0263469 | A1 | 9/2018 | Okaniwa et al. |
| 2018/0264239 | A1 | 9/2018 | Piskun |
| 2018/0289925 | A1 | 10/2018 | Palmer et al. |
| 2018/0326197 | A1 | 11/2018 | McArthur et al. |
| 2018/0361116 | A1 | 12/2018 | Quick et al. |
| 2018/0374603 | A1 | 12/2018 | Greenwood |
| 2019/0046012 | A1 | 2/2019 | Ikeda |
| 2019/0226447 | A1 | 7/2019 | Stecher et al. |
| 2020/0022712 | A1 | 1/2020 | Deville et al. |
| 2020/0030575 | A1 | 1/2020 | Bogusky et al. |
| 2020/0100653 | A1 | 4/2020 | Nakamura |
| 2020/0171276 | A1 | 6/2020 | Onozuka |
| 2020/0178763 | A1 | 6/2020 | Tilson et al. |
| 2020/0230808 | A1 | 7/2020 | Simaan et al. |
| 2020/0237198 | A1 | 7/2020 | Liu et al. |
| 2020/0315429 | A1 | 10/2020 | Russo et al. |
| 2020/0315433 | A1 | 10/2020 | Axon et al. |
| 2020/0383677 | A1 | 12/2020 | Piligian et al. |
| 2020/0391002 | A1 | 12/2020 | Hilton et al. |
| 2021/0000505 | A1 | 1/2021 | Lenker et al. |
| 2021/0030260 | A1 | 2/2021 | Julian et al. |
| 2021/0045626 | A1 | 2/2021 | Hsu et al. |
| 2021/0114507 | A1 | 4/2021 | Alexander et al. |
| 2021/0137366 | A1 | 5/2021 | Tilson et al. |
| 2021/0138187 | A1* | 5/2021 | Tilson ............... A61M 25/0102 |
| 2021/0197684 | A1 | 7/2021 | Graham et al. |
| 2021/0228973 | A1 | 7/2021 | Conte |
| 2021/0280312 | A1 | 9/2021 | Freedman et al. |
| 2021/0323767 | A1 | 10/2021 | Liu et al. |
| 2021/0330938 | A1 | 10/2021 | Kendrick et al. |
| 2021/0361895 | A1 | 11/2021 | Nekhendzy et al. |
| 2022/0000346 | A1 | 1/2022 | Switzer |
| 2022/0000355 | A1 | 1/2022 | Tilson et al. |
| 2022/0104690 | A1 | 4/2022 | Tilson et al. |
| 2022/0323166 | A1 | 10/2022 | Tilson et al. |
| 2022/0347430 | A1 | 11/2022 | Pedersen |
| 2022/0369903 | A1 | 11/2022 | Schneider et al. |
| 2022/0414880 | A1 | 12/2022 | Inoue et al. |
| 2023/0014281 | A1 | 1/2023 | Tilson et al. |
| 2023/0017488 | A1 | 1/2023 | Somasundaram et al. |
| 2023/0034024 | A1 | 2/2023 | Cope et al. |
| 2023/0070264 | A1 | 3/2023 | Leuthardt et al. |
| 2023/0120269 | A1 | 4/2023 | Lopez et al. |
| 2023/0121021 | A1 | 4/2023 | Sinay et al. |
| 2023/0138203 | A1 | 5/2023 | Bazdanes et al. |
| 2023/0210351 | A1 | 7/2023 | Scheeff et al. |
| 2023/0346399 | A1 | 11/2023 | Schaller et al. |
| 2023/0353879 | A1 | 11/2023 | Nishide et al. |
| 2023/0380662 | A1 | 11/2023 | Slawinski et al. |
| 2023/0404486 | A1 | 12/2023 | Carreel et al. |
| 2023/0404701 | A1 | 12/2023 | Romo et al. |
| 2024/0016638 | A1 | 1/2024 | McGowan et al. |
| 2024/0016639 | A1 | 1/2024 | McGowan et al. |
| 2024/0188805 | A1 | 6/2024 | Tilson et al. |
| 2024/0358232 | A1 | 10/2024 | Joseph et al. |
| 2025/0090801 | A1 | 3/2025 | Zayed et al. |
| 2025/0134352 | A1 | 5/2025 | Tilson et al. |
| 2025/0169678 | A1 | 5/2025 | Tilson et al. |
| 2025/0194904 | A1 | 6/2025 | Tilson et al. |
| 2025/0262407 | A1 | 8/2025 | Tilson et al. |

FOREIGN PATENT DOCUMENTS

| | | | |
|---|---|---|---|
| CN | 1706349 | A | 12/2005 |
| CN | 1732855 | A | 2/2006 |
| CN | 1764800 | A | 4/2006 |
| CN | 1806770 | A | 7/2006 |
| CN | 1861011 | A | 11/2006 |
| CN | 101119765 | A | 2/2008 |
| CN | 101129255 | A | 2/2008 |
| CN | 101888872 | A | 11/2010 |
| CN | 102137628 | A | 7/2011 |
| CN | 201899767 | U | 7/2011 |
| CN | 102711585 | A | 10/2012 |
| CN | 102872519 | A | 1/2013 |
| CN | 103384500 | A | 11/2013 |
| CN | 104168860 | A | 11/2014 |
| CN | 104287684 | B | 3/2016 |
| CN | 105759418 | A | 7/2016 |
| CN | 105813536 | A | 7/2016 |
| CN | 105832279 | A | 8/2016 |
| CN | 106137397 | A | 11/2016 |
| CN | 106455929 | A | 2/2017 |
| CN | 106488744 | A | 3/2017 |
| CN | 106659367 | A | 5/2017 |
| CN | 106823102 | A | 6/2017 |
| CN | 107296584 | A | 10/2017 |
| CN | 107697631 | A | 2/2018 |
| CN | 109883620 | A | 6/2019 |
| CN | 110077771 | A | 8/2019 |
| CN | 110582324 | A | 12/2019 |
| CN | 111465420 | A | 7/2020 |
| CN | 212558299 | U | 2/2021 |
| DE | 102005039601 | A1 | 2/2007 |
| DE | 102017219621 | A1 | 3/2019 |
| EP | 401129 | A1 | 12/1990 |
| EP | 0941743 | A2 | 9/1999 |
| EP | 1662972 | A2 | 6/2006 |
| EP | 1695657 | A1 | 8/2006 |
| EP | 1487318 | B1 | 3/2008 |
| EP | 2016914 | A2 | 1/2009 |
| EP | 1499227 | B1 | 10/2010 |
| EP | 2258322 | A2 | 12/2010 |
| EP | 2364637 | A1 | 9/2011 |
| EP | 2368481 | A1 | 9/2011 |
| EP | 2368483 | A1 | 9/2011 |
| EP | 3256052 | A1 | 12/2017 |
| EP | 2604175 | B1 | 11/2019 |
| GB | 2482355 | A | 10/2010 |
| GB | 2497544 | A | 6/2013 |
| JP | S6289014 | A | 4/1987 |
| JP | H05220102 | A | 8/1993 |
| JP | H05293077 | A | 11/1993 |
| JP | H0644503 | U | 6/1994 |
| JP | H06335531 | A | 12/1994 |
| JP | 2002125921 | A | 5/2002 |
| JP | 2003501197 | A | 1/2003 |
| JP | 2003508133 | A | 3/2003 |
| JP | 2005152300 | A | 6/2005 |
| JP | 2005323778 | A | 11/2005 |
| JP | 2006068449 | A | 3/2006 |
| JP | 03965108 | B2 | 8/2007 |
| JP | 2009506839 | A | 2/2009 |
| JP | 2009507617 | A | 2/2009 |
| JP | 2009061173 | A | 3/2009 |
| JP | 2010000360 | A | 1/2010 |
| JP | 2010279795 | A | 12/2010 |

(56) References Cited

FOREIGN PATENT DOCUMENTS

| | | | |
|---|---|---|---|
| JP | 2011194126 | A | 10/2011 |
| JP | 2012183232 | A | 9/2012 |
| JP | 2013514150 | A | 4/2013 |
| JP | 2013176465 | A | 9/2013 |
| JP | 2014124475 | A | 7/2014 |
| JP | 2015525609 | A | 9/2015 |
| JP | 2017506129 | A | 3/2017 |
| JP | 2018500054 | A | 1/2018 |
| JP | 2018514350 | A | 6/2018 |
| JP | 2018525197 | A | 9/2018 |
| JP | 2018537229 | A | 12/2018 |
| JP | 6829351 | B1 | 2/2021 |
| JP | 2021175686 | A | 11/2021 |
| KR | 10-2015-0131502 | A | 11/2015 |
| KR | 20180053852 | A | 5/2018 |
| KR | 101908933 | B1 | 10/2018 |
| TW | 201438661 | A | 10/2014 |
| WO | WO97/43941 | A1 | 11/1997 |
| WO | WO99/053827 | A1 | 10/1999 |
| WO | WO03/013348 | A1 | 2/2003 |
| WO | WO2004/047626 | A1 | 6/2004 |
| WO | WO2005/110199 | A1 | 11/2005 |
| WO | WO2005/110200 | A1 | 11/2005 |
| WO | WO2007/035931 | A2 | 3/2007 |
| WO | WO2008/041809 | A1 | 4/2008 |
| WO | WO2008/122969 | A1 | 10/2008 |
| WO | WO2008/122997 | A1 | 10/2008 |
| WO | WO2009/154192 | A1 | 12/2009 |
| WO | WO2011/018147 | A1 | 2/2011 |
| WO | WO2011/018157 | A1 | 2/2011 |
| WO | WO2011/148172 | A2 | 12/2011 |
| WO | WO2012/054480 | A2 | 4/2012 |
| WO | WO2012/080947 | A1 | 6/2012 |
| WO | WO2012/122288 | A2 | 9/2012 |
| WO | WO2013/132992 | A1 | 9/2013 |
| WO | WO2014/081892 | A1 | 5/2014 |
| WO | WO2016/034598 | A1 | 3/2016 |
| WO | WO2016/190324 | A1 | 12/2016 |
| WO | WO2017/041052 | A1 | 3/2017 |
| WO | WO2018/035452 | A1 | 8/2017 |
| WO | WO2019/054867 | A1 | 3/2019 |
| WO | WO2019/160865 | A1 | 8/2019 |
| WO | WO2020/018934 | A1 | 1/2020 |
| WO | WO2020/214221 | A1 | 10/2020 |
| WO | WO2020/237426 | A1 | 12/2020 |
| WO | WO2021/202336 | A1 | 10/2021 |
| WO | WO2021/242884 | A1 | 12/2021 |
| WO | WO2022/051682 | A1 | 3/2022 |
| WO | WO2022/087093 | A1 | 4/2022 |
| WO | WO2022/146939 | A1 | 7/2022 |
| WO | WO2022/159861 | A1 | 7/2022 |
| WO | WO2022/165302 | A1 | 8/2022 |
| WO | WO2022/192515 | A3 | 9/2022 |
| WO | WO2023/122667 | A1 | 6/2023 |
| WO | WO2023/122767 | A2 | 6/2023 |
| WO | WO2023/133403 | A1 | 7/2023 |
| WO | WO2023/154743 | A2 | 8/2023 |
| WO | WO2023/183952 | A2 | 9/2023 |
| WO | WO2023/205655 | A2 | 10/2023 |
| WO | WO2023/212641 | A2 | 11/2023 |
| WO | WO2023/225520 | A2 | 11/2023 |
| WO | WO2013/184192 | A2 | 12/2023 |
| WO | WO2024/030975 | A2 | 2/2024 |
| WO | WO2025/171405 | A1 | 8/2025 |

OTHER PUBLICATIONS

Entrada® colonic overtube product brochure downloaded from internet http://www.usendoscopy.com/~/media/Files/Documents/Spec-Sheet-International/760358c_entrada_intl_ss_web.pdf Accessed Date: Jun. 5, 2017 (the year of publication is sufficiently earlier than the effective U.S. filing date and any foreign priority date so that the particular month of publication is not in issue) 2009.

Filip et al.; Design, Implementation, and Testing of a miniature self-stabilizing capsule endoscope with wireless image transmission capabilities; Intl. Journal "Information Technologies & Knowledge"; 5(1); downloaded from http://www.foibg.com/ijitk/ijitk-vol05/ijitk05-1-p01.pdf on Jul. 28, 2016; (the year of publication is sufficiently earlier than the effective U.S. filing date and any foreign priority date so that the particular month of publication is not in issue) 2011.

Loeve et al.; Endoscope Shaft-Rigidity Control Mechanism: "Forguide"; IEEE Trans. on Biomed. Eng.; 59(2); pp. 542-551; Feb. 2012.

Loeve et al.; Vacuum packed particles as flexible endoscope guides with controllable rigidity; Granular Matter; 12(6); pp. 543-554; Jun. 24, 2010.

Shah et al.; Magnetic Imaging of Colonoscopy: An Audit of Looping, Accuracy and Ancillary maneuvers; Gastrointest. Endosc.; 52(1); pp. 1-8; Jul. 1, 2000.

Simi et al.; Design, Fabrication, and Testing of a Capsule With Hybrid Locomotion for Gastrointestinal Tract Exploration; IEEE/ASME Trans on Mechatronics; 15(2); pp. 170-x; Apr. 2010.

Valdastri et al.; Advanced Technologies for Gastrointestinal Endoscopy; Annu. Rev. Biomed. Eng.; 14; pp. 397-429; May 2012.

Zhao et al.; Development of a variable stiffness over tube based on low-melting-point-alloy for endoscopic surgery; J. Med. Devices; 10(2); 8 pages; May 12, 2016.

Gomes et al.; U.S. Appl. No. 18/044,027 entitled "Dynamically rigidizing guiderail and methods of use," filed Mar. 3, 2023.

Tilson et al.; U.S. Appl. No. 18/325,979 entitled "Apparatuses and methods for determining if an endscope is contaminated," filed May 30, 2023.

Tilson et al.; U.S. Appl. No. 18/325,990 entitled "Multi-lumen port adapter mainfold devices and methods of use," filed May 30, 2023.

Mayinger et al.; Disposable-sheath, flexible gastroscope system versus standard gastroscopes: a prospective, randomized trial; Gastrointestinal Endoscopy; 50(4); pp. 461-467; Oct. 1999.

Ofstead et al.; A systematic review of disposable sheath use during flexible endoscopy; AORN Journal; 109(6); pp. 757-771; Jun. 2019.

Rothstein et al.; Disposable, sheathed, flexible sigmoidoscopy: a prospective, multicenter, randomized trial; Gastrointestinal Endoscopy; 41(6); pp. 566-572; Jun. 1995.

Sardinha et al.; Efficiency and productivity of a sheathed fiberoptic sigmoidoscope compared with a conventional sigmoidoscope; Diseases of the Colon and Rectum; 40(10); pp. 1248-1253; Oct. 1997.

Gomes et al.; U.S. Appl. No. 18/263,517 entitled "Devices and methods to prevent inadvertent motion of dynamically rigidizing apparatuses," filed Jul. 28, 2023.

Lopez et al.; U.S. Appl. No. 18/334,555 entitled "Layered walls for rididizing devices," filed Jun. 14, 2023.

Tilson et al.; U.S. Appl. No. 18/343,561 entitled "Nested rigidizing devices," filed Jun. 28, 2023.

Tilson et al.; U.S. Appl. No. 18/262,904 entitled "Large diameter hemostasis valves," filed Jul. 25, 2023.

Bearing Works; PTFE Datasheet; 2 pages; Jan. 21, 2021 retrieved from the internet (https://www.bearingworks.com/uploaded-assets/pdfs/retainers/ptfe-datasheet.pdf) on Nov. 10, 2023.

Tilson et al.; U.S. Appl. No. 18/235,719 entitled "External working channels," filed Aug. 18, 2023.

Tanner et al.; U.S. Appl. No. 18/550,123 entitled "Control of robotic dynamically rigidizing composite medical structures," filed Sep. 11, 2023.

Ferrante et al.; U.S. Appl. No. 18/851,053 entitled "Methods and apparatuses for navigating using a pair of rigidizing devices," filed Sep. 25, 2024.

Tilson et al.; U.S. Appl. No. 18/908,776 entitled "Methods of attaching a rigidizing sheath to an endoscope," filed Oct. 7, 2024.

Tilson et al.; U.S. Appl. No. 18/592,516 entitled "Device and method for enhanced visualization of the small intestine," filed Feb. 29, 2024.

Tilson et al.; U.S. Appl. No. 18/660,205 entitled "Device and method for enhanced visualiztion of the small intestine," filed May 9, 2024.

Tilson et al.; U.S. Appl. No. 18/751,188 entitled "Rigidzing overtube," filed Jun. 21, 2024.

(56) References Cited

OTHER PUBLICATIONS

Tilson et al.; U.S. Appl. No. 18/809,322 entitled "Rigidizing overtube," filed Aug. 19, 2024.
Tilson et al.; U.S. Appl. No. 18/810,458 entitled "Rigidizing overtube," filed Aug. 20, 2024.
Gomes et al.; U.S. Appl. No. 18/837,186 entitled "Dynamically rigidizing composite medical structure," filed Aug. 8, 2024.
Tilson et al.; U.S. Appl. No. 18/858,743 entitled "Managing and manipulating a long length robotic endoscope," filed Oct. 21, 2024.
Witte et al.; U.S. Appl. No. 18/829,229 entitled "Pressure rigidization apparatuses and methods," filed Sep. 9, 2024.
Gomes et al.; U.S. Appl. No. 18/806,692 entitled "Devices and methods to prevent inadvertent motion of dynamically rigidizing apparatuses," filed Aug. 15, 2024.
Tilson et al.; U.S. Appl. No. 18/780,429 entitled "Device for endoscopic advancement through the small intestine," filed Jul. 22, 2024.
Eisler et al.; U.S. Appl. No. 18/852,419 entitled "Rigidizing aspiration systems and methods," filed Sep. 27, 2024.
Mayinger et al.; Disposable protection for flexible gastroenterologic endoscopy: prospective comparative evaluation of a new gastroscopy system (Endosheath) compared to the standard fiberglass gastroscope; (English Abstract Only); Zeitschrift Fur Gastrenterologie; 36(6); pp. 501-507; Jun. 1998 (Eng Abs only).
Lopez et al.; U.S. Appl. No. 18/723,414 entitled "Methods and apparatuses for reducing curvature of a colon," filed Jun. 21, 2024.
Gomes et al.; U.S. Appl. No. 18/723,413 entitled "Obturator with stiff distal cannula engagement region," filed Jun. 21, 2024.
Morris et al.; U.S. Appl. No. 18/727,032 entitled "Reconfigurable rigidizing structures," filed Jul. 5, 2024.
Tilson et al.; U.S. Appl. No. 18/902,916 entitled "Methods of attaching a rigidizing sheath to an endoscope," filed Sep. 30, 2024.
Devengenzo et al.; U.S. Appl. No. 18/902,906 entitled "Telescoping robot," filed Sep. 30, 2024.
Tilson et al.; U.S. Appl. No. 19/100,929 entitled "Dynamic rigidization methods and apparatuses," filed Feb. 3, 2025.
Devengenzo et al.; U.S. Appl. No. 19/210,595 entitled "Telescoping robot," filed May 16, 2025.
Tilson et al.; U.S. Appl. No. 19/210,485 entitled "Methods of attaching a rigidizing sheath to an endoscope," filed May 16, 2025.
Smooth-On; Durometer Shore Hardness Scale; smooth-on.com; retrieved from the internet (https://www.smooth-on.com/page/durometer-shore-hardness-scale/); 2 pages; 2026.

* cited by examiner

ENDOSCOPE SHEATH APPARATUSES

CLAIM OF PRIORITY

This patent application claims priority as a continuation of PCT Application No. PCT/US2023/066293, titled "HYGIENIC SHEATH FOR ENDOSCOPY," filed on Apr. 27, 2023, which claims priority to U.S. Provisional Patent Application No. 63/335,720, titled "HYGIENIC DRAPING FOR ROBOTIC ENDOSCOPY," filed on Apr. 27, 2022. These applications are herein incorporated by reference in their entireties.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Reusable endoscopes ('scopes'), both manually and robotically operated, perform important diagnostic and therapeutic functions, but have numerous issues. Endoscopes may be difficult to clean because they may be a long length (an enteroscope may be over two meters long), may have one or more very long and very small lumens, and they include a multitude of small, ornate parts constructed from a wide variety of materials that have regions that may shelter microbes. These regions may include regions where parts meet, in cracks and connections, and regions where there are scratches and localized damage. The use of most endoscopes typically requires them to be immersed in pathogen-rich contaminants, including blood, feces, urine, and diseased and infected tissue. Reusable scopes are expected to survive a very large number of cases—often over one thousand—over a long period of time, e.g., several years. However, such long-life expectations create issues: a careful analysis of used scopes shows them to be often damaged both internally and externally. The repair of endoscopes is logistically taxing, requires constant quality-control and inspection, requires expensive back-up devices, shipping, receiving and proper packaging and transport, and is very expensive: a reusable scope typically has lifetime repair costs that exceed the cost of the initial purchase. Because reusable scopes are expected to last for years, it inherently means that clinicians are performing endoscopy with outdated technology. Cleaning scopes also requires considerable capital equipment, as well as their requisite space, training, maintenance, and repair. Successful cleaning of scopes requires the successful execution of highly detailed procedures (often over one hundred separate steps) and often by staff that has significant turnover, is ill-trained, is hurried, is in poor communication with the end-user, and is working without all of the necessary tools. It is well-documented that scope cleaning is not usually performed accurately and completely, as per the full and complete list of cleaning instructions. The complete set of activities necessary to clean and return scopes ready for their next case requires a complicated, time-consuming, multi-person, expensive internal logistics dance as the devices move throughout their various steps in various locations within the hospital, with different tasks being handed-off between a large number of different people and departments. Hospital space is very expensive, and the storage, processing, and movement of these devices creates very real facility costs. Furthermore, the cleaning process often takes the devices out of commission for extended periods of times, requiring that facilities that perform endoscopy maintain a vast arsenal of rotating devices to fulfill their ongoing procedures. Further, despite the impression that re-use is good for the environment, the cleaning of scopes creates a remarkably large amount of landfill—gloves, wipes, brushes, personal protective gear, connectors, tubing, test strips, and hazardous chemicals. The chemical cleaning agents are harsh for the scope, the facility, the environment, and the people performing the cleaning.

Importantly, such cleaning processes may clean a scope, but the processed scope is not sterile (the goal is HLD, High Level Disinfection), because many of the scope's materials cannot withstand the rigors of the requisite chemicals, temperatures, or radiation. Sterilization via ethylene oxide would require long exposure and aeration times, is hazardous to personnel and patients, and has created a large number of very public recent adverse worker health and environmental issues. Sterilization via peroxide is new and promising, but it would still suffer from the majority of above-listed maladies. In the worst case, peroxide-sterilized devices would be sterile, but would still maintain debris burden which could be transferred from case-to-case. Scope contamination is pervasive and, in the worst cases, has resulted in disease transmission and documented deaths.

Currently available resposable scopes are expected to last for multiple cases (e.g., 2, 5, 10, 20, etc.) and suffer from many of the same issues as reusable scopes.

Although disposable scopes typically arrive sterile and never need to be cleaned, they result in significant landfill waste and may be difficult to manufacture at high quality and reasonable costs. Though they could theoretically be recycled, actual recycling is painfully rare and is uneconomical. Disposable scopes have found effective use in certain niches, but they have not been widely adopted.

Surgical drapes, sheaths, and shrouds are used to create a sterile field around a surgical site and establish a physical barrier that reduces the risk of device contamination and surgical site infections. Sheathing can be a key enabler to freeing technicians required to clean waste (e.g., feces) from endoscopes to pursue more meaningful and important work. Hygienic draping, including for both manual and robotic/telerobotic endoscopy, may effectively physically isolate the device from the patient during surgical procedures.

Thus, there is a need for methods, components, systems, and apparatuses to addresses these issues.

SUMMARY OF THE DISCLOSURE

Described herein are methods and apparatuses (e.g., components, accessories, devices and systems, including sheath systems) that may be used with endoscopes, and in particular, manual endoscopes or robotic endoscopes and/or telescoping endoscopes, as well as method of using these sheaths to prevent cross-contamination between patients and contamination of the endoscope. In general, these sheaths may reduce or eliminate the need for endoscope cleaning. The sheaths described herein may also or alternatively be referred to as drapes and may advantageously be quickly and easily applied to an endoscope system for a new patient without a lengthy reprocessing procedure that would otherwise include HLD and/or sterilization. These sheaths may protect the outside of the endoscope as well as any internal working channels and supply lines of the endoscope, which may critically prevent contamination of endoscopes with internal working channels and supply lines during medical procedures. The apparatuses (e.g., components, accessories, devices and systems, including sheath devices and sheath systems) and methods described herein may protect patients from cross-contamination including cross-contamination from other patients, may be faster, easier, and lower cost, may result in less landfill, and may be more effective than reprocessing (cleaning of the endoscope). By reducing or eliminating additional cleaning cycles, the endoscopes may have less wear and associated damage. By effectively sheathing the devices, important scope elements can be reused multiple times, thereby reducing per-case cost and reducing landfill.

The method and apparatuses (e.g., systems and devices, including sheath systems) described herein may include reusable elements, disposable elements, semi-disposable elements (i.e., resposable elements, elements that are reused a modest number of times), and/or draping elements that may address the issues raised above.

As used herein the term "endoscope" is intended to be understood broadly. In general, an endoscope may refer to an instrument which can be introduced into the body and may include one or more lumens extending therethrough. An endoscope may include a catheter, trocar, tube, or the like. An endoscope may refer to an instrument for use in examining, accessing, treating and/or diagnosing the interior of a body, including an organ, lumen, body cavity or vessel. Any of these endoscopes may include imaging (e.g., typically by a CCD, CMOS chip, or fiber optic material) to give a view from the distal end or sides of the device. The endoscopes described herein may include sensing (e.g., electrical sensing, magnetic sensing, shape sensing, mechanical sensing, etc.). The endoscope may generally be a catheter including one (or more than one) internal lumen extending the length of the endoscope. In some examples the endoscope may include one or more internal lumens extending the length of the endoscope (e.g., an internal working channel, fluid channels, insufflation channels, wash channels, etc.). For example, any of these endoscopes may include a channel or channels for applying or removing liquid and/or gas (e.g., aspiration/suction, spray, wash, insufflation). These channels may be co-joined with electrical elements, including wiring for lighting, vision, the delivery of energy, or sensing. These endoscopes may include a channel or channel for tools or instruments. This channel may be multi-use, including for aspiration or wash. Any of the endoscopes described herein may include an internal lumen configured as an internal working channel, e.g., for passing one or more accessory devices. Examples of endoscopes may include, but are not limited to colonoscopes, arthroscopes, bronchoscopes, cystoscopes, enteroscopes, esophagogastroduodenoscopes, hysteroscopes, laparoscopes, laryngoscopes, mediastinoscopes, sigmoidoscopes, or thoracoscopes, etc.

The methods and apparatuses described herein may be particularly well suited for manual endoscopes. A manual endoscope may be manually steered using a control (e.g., knob, button, lever, dial, etc.) to steer the distal tip region, and may be advanced or retracted manually. The sheaths described herein may be configured to work on or with a manual endoscope, so that the distal cap may fit over the distal end of the manual endoscope, the external sheath (sealed to the cap) may fit over the outer surface of the endoscope and the one or more internal sheaths (also sealed to the cap) may fit through and line any inner lumen of the endoscope.

The methods and apparatuses described herein may be particularly well suited for use with telescoping system, in which an inner endoscope is concentrically arranged with an outer tube. The inner endoscope and the other endoscope may be moved together (e.g., to advance) and/or separately. All operations of the inner endoscope (also referred to herein as the "child") may be protected by the sheaths described herein and may therefore be reusable a certain number of times, or semi-disposable or resposable (meaning that it is reused a certain number of times, for example 2 to 40 times). In some examples, the outer endoscope tube (which may also be referred to herein equivalently as a "mother," an outer member or as an overtube) may be reusable or may be disposable. The mother may be reusable the same number of times as the child, or it may be reusable a different number of times than the child, or one of the elements may be single use. For example, the outer tube may be completely or partially covered by the external sheath. In variations in which the outer tube is extensively covered by the external sheath (e.g., completely or mostly covered, or covered within the sterile field) the outer tube may be reused after removing the sheath following a procedure. In variations in which the external sheath is connected only distally (e.g., sealed to the distal end or distal end region of the outer tube) the outer tube may be single-use or may require cleaning and/or sterilizing before reuse. Since the outer tube may be easier, faster, and/or cheaper to clean than the endoscope this may still be a net savings. The outer tube may also be an endoscope.

As mentioned, the endoscope may equivalently include (and/or be replaced with) a catheter. In examples including an inner endoscope and an outer tube, the majority of the length of the inner member (equivalently referred to herein as an endoscope, inner endoscope, or "child") may be sheathed by the outer tube, which may be of special construction such that it is referred to as a 'ruggedized' sheath; the distal portion including the external sheath may be a thin film sheath. This can have clinical benefits, e.g., when the endoscope is configured for insertion into the rectum, as the portion that is sliding through the anus for the majority of the procedure may be ruggedized, and sheath wear is minimized, so reliability is increased.

In general, the apparatuses and methods described herein may be used with one or more rigidizing members. In examples including an endoscope, the endoscope may be a rigidizing member, e.g., a selectively rigidizing member. In examples including an endoscope and an outer tube both the inner endoscope and outer tube may be rigidizing members, or just the outer or just the endoscopes may be rigidizing.

For example, described herein are endoscope sheath apparatuses (e.g., systems, devices, etc.) comprising: an external sheath; a cap sealingly coupled to a distal end of the external sheath; and an internal sheath having one or more lumens and extending within the external sheath, wherein the internal sheath is sealingly coupled to the cap so that the one or more lumens are open through the cap.

For example, an endoscope sheath device configured to prevent contamination of an endoscope may include: an external sheath; a cap sealingly coupled to a distal end of the external sheath; and one or more internal sheaths each extending within the external sheath, wherein each internal sheath has one or more internal lumens, further wherein each internal sheath is sealingly coupled to the cap so that the one or more internal lumens is open through the cap.

In some examples an endoscope sheath device configured to prevent contamination of an endoscope may include: a flexible external sheath configured to extend over the endoscope to form an impermeable external barrier; a cap sealingly coupled to a distal end of the external sheath, wherein the cap is configured to mate with a distal end of the endoscope; and one or more internal sheaths each having one or more internal lumens, each of the one or more internal sheaths extending within the flexible external sheath, wherein each of the one or more internal sheaths are configured to pass through a lumen of the endoscope to form an impermeable internal barrier, wherein each of the one or more internal sheaths is sealingly coupled to the cap so that the one or more internal lumens are open through the cap.

Thus, in general the sheath devices (including the cap, outer and internal sheath devices) described herein may form an impermeable contamination barrier. The impermeable contamination barrier may be impermeable to fluid and/or solids. The barrier may be sterile or sterilized. Optionally the barrier does not have to be sterile, but may be clean and may prevent contamination of the endoscope to which it is attached. The endoscope does not need to be sterile or remain sterile, but may be kept clean and free of contaminants by the sheath devices described herein. In particular both external and internal (e.g., channels, lumen, etc.) of the endoscope may be kept clean and free of contaminant as the sheath devices described herein may effectively generate a barrier to prevent contamination. Importantly, these sheath devices are configured to be removed without contamination of the endoscope covered by the sheath, either externally or internally.

An endoscope sheath device configured to prevent contamination of an endoscope may include: a flexible external sheath configured to fit over the endoscope; a cap sealingly coupled to a distal end of the external sheath; one or more internal sheaths each extending within the external sheath and configured to fit within a lumen extending through the endoscope, wherein each internal sheath has one or more internal lumens, further wherein each internal sheath is sealingly coupled to the cap so that the one or more internal lumens is open through the cap; and a sealing region at a proximal end of each of the one or more internal sheaths that is configured to be sealed after use to prevent contamination during removal of the one or more internal sheaths from within the lumen extending through the endoscope.

For example, in some examples, the external sheath comprises a flexible, thin, resilient material. The external sheath may be comprised of one or more materials, including plastics, elastomers, plastomers, or composite materials. Plastomers include polymer materials which combine qualities of elastomers and plastics, such as rubber-like properties with the processing ability of plastic. Plastomers may include ethylene-alpha olefin copolymers. Appropriate materials may include latex, polyvinylchloride, polyurethane, polyethylene, polypropylene, silicone, or other similar materials. The material may be reinforced through lamination, including with fibers or metals. In some examples the distal end (e.g., distal 10% or more, distal 15% or more, distal 20% or more, distal 25% or more, distal 30% or more, distal 35% or more, etc.) of the external sheath may be a thin-walled sheath, while the rest of the external sheath may be ruggedized. A ruggedized sheath may be thicker (e.g. having a wall thickness of 0.1 mm or greater, 0.2 mm or greater, 0.25 mm or greater, 0.3 mm or greater, 0.35 mm or greater, 0.4 mm or greater, 0.5 mm or greater, 0.55 mm or greater, 0.6 mm or greater, 0.7 mm or greater, 0.8 mm or greater, 0.9 mm or greater, 1 mm or greater, etc.). Depending on the material forming the sheath, a thin-walled sheath may have a thickness of, e.g., 0.2 mm or thinner, 0.15 mm or thinner, 0.1 mm or thinner, 0.05 mm or thinner, 0.04 mm or thinner, 0.02 mm or thinner, between about 0.25 mm to 0.01 mm thick, between about 0.2 mm to 0.02 mm thick, etc.). The sheath may be formed of a single material having different regions (e.g., thin-walled region and thicker-walled or ruggedized region) or a sheath may be formed of different materials that are coupled (e.g., fused, sealed, etc.) together.

In general, the external sheath may be shorter than the internal sheath. For example, the external sheath may extend just to the tip of an elongate outer tube (e.g., an elongate outer tube); in some examples the external sheath may extend along the length of the elongate outer tube.

The cap may be polymeric material that may be transparent and/or may include a transparent window configured to align with a camera of an endoscope to allow imaging therethrough. The cap may be configured to couple to a distal end of an endoscope. In some examples the cap is configured to secure to a distal end of an endoscope. For example, there are multiple methods that could be used to attach the cap. Examples may include one or more of: a shear surface configured to secure the cap to the distal end of the endoscope, a snap fit configured to secure the cap to the distal end of the endoscope, a magnet configured to secure the cap to the distal end of the endoscope, a bayonet connector configured to secure the cap to the distal end of the endoscope, or a threaded region configured to secure the cap to the distal end of the endoscope.

In any of the apparatuses described herein the external sheath may have a lower buckling resistance than the internal sheath(s). Thus, the internal sheath(s) may have a higher axial compression stiffness than the external sheath; the external sheath may be configured to buckle (e.g., to scrunch, pleat, gather, stack up on itself, etc.) whereas the internal sheath(s) are configured to resist buckling. In some examples the internal sheath comprises a multi-lumen catheter. For example, the internal sheath may be formed as an elongate, flexible single-lumen or multi-lumen catheter. The internal sheath may be formed of a polymeric material such as polyvinylchloride, polyurethane, polyethylene, polypropylene, etc. The internal sheath(s) may be a composite structure, including wire or fiber reinforced. The internal sheath(s) may have elements to facilitate sliding (either along its inside surface or along its outer surface), during install, during use (including allowing tools to pass), and during un-install/removal. The constituents of the internal sheath may vary along its length, including material and/or durometer. In general, the internal sheath may also be referred to as an internal sheath and may be longer than the endoscope into which it is to be inserted so that the internal sheath extends proximally from the endoscope where it may engage with a port adapter (also referred to equivalently herein as a port adapter manifold) to provide access into or out of the lumen (or lumens) of the internal sheath.

For example, when the internal sheath has multiple lumens (e.g., is configured as a multi-lumen catheter), the proximal end of the internal sheath may include one or more openings into an internal lumen of the one or more lumens at a proximal end region of the internal sheath. For example, this could be end openings and/or side openings. In some examples, the internal sheath includes a plurality of radially spaced-apart (and optionally laterally or axially spaced-apart) side openings at a proximal end region of the internal sheath, wherein each radially spaced-apart side openings open into a lumen of the multi-lumen catheter. The port adapter may couple to the end of the inner lumen (e.g., the multi-lumen catheter) to align the opening(s) of the internal sheath with ports or directly with a source of suction, pressurized air ('insufflation'), a source fluid (e.g., saline), etc. In general, a port adapter may be configured to couple with the multi-lumen catheter to create isolated ports in fluid connection with each lumen of the multi-lumen catheter. The internal sheath, therefore, despite being a disposable component that may be thin and small and with multiple lumens, can be quickly, easily, and accurately attached, retained, (and subsequently detached) to a structure such as a port adapter that can readily plumb to a multitude of inputs. This adaption with the port adapter can work with single lumen internal sheaths, and with multiple lumen internal sheaths.

Any of these apparatuses may include multiple internal sheaths. In some examples, the apparatus includes a second internal sheath configured as a working channel liner. The working channel liner may have a working channel lumen and extend within the external sheath adjacent to the internal sheath, wherein the working channel liner is sealingly coupled to the cap so that the working channel lumen is open through the cap. A working channel may include a single lumen and may permit one or more tools to enter proximally and then exit distally. The working channel may be used for suction or for irrigation.

Both the external sheath and the one or more internal sheaths may be sealingly attached to the cap to prevent a barrier to fluid and/or microorganisms preventing access to the endoscope. In some examples the external sheath and/or the internal sheath (including a working channel lumen) may be coupled to the cap with a weld, an ultrasonic weld, and/or an adhesive to form the sealing attachment.

Any of these apparatuses may include a proximal attachment on the external sheath configured to secure the external sheath to an outer surface of an endoscope. The proximal attachment may be an elastic material that may elastically attach or secure the external sheath to the outer surface of the endoscope. In some examples the proximal attachment may comprise a sealing attachment (e.g., a gasket, such as but not limited to an O-ring; an adhesive material; etc.). In general, the proximal attachment for the external sheath may hold the external sheath over the endoscope and/or against the endoscope (in examples in which the sheath is used with a single endoscope by itself) or against an elongate outer tube (in examples in which the sheath is used with a telescoping assembly including an elongate outer tube and an inner endoscope that are coaxially arranged).

After the internal sheath has been used, it must be withdrawn so that it can be disposed of, such that the endoscope is ready for a fresh and new sheath system. Given that contaminated fluids have passed through the internal sheath, the internal sheath should be cleanly and effectively terminated, so that it does not present a contamination risk. To do so, the internal sheath can be crimped, including with a metal tube that is radially compressed. It could be sealed with an adhesive that cures (for example, with UV curing). It could be heat sealed, such that the lumen is effectively sealed and terminated. The diameter of the sealed unit must be no larger than that of the lumen through which it will be pulled, or otherwise it would not be removeable. In any of these examples, once the one or more internal sheaths are sealed, it/they may be cut while still remaining contaminant-free—with a short portion staying behind in the port adapter, and the long portion subsequently sliding out distally. These methods may seal off the internal sheath to prevent contamination when removing the endoscope sheath device from an endoscope.

For example, described herein are endoscope sheath devices comprising: a flexible external sheath; a cap sealingly coupled to a distal end of the flexible external sheath, wherein the cap is configured to be sealed to a distal end of an endoscope; an internal sheath having one or more lumens and extending within the flexible external sheath, wherein the internal sheath is sealingly coupled to the cap so that the one or more lumens are open through the cap; and a working channel liner (e.g., a second internal sheath) having a working channel lumen and extending within the flexible external sheath adjacent to the internal sheath, wherein the working channel liner is sealingly coupled to the cap so that the working channel lumen is open through the cap.

Any of the apparatuses described herein may be configured as a sheath assembly including the sheath components described above, e.g., external sheath, internal sheath(s) and cap integrated with an outer tube of a telescoping arrangement (e.g., an outer catheter, overtube, or other outer elongate member having an inner lumen into which the endoscope may be positioned). For example the external sheath may be fused or otherwise connected (including sealingly connected) to the outer surface of the elongate outer tube to form the sheath assembly. Multiple such sheath assemblies may be used with the same endoscope so that it may be attached and removed without dirtying or compromising the cleanliness of the endoscope, as described herein.

For example, described herein are systems comprising a flexible outer tube for use with an inner endoscope in a telescoping arrangement, the system comprising: an elongate outer tube, the elongate outer tube comprising an outer tube lumen; an external sheath coupled to a proximal end region of the elongate outer tube at a first end region; a cap sealingly coupled to a second end of the external sheath; and an internal sheath having one or more internal sheath lumen and extending within the external sheath and within the outer tube lumen, wherein the internal sheath is sealingly coupled to the cap so that the one or more internal sheath lumen are open through the cap.

These systems may include any of the features described above. Further, the cap may be configured to couple to a distal end of the inner endoscope and the internal sheath may be configured to extend through a lumen of the inner endoscope. As mentioned, in general the sheath apparatuses described herein may be used with non-rigidizing members, as well as rigidizing members (e.g., rigidizing endoscopes, catheters, and/or overtubes). For example, the elongate outer tube may be configured to be selectively rigidized. The elongate outer tube may be configured to be selectively rigidized by multiple techniques, including the application of positive pressure or negative pressure. Devices may be robotically operated, or they may be manually operated.

Also described herein are methods of using any of these apparatuses, which may include methods of applying and/or removing the sheaths from the endoscope or assemblies (e.g., telescoping assemblies) including endoscopes, and methods of keeping an endoscope clean using the sheath apparatus. For example, a method of attaching a sanitary sheath to an endoscope may include: inserting an internal sheath through a lumen of the endoscope from a distal end to a proximal end so that one or more internal sheath lumen extend through the endoscope from the distal end to the proximal end; positioning an external sheath over the endoscope so that the external sheath extends proximally from the distal end; and securing a cap to the distal end of the endoscope, wherein the external sheath is sealingly connected to the cap and the internal sheath is sealingly connected to the cap so that the internal sheath lumen are open through the cap.

Positioning the external sheath over the endoscope may include positioning the endoscope within an elongate outer tube so that the endoscope may move telescopically relative to the elongate outer tube. Inserting the internal sheath through the lumen of the endoscope may comprise inserting a multi-lumen catheter forming the internal sheath through the lumen of the endoscope.

Once positioned, in some examples these methods may include coupling the internal sheath to a port adapter at a proximal end region of the internal sheath. Any of these methods may include coupling each of the lumen of the multi-lumen catheter to a port adapter at a proximal end region of the internal sheath to provide isolated access to each lumen.

The proximal end of the flexible outer tube may be connected, including to the base of an endoscope (for a manual procedure) or to mating geometry on a capital base (for a robotic procedure). Once the procedure is completed, this feature may then be disconnected or disengaged.

In some examples attaching the cap to the distal end of the endoscope comprises securing the cap to the distal end of the endoscope using one or more of: a snap fit, a friction fit, a magnet coupler, a bayonet connector or a threaded region.

For example, a method of maintaining cleanliness of an endoscope may include: performing a medical procedure with an endoscope, such that a distal end of the endoscope is covered by a cap, wherein an internal sheath that is sealingly connected to the cap extends through a lumen of the endoscope from a distal end to a proximal end so that one or more internal sheath lumen extends through the lumen of the endoscope and are open through the cap, further wherein an external sheath is sealingly connected to the cap and extends proximally over the endoscope and connects to lumens at the proximal end; removing the cap from the distal end of the endoscope; and withdrawing the endoscope proximally out of the external sheath so that the internal sheath is extended out of the distal end of the lumen of the endoscope, wherein a proximal end region of the internal sheath has been sealed closed.

Performing the medical procedure may comprise passing material into or out of the one or more internal sheath lumen through the cap and/or imaging through the cap (e.g., through an imaging window and/or through a transparent cap or region of the cap). The external sheath may be coupled to an outer surface of an outer tube and the endoscope is telescopically arranged within the outer tube. Performing the medical procedure may comprise moving the endoscope proximally or distally relative to the outer tube. In any of these apparatuses, withdrawing the endoscope proximally out of the external sheath may comprise withdrawing the endoscope proximally from the outer tube.

Any of these methods may include sealing the proximal end region of the internal sheath. For example, sealing the proximal end region may comprise crimping the proximal end region. Sealing the proximal end region may comprise heat-sealing the proximal end region.

Any of the apparatuses (e.g., devices) described herein may include an internal sheath that is a multi-lumen extrusion (e.g., a multi-lumen catheter) having 2 or more sub-lumen (e.g., 3 lumen, 4 lumen, etc.). An internal sheath comprising a multi-lumen catheter may be used to convert a single lumen of an endoscope into multiple separate lumen. Apparatuses, e.g., devices, including multi-lumen internal sheaths may be used to deliver a variety of different things, such as suction, insufflation, rinse solution, etc. These apparatuses may be adapted for use with a port adapter that may provide reliable access to the different lumen of the multi-lumen internal sheath. For example, an endoscope sheath device configured to prevent contamination of an endoscope may include: an external sheath; a cap sealingly coupled to a distal end of the external sheath; and an internal sheath comprising a multi-lumen catheter extending within the external sheath, wherein the internal sheath is sealingly coupled to the cap so that the lumen of the multi-lumen catheter are open through the cap; and a plurality of radially spaced-apart side openings at a proximal end region of the internal sheath, wherein each side opening opens into an internal lumen of the multi-lumen catheter. The proximal end region of the internal sheath may be configured to mate with a port adapter to create isolated ports in fluid connection with each lumen of the multi-lumen catheter.

For example, a method of attaching a sanitary sheath to an endoscope may include: inserting an internal sheath through a lumen of the endoscope from a distal end to a proximal end so that one or more internal sheath lumen extends through the endoscope from the distal end to the proximal end; positioning an external sheath over the endoscope so that the external sheath extends proximally from the distal end; and attaching a cap to the distal end of the endoscope, wherein the external sheath is sealingly connected to the cap and the internal sheath is sealingly connected to the cap so that the internal sheath lumen is open through the cap.

The internal sheath comprises a multi-lumen catheter and wherein inserting the internal sheath through the lumen of the endoscope comprises inserting the multi-lumen catheter through the lumen of the endoscope. The internal sheath may include a working channel liner and wherein inserting the internal sheath through the lumen of the endoscope comprises inserting the working channel liner through the lumen of the endoscope. Any of these methods may include inserting a second internal sheath through a second lumen of the endoscope from the distal end to the proximal end so that an internal sheath lumen of the second internal sheath extends through the endoscope from the distal end to the proximal end. The internal sheath may include a multi-lumen catheter and further comprising coupling the internal sheath to a port adapter at a distal end region of the internal sheath to create isolated ports in fluid connection with each lumen of the multi-lumen catheter.

Attaching the cap to the distal end of the endoscope may include securing the cap to the distal end of the endoscope using one or more of: a snap fit, a friction fit, a magnet coupler, a bayonet connector or a threaded region. Attaching the cap to the distal end of the endoscope may comprise manually compressing (e.g., using two or more fingers to compress) a cylindrical mating surface of the cap that is configured to mate with a distal end of the endoscope from an oval resting cross-sectional configuration into a circular mating cross-sectional configuration.

Positioning the external sheath over the endoscope may include positioning the endoscope within an elongate outer tube so that the endoscope may move telescopically relative to the elongate outer tube.

For example, a method of maintaining cleanliness of an endoscope may include: performing a medical procedure with an endoscope while a distal end of the endoscope is covered by a cap, wherein an internal sheath that is sealingly connected to the cap extends through a lumen of the endoscope from a distal end to a proximal end and so that one or more internal sheath lumen extends through the lumen of the endoscope and are open through the cap, further wherein an external sheath is sealingly connected to the cap and extends proximally over the endoscope; removing the cap from the distal end of the endoscope; and withdrawing the endoscope proximally out of the external sheath so that the internal sheath is extended out of the distal end of the lumen of the endoscope, wherein a proximal end region of the internal sheath has been sealed closed. Performing the medical procedure may include passing material into or out of the one or more internal sheath lumen through the cap. Performing the medical procedure may include imaging through the cap (e.g., a lens on the cap). The external sheath may be coupled to an outer surface of an outer tube and the endoscope is telescopically arranged within the outer tube.

Performing the medical procedure may comprise moving the endoscope proximally or distally relative to the outer tube. Withdrawing the endoscope proximally out of the external sheath may include withdrawing the endoscope proximally from the outer tube. As mentioned, any of these methods may include sealing the proximal end region of the internal sheath. For example, sealing the proximal end region may comprise crimping the proximal end region. In some examples sealing the proximal end region comprises heat-sealing the proximal end region.

As mentioned above, any of these apparatuses (e.g., sheaths) may be configured to include a crimping region at a proximal end region of the internal sheath that is configured to be crimped to seal the one or more lumens after use to prevent contamination during removal of the internal sheath from within a lumen of the endoscope. The crimping region may include a region that is formed of material (e.g., a metallic material, such as a cuff or link region) that is able to hold a crimp without leaking. In some examples the crimping region may be configured to melt. For example, the crimping region may be configured to be heat sealed and/or pressure sealed. The crimping region may be formed of or supplemented with a different material than the reasons proximal and/or distal to the crimping region. As used herein crimping may include both mechanical crimping (e.g., pinching off of the lumen) as well as thermal crimping (e.g., heating/melting the lumen so that it closes), or some combination of these. Crimping may deform the material forming the lumen and/or an additional material on or around the lumen.

For example, an endoscope sheath device configured to prevent contamination of an endoscope may include: a flexible external sheath; a cap sealingly coupled to a distal end of the external sheath; and an internal sheath comprising a multi-lumen catheter extending within the external sheath, wherein the internal sheath is sealingly coupled to the cap so that the lumen of the multi-lumen catheter are open through the cap, further wherein the internal sheath is less flexible than the external sheath and is configured to extend through a lumen of the endoscope; and a plurality of radially and/or axially spaced-apart side openings at a proximal end region of the internal sheath, wherein each side opening opens into an internal lumen of the multi-lumen catheter, further wherein the proximal end region of the internal sheath is configured to mate with a port adapter to create isolated ports in fluid connection with each lumen of the multi-lumen catheter.

An endoscope sheath device configured to prevent contamination of an endoscope may include: a flexible external sheath configured to extend over the endoscope; a cap sealingly coupled to a distal end of the external sheath; and an internal sheath comprising a multi-lumen catheter extending within the external sheath, wherein the internal sheath is sealingly coupled to the cap so that the lumen of the multi-lumen catheter are open through the cap, further wherein the internal sheath is configured to extend through a lumen of the endoscope; a plurality of radially and/or axially spaced-apart side openings at a proximal end region of the internal sheath, wherein each side opening opens into an internal lumen of the multi-lumen catheter; and a crimping region at a proximal end region of the internal sheath that is configured to be crimped to seal the one or more lumens after use to prevent contamination during removal of the internal sheath from within the lumen of the endoscope.

Any of the endoscope sheath devices described herein (or method of making and using them and/or system including them) may be configured to prevent contamination of an endoscope and may include: an external sheath; a cap sealingly coupled to a distal end of the external sheath; and an internal sheath comprising a multi-lumen catheter extending within the external sheath, wherein the internal sheath is sealingly coupled to the cap so that the lumen of the multi-lumen catheter are open through the cap; and a sealing region at a proximal end region of the internal sheath that is configured to seal the lumen of the multi-lumen catheter after use to prevent contamination during removal of the internal sheath from within a lumen of the endoscope. As mentioned, any of these methods may include a plurality of radially spaced-apart side openings at a proximal end region of the internal sheath, wherein each side opening opens into an internal lumen of the multi-lumen catheter. The proximal end region of the internal sheath may be configured to mate with a port adapter to create isolated ports in fluid connection with each lumen of the multi-lumen catheter. The sealing region may comprise a crimping region (e.g., a mechanical sealing/crimping region) configured to be mechanically crimped. Thus, the sealing region may be configured to be pressure sealed. The sealing region may be configured to be heat sealed.

For example, an endoscope sheath device configured to prevent contamination of an endoscope, may include: a flexible external sheath; a cap sealingly coupled to a distal end of the external sheath; and an internal sheath comprising a multi-lumen catheter extending within the external sheath, wherein the internal sheath is sealingly coupled to the cap so that the lumen of the multi-lumen catheter are open through the cap, further wherein the internal sheath is configured to extend through a lumen of the endoscope; and a crimping region at a proximal end region of the internal sheath that is configured to be crimped to seal the one or more lumens after use to prevent contamination during removal of the internal sheath from within the lumen of the endoscope.

An endoscope sheath device configured to prevent contamination of an endoscope may include: a flexible external sheath configured to extend over the endoscope; a cap sealingly coupled to a distal end of the external sheath; and an internal sheath comprising a multi-lumen catheter extending within the external sheath, wherein the internal sheath is sealingly coupled to the cap so that the lumen of the multi-lumen catheter are open through the cap, further wherein the internal sheath is configured to extend through a lumen of the endoscope; a plurality of radially spaced-apart side openings at a proximal end region of the internal sheath, wherein each side opening opens into an internal lumen of the multi-lumen catheter; and a crimping region at a proximal end region of the internal sheath that is configured to be crimped to seal the one or more lumens after use to prevent contamination during removal of the internal sheath from within the lumen of the endoscope.

Also described herein are methods of making any of the endoscope sheaths described herein. For example, a method of making an endoscope sheath device configured to prevent contamination of an endoscope may include: sealing a distal end region of a tubular internal sheath to an opening through a cap that is configured to couple to a distal end region of the endoscope, wherein the tubular internal sheath is configured to be inserted through a lumen of the endoscope; and sealing a distal end region of a tubular external sheath to the cap, wherein the tubular external sheath is configured to fit over an outer surface of the endoscope. In general a tubular external sheath and/or a tubular internal sheath may have any cross-sectional shape, not limited to circular or oval (e.g., square, triangular, octagonal, etc.).

Any of these methods may include coating the inside (and in some examples the outside) of the internal sheath or sheaths with a hydrophilic coating, as any of these apparatuses may include an internal sheath with a hydrophilic coating on the inside of the full length of the internal sheath and/or on the outside of the internal sheath. In some examples, the method may include coating a sheet of an internal sheath material with a hydrophilic coating and forming the sheet of internal sheath material into a tube to form the tubular internal sheath so that the hydrophilic coating extends within a lumen of the tubular internal sheath. In some examples the hydrophilic coating is applied as an additive to a matrix material. The internal sheath with the coating may be a single-lumen sheath (e.g., a working channel liner) or a multi-lumen sheath. For example, any of these methods may include sealing a distal end region of a second tubular internal sheath to a second opening through the cap, wherein the second tubular internal sheath comprises a multi-lumen tube. In some examples the tubular internal sheath may comprise a working channel liner having a working channel lumen.

Any of the apparatuses (e.g., sheaths) described herein may include a reinforced internal sheath or sheaths, in particular at the distal end regions of the internal sheath(s). This may be particularly helpful in variations in which the distal end region (e.g., the distal tip region) of the catheter is configured to be bent, steered, etc. Thus, it may be beneficial to provide an apparatus having a reinforced distal end region (or all of the length of the endoscope or just the distal end region, such as the distal 5 cm, distal 4 cm, distal 3 cm, distal 2 cm, distal 1 cm, etc. Reinforcing the distal end region of the single-lumen internal sheaths (e.g., working channel liner) may be particularly helpful to prevent pinching closed at the bending distal end region. Thus, any of the methods of forming the apparatuses described herein may also include reinforcing the tubular internal sheath so that the distal end region of the tubular internal sheath is prevented from collapse when bending.

In any of these examples the internal sheath may include a reinforcing structure such as a reinforcing coil; thus the method of forming the apparatus may include adding a reinforcing coil. In some example the method may include adding a reinforcing just the distal end region (e.g., just to the distal 5 cm, distal 4 cm, distal 3 cm, distal 2 cm, distal 1.5 cm, distal 1 cm, etc.).

In any of these methods sealing the distal end region of the tubular internal sheath to the cap and sealing the distal end region of the tubular external sheath may comprise forming a continuous fluid-impermeable contamination barrier.

Any of these methods may include packaging the endoscope sheath device in a coiled configuration. This configuration may make it easier to store and apply the sheath device onto an endoscope, including taking up less space and less landfill, and reducing any necessary sterilization costs.

Any of these methods may include forming a crimping region at a proximal end region of the internal sheath (or each of the sheaths in variations with multiple sheaths) that is configured to be crimped to seal the one or more lumens after use to prevent contamination during removal of the internal sheath from within a lumen of the endoscope. In some examples, the crimping region may include a cuff or ring formed of a relatively ductile material, such as a metal, that may be pinched closed to seal the one or more lumens of the internal sheath(s). In some example, the internal sheath may include a region formed of a material that may be crimped as described herein.

The methods of forming the devices described herein may also include ruggedizing the tubular external sheath. The tubular external sheath may be formed to be shorter than the tubular internal sheath (e.g., the internal sheath(s) may extend beyond the tubular external sheath). The devices described herein may be formed using any of the caps described herein, including caps that are all or partially transparent. The cap may include a cylindrical mating surface having an oval configuration at rest, wherein the cylindrical mating surface is configured to be compressed to assume a circular cross-sectional configuration to fit over a distal end of an endoscope. Any of these methods may include attaching a proximal attachment on the tubular external sheath that is configured to secure the tubular external sheath to an outer surface of the endoscope.

For example, a method of making an endoscope sheath device configured to prevent contamination of an endoscope may include: coating a layer of an internal sheath material with a hydrophilic coating and laminating the internal sheath material into a tubular internal sheath so that the hydrophilic coating extends within a lumen of the tubular internal sheath; sealing a distal end region of the tubular internal sheath to an opening through a cap that is configured to couple to a distal end region of the endoscope, wherein the tubular internal sheath is configured to be inserted through a lumen of the endoscope; and sealing a distal end region of a tubular external sheath to the cap, wherein the tubular external sheath is configured to fit over an outer surface of the endoscope, wherein the tubular external sheath, the cap and the tubular internal sheath form a continuous fluid-impermeable contamination barrier.

For example, a method of making an endoscope sheath device configured to prevent contamination of an endoscope may include: reinforcing a tubular internal sheath, including with a higher density of reinforcement distally so that a distal end region of the tubular internal sheath is prevented from collapse when bending; sealing a distal end region of the internal sheath to an opening through a cap that is configured to couple to a distal end region of the endoscope, wherein the internal sheath is configured to be inserted through a lumen of the endoscope; and sealing a distal end region of a tubular external sheath to the cap, wherein the external sheath is configured to fit over an outer surface of the endoscope, wherein the external sheath, cap and internal sheath form a continuous fluid-impermeable contamination barrier.

As mentioned above, any of these sheath apparatuses may include a distal cap configured to couple to the endoscope that that include one or more light sources. These light sources may be light emitting diodes (LEDs), fiber optics, laser light sources, etc. For example, described herein are endoscope sheath devices configured to prevent contamination of an endoscope that include: an external sheath; a cap sealingly coupled to a distal end of the external sheath, wherein the cap is at least partially transparent and configured to couple to a distal end of the endoscope; (optionally) one or more internal sheaths each extending within the external sheath, wherein each internal sheath has one or more internal lumens, further wherein each internal sheath is sealingly coupled to the cap so that the one or more internal lumens is open through the cap; and one or more light sources on the cap configured to project light distally of the cap.

In some examples the one or more light sources comprises a light-emitting diode (LED). For example, the one or more light sources may include a red light source, a green light source and a blue light source. The apparatus may be configured to apply white light, e.g., by illuminating each of the red, green and blue, light sources, and/or applying a specific wavelength or range of wavelengths (e.g., red or green or blue) to interrogate the anatomy differentially using different wavelengths of light. The one or more light sources may include a plurality of light sources arranged at least partially around a perimeter of the cap. The light sources may be arranged around the full perimeter or portion of the perimeter. In some examples the apparatus may include a plurality of conductive members (e.g., traces, wires, etc.) coupled to the one or more light sources on the cap and extending on or in the external sheath or on or in the internal sheath. For example, wires may extend helically around the external sheath to couple with a control and/or power on the proximal end of the device.

In some examples the apparatus includes one or more electrical contacts on an inner surface of the cap, wherein the one or more electrical contacts are in electrical communication with the one or more light sources. The electrical contacts may be on an inner surface of the cap and may be pads or pins that contact pins or pads on the distal end region of the endoscope.

In general, the cap may include a lensing region configured to be positioned over a camera of the endoscope. The lensing region may be formed in the cap (of the cap material) and/or it may include an additional material added to the cap. The lensing region may be a lens formed as a concave and/or convex region. The lensing region may expand the field of view.

In general, the cap is configured to be secured to the distal end of the catheter. For example, the cap may include one or more of: a friction fitting configured to secure the cap to the distal end of the endoscope, a snap fit configured to secure the cap to the distal end of the endoscope, a magnet configured to secure the cap to the distal end of the endoscope, a bayonet connector configured to secure the cap to the distal end of the endoscope, or a threaded region configured to secure the cap to the distal end of the endoscope. In some examples the cap may include a cylindrical engagement region that fits over the endoscope and may include one or more latches.

For example, described herein are endoscope sheath devices configured to prevent contamination of an endoscope, the device comprising: a flexible and tubular external sheath; a cap sealingly coupled to a distal end of the external sheath, wherein the cap is at least partially transparent; a tubular elongate internal sheath extending within the external sheath and having one or more internal lumens, further wherein a distal end region of the tubular elongate internal sheath is sealingly coupled to the cap so that the one or more internal lumens of the tubular elongate sheath is open through the cap; and one or more light sources on the cap configured to project light distally of the cap.

An endoscope sheath device configured to prevent contamination of an endoscope may include: a flexible and tubular external sheath; a cap sealingly coupled to a distal end of the external sheath, wherein the cap is at least partially transparent; a tubular elongate internal sheath extending within the external sheath and having one or more internal lumens, further wherein a distal end region of the tubular elongate internal sheath is sealingly coupled to the cap so that the one or more internal lumens of the tubular elongate sheath is open through the cap; one or more light sources on the cap configured to project light distally of the cap; and one or more electrical contacts on an inner surface of the cap, wherein the one or more electrical contacts are in electrical communication with the one or more light sources.

Any of the sheath apparatuses described herein may be configured as rigidizing sheaths. For example, described herein are rigidizing sheaths in which the external sheath is rigidizing and may be transitioned from a flexible configuration to a rigid configuration, e.g., by the application of pressure; in some examples positive pressure may be applied, in some examples negative pressure may be applied, and in some examples either positive or negative pressure may be applied.

The rigidizing sheath devices described herein can transition from a flexible configuration to a rigid configuration. In some examples, e.g., based on the pressure applied, the rigidity (e.g., the stiffness) may be considered "variable stiffness" as it may be selected by the user or system. For example, a rigidizing external sheath may be rigidized by applying a positive or negative pressure to rigidize a rigidizing layer within the rigidizing external sheath by driving a compression layer (e.g., bladder) against a rigidizing layer, preventing or limiting movement of the rigidizing layer. With the positive or negative pressure removed (or reversed), the layers can easily shear or move relative to each other; the release of the positive or negative pressure may allow the layers to transition to a condition in which they exhibit a substantially enhanced ability to resist shear, movement, bending, torque and buckling, thereby providing system rigidization. Although the examples described herein primarily illustrate rigidizing by the application of pressure (e.g., positive or negative pressure), the methods and apparatuses described herein may be used with any appropriate rigidizable sheath(s), not limited to positive or negative pressure rigidizing apparatuses. For example, the rigidizable sheath as described herein may refer to any appropriate rigidizing sheath, including sheaths that may be rigidized by jamming particles, by phase change and/or shape memory alloys, by interlocking components (e.g., cables with discs or cones, etc.), EAP (electro-active polymers) or any other rigidizing mechanism.

Any of the rigidizable sheaths described herein may include rigidizing layers or regions that engage with a compression layer (which may be or may include a bladder) that applies force to the rigidizing layer to rigidize the rigidizing layer or in some cases to de-rigidize (e.g., release from rigidization) the rigidizing layer. In some examples, these rigidizable apparatuses may include a rigidizing layer that could include a braid, knit, woven, chopped segments, randomly distributed or randomly oriented filaments or strands, engagers, links, scales, plates, segments, particles, granules, crossing filaments, or other materials forming the rigidizing layer. For example, the rigidizing layer may comprise multiple strand lengths or strand segments that cross over each other (e.g., as part of a braid, knit, woven, etc.); the compression layer may apply force to drive the crossing strand lengths or strand segments against each other. Although many of the examples shown herein are braids, any of these apparatuses may instead or in addition include a general rigidizing layer comprising crossing strand lengths or strand segments. The examples of rigidizing apparatuses described herein may use pressure (positive pressure) and/or negative pressure to selectively and controllable rigidize. In some examples the method described herein may be used with any appropriate rigidizing apparatus. Examples of rigidizing structures that may be included as part of a rigidizing sheath may include those described in PCT application PCTUS2023064999, filed Mar. 27, 2023 and titled "METHODS AND APPARATUSES FOR NAVIGATING USING A PAIR OF RIGIDIZING DEVICES," U.S. patent application Ser. No. 17/902,770, titled "NESTED RIGIDIZING DEVICES," filed on Sep. 8, 2022, U.S. patent application Ser. No. 18/000,062, titled "RIGIDIZING DEVICES," filed on May 26, 2021, patent application no. PCTUS2022014497, titled, "DEVICES AND METHODS TO PREVENT INADVERTENT MOTION OF DYNAMICALLY RIGIDIZING DEVICES," filed on Jan. 31, 2022, patent application no. PCTUS2022082300, titled "METHODS AND APPARATUSES FOR REDUCING CURVATURE OF A COLON," filed on Dec. 22, 2022, patent application no. PCTUS2023062206, titled "DYNAMICALLY RIGIDIZING COMPOSITE MEDICAL STRUCTURES," filed on Feb. 8, 2023. Each of these applications are herein incorporated by reference in their entirety.

For example, an endoscope sheath device configured to prevent contamination of an endoscope may include: a rigidizing external sheath configured to extend over the endoscope, the rigidizing external sheath including: a rigidizing layer comprising multiple strand lengths that cross over each other, and a compression layer that is configured to be actuated to apply force to the rigidizing layer to rigidize the rigidizing external sheath from a flexible configuration to a rigid configuration; a cap configured to couple to a distal end of the endoscope, wherein the cap is sealingly coupled to a distal end region of the external sheath; an internal sheath extending within the rigidizing external sheath and configured to extend through a lumen of the endoscope, wherein the internal sheath has one or more internal lumens and is sealingly coupled to the cap so that the one or more internal lumens of the internal sheath is open through the cap.

As mentioned, in some examples, the rigidizing layer may include multiple strand lengths that cross over each other. The multiple strand lengths may comprise one or more of: a braid, a knit, a weave, chopped segments, randomly distributed and/or randomly oriented filaments, or engagers. The compression layer may comprise a bladder. The internal sheath may be less flexible than the flexible configuration of the rigidizing external sheath. Any of these apparatuses may include a pressure port coupled to the rigidizing external sheath and configured to receive pressure to actuate the compression layer. The rigidizing external sheath may be configured to rigidizing by the application of positive pressure. The rigidizing external sheath may be configured to rigidizing by the application of negative pressure.

For example, an endoscope sheath device configured to prevent contamination of an endoscope, may include: a rigidizing external sheath configured to extend over the endoscope, the rigidizing external sheath including: a rigidizing layer comprising multiple strand lengths that cross over each other, and a compression layer that is configured to be actuated to apply force to the rigidizing layer to rigidize the rigidizing external sheath from a flexible configuration to a rigid configuration; a cap sealingly coupled to a distal end region of the external sheath and configured to engage a distal end of the endoscope; and an internal sheath extending within the rigidizing external sheath and configured to extend through a lumen of the endoscope, wherein the internal sheath has one or more internal lumens and is sealingly coupled to the cap so that the one or more internal lumens of the internal sheath is open through the cap.

Any of the apparatuses described herein may be configured to be reinforced, and in particular the internal sheath(s) may be reinformed at their distal ends, in order to prevent pinching of the one or more lumens of the tubular internal sheath(s). Endoscopes may be steerable and may therefore bend at their distal end region. Thus, the sheath apparatuses described herein may be configured to prevent, reduce or minimize the impact of the internal sheath(s) on the overall flexibility, and therefore steering, of the distal ends of the apparatuses. In some examples the internal sheath(s) may be configured to be relatively flexible. However, these internal sheaths may also be configured to resist pinching of the lumen when bending or flexing, which may otherwise occur with highly flexible structures. For example, the internal sheaths described herein may be reinforced, e.g., by a reinforcing coil, etc., to prevent collapse while maintaining a high degree of flexibility.

For example, an endoscope sheath device configured to prevent contamination of an endoscope may include: a cap configured to couple to a distal end of the endoscope; a flexible external sheath configured to extend over the endoscope, wherein a distal end region of the external sheath is sealingly coupled to the cap; and a tubular internal sheath configured to be inserted through a lumen of the endoscope, the tubular internal sheath extending proximally from the cap and within the external sheath, wherein a distal end region of the tubular internal sheath is sealingly coupled to the cap so that a lumen of the tubular internal sheath is open through the cap, further wherein the distal end region is of the tubular internal sheath is reinforced to prevent the tubular internal sheath from collapsing when bending.

The distal end region of the tubular internal sheath may comprise a reinforcing coil. In some examples just the distal end region of the tubular internal sheath is reinforced; alternatively the majority (or all) of the length of the internal sheath may be reinforced. In some examples, where multiple internal sheaths are used, only those internal sheaths having a single lumen (e.g., a working channel liner) are reinforced as described herein. For example, any of these apparatuses may include a second tubular internal sheath sealingly coupled to the cap and configured to be inserted through a lumen of the endoscope, the second tubular internal sheath extending proximally from the cap and within the external sheath. The second tubular internal sheath may comprise a multi-lumen catheter. This second tubular internal sheath may not be reinforced.

The tubular internal sheath may include a working channel liner having a working channel lumen. The working channel lumen may include a hydrophilic coating. The flexible external sheath, cap and tubular internal sheath may form a fluid-impermeable contamination barrier to prevent contamination of the endoscope.

For example, an endoscope sheath device configured to prevent contamination of an endoscope may include: a cap configured to couple to a distal end of the endoscope; a flexible external sheath configured to extend over the endoscope, wherein a distal end region of the external sheath is sealingly coupled to the cap; and a tubular internal sheath comprising a working channel liner that is configured to be inserted through a lumen of the endoscope, the tubular internal sheath extending proximally from the cap and within the external sheath, wherein a distal end region of the tubular internal sheath is sealingly coupled to the cap so that a lumen of the tubular internal sheath is open through the cap, further wherein the distal end region is of the tubular internal sheath is reinforced to prevent the tubular internal sheath from collapsing when bending, wherein the flexible external sheath, cap and tubular internal sheath form a fluid-impermeable contamination barrier to prevent contamination of the endoscope.

For example, an endoscope sheath device configured to prevent contamination of an endoscope, the device may include: a cap configured to couple to a distal end of the endoscope; a flexible external sheath configured to extend over the endoscope, wherein a distal end region of the external sheath is sealingly coupled to the cap; and a first tubular internal sheath comprising a working channel liner that is configured to be inserted through a lumen of the endoscope, the tubular internal sheath extending proximally from the cap and within the external sheath, wherein a distal end region of the tubular internal sheath is sealingly coupled to the cap so that a lumen of the tubular internal sheath is open through the cap, further wherein the distal end region is of the tubular internal sheath is reinforced to prevent the tubular internal sheath from collapsing when bending; and a second tubular internal sheath comprising a multi-lumen catheter that is sealingly coupled to the cap and configured to be inserted through a lumen of the endoscope, the second tubular internal sheath extending proximally from the cap and within the external sheath, wherein the flexible external sheath, cap and the first and second tubular internal sheaths form a barrier to prevent contamination of the endoscope during use.

In any of the methods and apparatuses described herein the cap configured to couple to the distal end of the apparatus may be a removable cap that is configured to be squeezed between two fingers to fit over the distal end of the endoscope and may be squeezed to remove from the distal end of the endoscope. For example, an endoscope sheath device may include: a tubular external sheath configured to extend over the endoscope; a tubular internal sheath configured to extend within a lumen of the endoscope, the tubular internal sheath having one or more lumens; and a cap configured to couple to a distal end of the endoscope, wherein a distal end region of the tubular external sheath is sealed to the cap, and further wherein a distal end region of the internal sheath is sealed to the cap so that the one or more lumens of the tubular internal sheath is open through the cap, wherein the cap is configured to be removed by squeezing two sides of the cap. The cap may include a substantially cylindrical mating surface configured to mate with a distal end of the endoscope when compressed from an oval resting cross-sectional configuration into a substantially circular mating cross-sectional configuration. These caps may include a stress-relief cut-out region configured to decrease the force necessary to transition the cylindrical mating surface to the circular mating cross-section.

As used herein a substantially cylindrical surface may have approximately parallel sides (e.g., may deviate by a percentage, such as +/−10%, 9%, 8%, 7%, 6%, 5%, etc.). A substantially circular cross-sectional configuration may be approximately circular, and need not be perfectly circular, e.g., the radius may vary by a percentage around the circumference of the cross-section (e.g., by about +/−10% or less, 9% or less, 8% or less, 7% or less, 6% or less, 5% or less, etc.). Thus, when a cap is compressed from an oval resting cross-sectional configuration into a substantially circular mating cross-sectional configuration, the cap may be compressed from an oval resting cross-sectional configuration into mating cross-sectional configuration that is more circular than the oval resting configuration, but may still be somewhat oval.

In general, the cap may include one or more of: a snap fit, a friction fit, a magnet coupler, a bayonet connector or a threaded region. Any of these caps may include a latching connector configured to secure the cap to the distal end region of the endoscope. The latching connector may include an opening in the cap configured to engage with a projection on the distal end reign of the endoscope. Alternatively or additionally the latching connector may include a projection that mates with an opening on the endoscope.

In some examples the endoscope sheath device configured to prevent contamination of an endoscope includes: a cap configured to couple to a distal end of an endoscope; an external sheath sealingly coupled at a distal end to the cap; and one or more internal sheaths extending within the external sheath, wherein each internal sheath is sealingly coupled at a distal end to the cap and opens through the cap.

For example, an endoscope sheath device may include: a tubular external sheath configured to extend over the endoscope; a tubular internal sheath configured to extend within a lumen of the endoscope, the tubular internal sheath having one or more lumens; and a cap configured to couple to a distal end of the endoscope, wherein a distal end region of the tubular external sheath is sealed to the cap, and further wherein a distal end region of the internal sheath is sealed to the cap so that the one or more lumens of the tubular internal sheath is open through the cap, wherein the cap comprises a cylindrical mating surface configured to mate with a distal end of the endoscope when compressed from an oval resting cross-sectional configuration into a circular mating cross-sectional configuration; and a latching connector configured to secure the cap to the distal end region of the endoscope, wherein the flexible external sheath, cap and the first and second tubular internal sheaths form a fluid-impermeable contamination barrier to prevent contamination of the endoscope during use.

An endoscope sheath device may include a tubular external sheath configured to extend over the endoscope; a first tubular internal sheath configured to extend within a first lumen of the endoscope, the first tubular internal sheath having one or more lumens; a second tubular internal sheath configured to extend within a second lumen of the endoscope; and a cap configured to couple to a distal end of the endoscope, wherein a distal end region of the tubular external sheath is sealed to the cap, and further wherein a distal end region of each of the first internal sheath and the second internal sheath are sealed to the cap so that the one or more lumens of the tubular internal sheath is open through the cap, wherein the cap comprises a cylindrical mating surface configured to mate with a distal end of the endoscope when compressed from an oval resting cross-sectional configuration into a circular mating cross-sectional configuration; and a latching connector configured to secure the cap to the distal end region of the endoscope, wherein the flexible external sheath, cap and the first and second tubular internal sheaths form a fluid-impermeable contamination barrier to prevent contamination of the endoscope during use.

As mentioned above, also described herein are systems that may include any of the devices described herein. In particular, described herein are systems including a catheter adapted for use with a sheath as described herein. These catheters may include a handle region configured to pass the internal sheath(s). For example, described herein are endoscope systems including a fluid-impermeable contamination barrier to prevent contamination of an endoscope, the system comprising: an endoscope having a lumen and a handle; and an endoscope sheath device comprising: an external sheath configured to extend over the endoscope, an internal sheath comprising one or more lumens, the internal sheath configured to extend through the lumen of the endoscope, and a cap configured to couple to a distal end of the endoscope, wherein a distal end region of the external sheath is sealed to the cap, and further wherein a distal end region of the internal sheath is sealed to the cap so that one or more lumens of the internal sheath is open through the cap; and a manifold block removably coupled to the handle of the endoscope, wherein the manifold block comprises one or more valves in fluid communication with the lumen of the endoscope, wherein the internal sheath is configured to engage with the manifold block so that the one or more valves control passage of fluid through the one or more lumens of the internal sheath.

The internal sheath may comprise a multi-lumen catheter, and/or may comprise a single-lumen sheath (e.g., a working channel liner).

Any of these systems may include a port adapter configured to mate with the multi-lumen catheter to create isolated ports in fluid connection with each lumen of the multi-lumen catheter. These methods may include a sealing device configured to seal the one or more lumens of the internal sheath. The endoscope sheath device may further comprise a second external sheath configured to extend through a second lumen of the endoscope, wherein a distal end region of the second internal sheath is sealed to the cap so that one or more lumens of the second internal sheath is open through the cap. The manifold block may comprise a lumen connection configured to engage with the second lumen of the internal sheath. In some of these examples the manifold block is disposable. The manifold block may further comprise an umbilical linking the one or more valves of the manifold block to one or more connectors configured to couple to one or more of: a source or irrigation fluid, a source of air, and a source of vacuum.

Any of the sheath apparatuses (devices, systems, etc.) may optionally be used with a robotic endoscope, as described, including nested robotic endoscopes. The sheath devices described herein may be applied over an inner endoscope member (e.g., an inner rigidizing endoscope) before it is coupled with an outer endoscope member (e.g., a mother device or an overtube), so that the external sheath covers just the inner member, and the outer member may be separately cleaned or sterilized. In some examples the sheath device may be attached to the inner endoscope member after it is coupled with the outer endoscope member, so that the flexible external sheath may cover both the inner and outer endoscopes.

For example, a system comprising an elongate outer tube for use with an inner endoscope in a telescoping arrangement may include: an elongate outer tube, the elongate outer tube comprising an outer tube lumen; an external sheath coupled to a proximal end region of the elongate outer tube at a first end region; a cap sealingly coupled to a second end of the external sheath; and an internal sheath having one or more internal sheath lumen and extending within the external sheath and within the outer tube lumen, wherein the internal sheath is sealingly coupled to the cap so that the one or more internal sheath lumen is open through the cap. The cap may be configured to couple to a distal end of the inner endoscope and the internal sheath is configured to extend through a lumen of the inner endoscope. The elongate outer tube may be configured to be selectively rigidized, e.g., by applying positive pressure or negative pressure.

Also described herein are methods and apparatuses for inflating or collapsing the external sheath of the endoscope sheath device configured to prevent contamination of an endoscope. For example, any of these apparatuses may include a flexible tubular external sheath that is configured to be collapsed against the endoscope by applying suction (e.g., negative pressure) between the flexile tubular external sheath and the outside of the endoscope. The sheath device may be configured to maintain a seal between the flexible external sheath and the endoscope. In some examples the apparatus and/or method may be configured to apply positive pressure between the flexible tubular external sheath and the outside of the scope, e.g., to inflate the flexible external sheath. This may help anchor, navigate and/or secure the endoscope within the body. Both collapsing (e.g., applying negative pressure) and inflating (e.g., applying positive pressure) may be helpful for indicating that the sheath device is maintaining a fluid-impermeable contamination barrier relative to the body.

For example an endoscope sheath device may include: a flexible tubular external sheath configured to extend over the endoscope; a cap configured to couple to a distal end of the endoscope, wherein a distal end region of the flexible tubular external sheath is sealed to the cap; and a proximal sealing collar, wherein a proximal end region of the flexible tubular external sheath is sealed to the proximal sealing collar, further wherein the proximal sealing collar is configured to form an airtight seal against the endoscope, so that the tubular external sheath may be inflated or deflated by the application of fluid pressure (e.g., air pressure, saline pressure, etc.) between the flexible tubular external sheath and the outer surface of the endoscope. Any of these apparatuses may include a pressure port in fluid communication with an inner region of the flexible tubular external sheath and configured to apply positive or negative pressure between the flexible tubular external sheath and the outer surface of the endoscope. For example, a pressure port on the proximal sealing collar may be configured to apply positive or negative pressure between the flexible tubular external sheath and the outer surface of the endoscope. The flexible external sheath may comprise an elastomeric material. The flexible external sheath may have a non-uniform diameter along the length of the flexible external sheath. In some examples the flexible external sheath has one or more inflation regions along the length of the flexible external sheath configured to expand to a larger expanded radius when the flexible external sheath is inflated by the application of positive pressure.

The cap may be configured to seal to the distal end of the endoscope. In some examples the cap is configured to secure to the distal end of the endoscope and comprises one or more of: a friction fitting configured to secure the cap to the distal end of the endoscope, a snap fit configured to secure the cap to the distal end of the endoscope, a magnet configured to secure the cap to the distal end of the endoscope, a bayonet connector configured to secure the cap to the distal end of the endoscope, or a threaded region configured to secure the cap to the distal end of the endoscope.

Any of these devices may include a tubular internal sheath configured to extend within a lumen of the endoscope, the tubular internal sheath having one or more lumens, wherein a distal end region of the internal sheath is sealed to the cap so that the one or more lumens of the tubular internal sheath is open through the cap.

For example, an endoscope sheath device may include: a flexible tubular external sheath configured to extend over the endoscope; a tubular internal sheath configured to extend within a lumen of the endoscope, the tubular internal sheath having one or more lumens; a cap configured to couple to a distal end of the endoscope, wherein a distal end region of the flexible tubular external sheath is sealed to the cap, and further wherein a distal end region of the internal sheath is sealed to the cap so that the one or more lumens of the tubular internal sheath is open through the cap; and a proximal sealing collar, wherein a proximal end region of the flexible tubular external sheath is sealed to the proximal sealing collar, further wherein the proximal sealing collar is configured to form an airtight seal against the endoscope, so that the tubular external sheath may be inflated or deflated by the application of fluid pressure between the flexible tubular external sheath and the outer surface of the endoscope. In some examples the fluid pressure may be applied as air pressure. Alternatively other gas (e.g., carbon dioxide, etc.) or liquids (e.g., saline) may be used.

Also described herein are methods and apparatuses for confirming that an endoscope is uncontaminated after use. In general, these methods may include pressurizing the endoscope sheath device to confirm that the external sheath is not compromised, as might occur if it is torn or ruptured. For example, a method may include: performing a medical procedure in a body with the endoscope while the endoscope is ensheathed within an endoscope sheath device; withdrawing the endoscope from the body; applying positive pressure between the endoscope and an external sheath of the endoscope sheath device; and indicating, based on a decay of pressure from between the external sheath and the endoscope, if the endoscope sheath device is contaminated or not contaminated.

The procedure may be performed using any of the apparatuses described herein. For example, performing may comprise performing the medical procedure wherein the endoscope is ensheathed so that an outer surface of the endoscope is enclosed by the external sheath of the endoscope sheath device and an inner lumen of the endoscope is covered by an internal sheath, wherein the external sheath and the internal sheath form a continuous fluid-impermeable barrier.

The pressure may be applied from a pressure port on the endoscope or separate from the endoscope. In some examples the proximal end of the external sheath may include a port for applying pressure. Any of these methods may include applying positive pressure between the endoscope and an external sheath of the endoscope sheath device by at least partially inflating the external sheath. In any of these methods a proximal portion of the external sheath may be sealed to a proximal region of the endoscope. In any of these apparatuses and methods, a distal end of endoscope sheath device (e.g., the cap and/or the distal end region of the external sheath) may be configured to seal to the distal end region of the endoscope.

Indicating may include determining if the external sheath has developed a leak based on a decay of pressure from between the external sheath and the endoscope. The pressure may be monitored by a pressure sensor coupled to the pressure port or the applied pressure source, and/or the endoscope sheath device. In some examples a pressure indicator (e.g., gauge, sensor, dial, etc.) may be included. In some cases the method may include manually observing the inflated external sheath to detect a loss of pressure (indicating leak and possible contamination).

In general, indicating may comprise emitting a signal. Alternatively or additionally, indicating may include transmitting the signal (e.g., the pressure profile, pressure signal, and/or a processed signal based on the pressure signal) to a remote processor for storage, further processing and/or presentation to the user or a third party. In some examples indicating includes emitting an alert if the decay of pressure from between the external sheath and the endoscope exceeds a threshold, e.g., audible and/or visible alert.

For example, a method of confirming that an endoscope is uncontaminated may include: performing a medical procedure with an endoscope while a distal end of the endoscope is covered by a cap, wherein an internal sheath that is sealingly connected to the cap extends through a lumen of the endoscope from a distal end to a proximal end and so that one or more internal sheath lumen extends through the lumen of the endoscope and are open through the cap, further wherein an external sheath is sealingly connected to the cap and extends proximally over the endoscope; withdrawing the endoscope from the body; applying positive pressure between the endoscope and an external sheath of the endoscope sheath device; and indicating, based on a decay of pressure from between the external sheath and the endoscope, if the endoscope sheath device is contaminated or not contaminated.

Any of the apparatuses and methods described herein may include an applicator for applying and/or removing the endoscope sheath device onto and/or off of the catheter. For example, any of these methods and apparatuses may include an installing handle. The installing handle may include an internal region for holding the external sheath of the device in a compressed or folded (e.g., pleated, accordion folded, scrunched, etc.) configuration for deployment. The same installing handle may be used to remove and invert the external sheath once the procedure has been completed. For example a system including an installing handle may be configured as an endoscope sheath apparatus to prevent contamination of an endoscope, the apparatus comprising: a cap configured to couple to a distal end of an endoscope; an external sheath sealingly coupled at a distal end to the cap; one or more internal sheaths extending within the external sheath, wherein each internal sheath is sealingly coupled at a distal end to the cap and opens through the cap; and an installing handle, wherein at least a portion of the external sheath is held in a gathered configuration within a chamber of the installing handle, further wherein the one or more internal sheaths extend distally through the gathered external sheath and chamber and out of a distal end of the installing handle.

The cap may be positioned at a distal end of the installing handle. The installing handle may include a coupler at the proximal end of the installing handle configured to couple to a matching attachment on the endoscope. The external sheath may be held in the gathered configuration within the chamber so that the external sheath is compressed. In some examples the external sheath is held in the gathered configuration within the chamber so that a distal end of the catheter may fit within the external sheath when inserted from the distal end of the installing handle. The installing handle may comprise an outer gripping surface. In some examples the installing handle comprises a cylindrical shape. The external sheath may be gathered in a bellows (e.g., circular or cylindrically pleated) configuration.

The installing handle may include a distal-facing conical surface on a distal end of the installing handle. This distal-facing conical surface (e.g., funnel shape) may help capture any waste within the inverting external sheath and may help guide the external sheath to invert over itself when removing the external sheath from the endoscope.

Also described herein are methods of installing an endoscope sheath device onto an endoscope, the method comprising: inserting an internal sheath through a lumen of an endoscope from a distal end of the endoscope; advancing the distal end of the endoscope through an external sheath that is held in a gathered configuration within an installing handle; coupling a cap of the endoscope sheath apparatus to a distal end region of the endoscope; and pulling the installing handle proximally over the endoscope to deploy the external sheath over the endoscope. Any of these methods may include coupling the installing handle to the endoscope and/or removing the endoscope sheath device from the endoscope by advancing the installing handle distally over the endoscope to invert the external sheath over itself proximally.

In general, as described above, any method for removing the endoscope sheath device may include sealing a proximal end region of the internal sheath before withdrawing it (or them) from the lumen(s) of the endoscope. For example, the one or more internal sheaths may be sealed at a proximal sealing region that is configured to be sealed by mechanically sealing (e.g., crimping), by heat sealing, etc. Any of these methods may further include disengaging the cap from the endoscope and pulling the sealed internal sheath from out of the lumen of the endoscope.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 3A shown an example having a relatively short external sheath that may be secured to the distal end region of an outer tube. FIG. 3B shows an example including a proximal attachment on the external sheath. FIG. 3C shows an example having a long external sheath that may extend beyond the length of the outer tube and/or endoscope member.

FIG. 16B shows a schematic illustration of the system illustrating the use of the external working channels.

FIG. 20A shows a front view, FIG. 20B shows a side perspective view, FIG. 20C shows a side view and FIG. 20D shows a back view of the cap.

FIG. 21A is a distal end view of the endoscope and FIG. 21B is a perspective view.

IN FIG. 22A the device and endoscope are shown in a front perspective view. FIG. 22B shows a front (end) view, and FIG. 22C shows a side view.

FIG. 31A is a perspective view and FIG. 31B is a front (end) view illustrating the application of each of insufflation, wash fluid and irrigation fluid using the multi-lumen internal sheath, while maintaining the sterility of the endoscope covered by the endoscope sheath device.

In FIGS. 32A-32B the tip wash fluid is shown as a cylindrical stream for convenience; actual tip wash fluid may assume a different shape as it is passed over the tip.

In FIGS. 33A-33B the insufflation is shown as a flattened triangle for convenience; actual insufflation (e.g., a gas such as air) may assume a different shape as it is passed over the tip.

In FIGS. 34A-34B the irrigation fluid is shown as a cylindrical stream for convenience; actual irrigation fluid may assume a different shape as it is emitted from the tip.

In FIG. 35A the port adapter is shown partially transparent and engaged with an internal sheath.

FIG. 36A shows a front (end) view and FIG. 36B shows a side sectional view through the cap of FIG. 36A.

FIGS. 37A and 37B show side perspective views with the scope cap off and on, respectively, the distal end of the endoscope sheath device applied over an endoscope. FIG. 37B shows a side sectional view.

FIG. 40A schematically illustrates an example of a catheter. FIG. 40B schematically illustrates an example of an endoscope sheath device configured to form proximal seal to the endoscope so that the external sheath may retain positive or negative pressure. FIG. 40C schematically illustrates the endoscope sheath device coupled (and sealed to) the endoscope.

In FIG. 43A the external sheath includes a single expandable (e.g., balloon) region, while in FIG. 43B the external sheath has a pair of expandable (e.g., balloon) regions.

In FIG. 46A the inner (nested) endoscope is coupled to sheath at the distal end and the cover extends over the inner and outer endoscopes; applying positive pressure between the external sheath and the endoscopes causes the external sheath to deploy distally, driving the inner endoscope distally, as shown in FIG. 46B.

FIG. 50A shows a side view of one example of an endoscope sheath apparatus including an installing handle in a pre-deployed configuration. FIG. 50B shows the endoscope sheath apparatus of FIG. 50A in a top front perspective view and FIG. 50C shows the same endoscope sheath apparatus in a rear side perspective view.

DETAILED DESCRIPTION

Figure 1A:
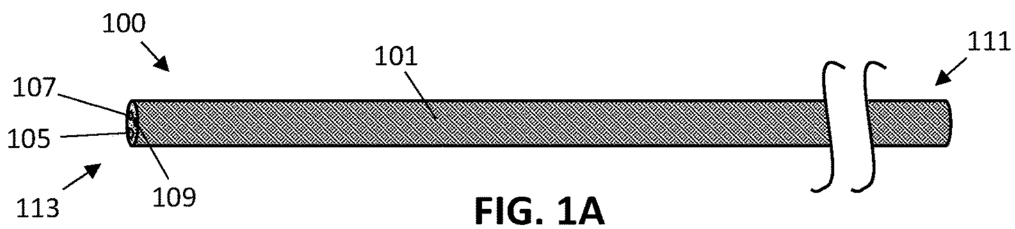
FIGS. 1A-1C schematically illustrate an example of a generic endoscope that may be used with the apparatuses and methods described herein.

In general, described herein are endoscope sheath assemblies (e.g., endoscope sheath devices and system) including a cap configured to couple to the distal end of the endoscope, an external sheath that extends over the endoscope (and optionally seals to or covers an outer elongate member coaxially over the endoscope), and one or more internal sheath(s) that extend within one or more lumens of the endoscope. Both the external sheath and the internal sheath are configured to seal to the cap. These apparatuses may be configured to prevent contamination of the endoscope without inhibiting any of the functions of the endoscope, including the ability of the endoscope to pass material into or out the distal end of the endoscope through an internal lumen or working channel and/or imaging from the distal end of the endoscope and/or moving relative to an outer elongate member.

Any of these apparatuses may be used with an endoscope that is coaxially arranged within a rigidizing overtube (outer elongate member). Either or both the outer elongate member and the endoscope may be configured to rigidize. Any appropriate rigidization may be used, including, but not limited to rigidization by applying positive and/or negative pressure. In general the rigidizing members described herein can transition from a flexible configuration (i.e., one that is relaxed, limp, or floppy) to a rigid configuration (i.e., one that is stiff and/or holds the shape it is in when it is rigidized). The apparatuses and methods described herein may be particularly well suited for use with rigidizing devices but may be used with non-rigidizing devices. In some examples, a rigidizing member (also referred to equivalently as a rigidizing device, a selectively rigidizing device or a selectively rigidizing member) may include a plurality of layers (e.g., coil or reinforced layers, slip layers, braided layers, bladder layers and/or sealing layers) that can together form the wall of a rigidizing member. The rigidizing members can transition from the flexible configuration to the rigid configuration, for example, by applying a positive or negative pressure to the wall of the rigidizing device or within the wall of the rigidizing device. With the positive or negative pressure removed, the layers can easily shear or move relative to each other. With the vacuum or pressure applied, the layers can transition to a condition in which they exhibit substantially enhanced ability to resist shear, movement, bending, torque and buckling, thereby providing system rigidization. Examples of rigidizing members that may be used with any of the devices and methods described herein may include (but are not limited to) those described, for example in described in international patent application No. PCT/US2016/050290, filed Sep. 2, 2016, titled "DEVICE FOR ENDOSCOPIC ADVANCEMENT THROUGH THE SMALL INTESTINE," international patent application No. PCT/US2016/050290, filed on Sep. 2, 2016, titled "DEVICE FOR ENDOSCOPIC ADVANCEMENT THROUGH THE SMALL INTESTINE," published as WO 2017/041052, international patent application No. PCT/US2018/042946, filed on Jul. 19, 2018, titled "DYNAMICALLY RIGIDIZING OVERTUBE," published as WO 2019/018682, international patent application No. PCT/US2019/042650, filed on Jul. 19, 2019, titled "DYNAMICALLY RIGIDIZING COMPOSITE MEDICAL STRUCTURES," published as WO 2020/018934, international patent application No. PCT/US2020/013937 filed on Jan. 16, 2020, titled "DYNAMICALLY RIGIDIZING COMPOSITE MEDICAL STRUCTURES," and PCT/US2021/034292, filed on May 26, 2021, entitled "RIGIDIZING DEVICES." Each of these application is herein incorporated by reference in its entirety.

Any appropriate rigidizing member may be used, including rigidizing members that are not formed of layers and/or actuated by pressure (positive and/or negative pressure). For example, the rigidizing members described herein may refer to any appropriate rigidizing device, including members that may be rigidized by jamming particles, by phase change and/or shape memory alloys, by interlocking components (e.g., cables with discs or cones, etc.), EAP (electro-active polymers) or any other rigidizing mechanism.

As mentioned, the sheath assemblies described herein may be used with one or more robotic systems, including telescoping, rigidizing robotic system as described, for example, in U.S. patent application Ser. No. 17/152,706 (titled "DYNAMICALLY RIGIDIZING COMPOSITE MEDICAL STRUCTURES," now U.S. Pat. No. 11,135,398), U.S. patent application Ser. No. 17/493,785 (titled "DYNAMICALLY RIGIDIZING COMPOSITE MEDICAL STRUCTURES"), and international patent applications no. PCT/US2021/034292 (titled, "RIGIDIZING DEVICES") and PCT/US2021/024582 (tiled "LAYERED WALLS FOR RIGIDIZING DEVICES"), each of which is herein incorporated by reference in its entirety.

Figure 1B:
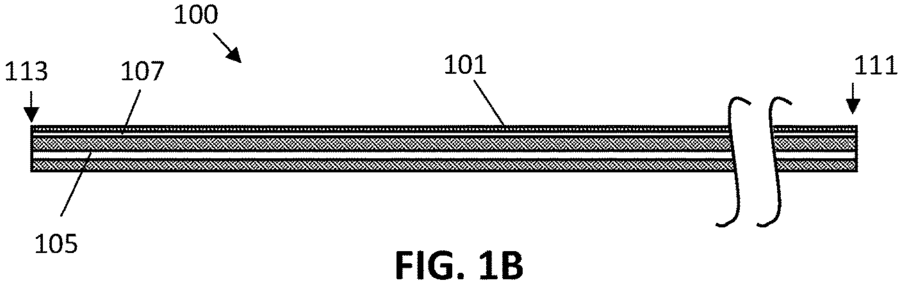
Figure 1C:
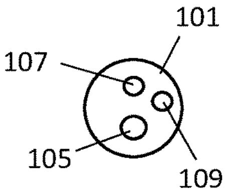

The endoscope sheath assemblies described herein may be used with a single endoscope. An endoscope may refer to an elongate instrument which can be introduced into the body and may include one or more lumens extending therethrough and may be used for examining, treating and/or diagnosing an interior region of a body. Any of these endoscopes may include imaging (e.g., typically by a CCD, CMOS chip, or fiber optic material) to give a view from the distal end of the device. The endoscope may generally be a catheter including one (or more than one) internal lumen extending the length of the endoscope. For example, in FIG. 1A, the endoscope 100 includes an elongate flexible (or in some examples, selectively rigidizable) body that extends from a distal end 113 to a proximal end 111. The endoscope includes a first lumen 105 (e.g., a working channel) and a second lumen 107 and a camera 109. The first lumen may be a working channel through which one or more tools may be inserted or/or manipulated for acting on tissue at the distal end of the endoscope within the body. The second lumen may be, e.g., a suction, a fluid (air, water, etc.) application lumen, or the like. The lumen (e.g., the internal working channel) may extend the length of the endoscope. The endoscope may be any appropriate length and width and may generally be formed of a biocompatible material. FIG. 1B shows a cross-section through the endoscope of FIG. 1A, and FIG. 1C shows a distal end view of the endoscope of FIG. 1A.

Figure 2A:
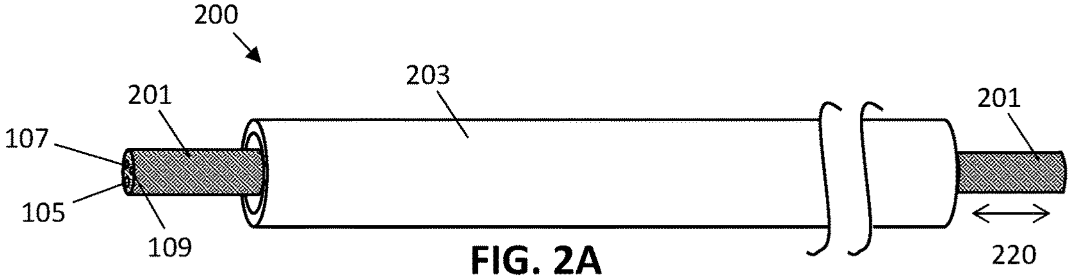
FIGS. 2A-2C schematically illustrate an example of a telescoping assembly including an endoscope that may be used with the apparatuses and methods described herein.
Figure 2B:
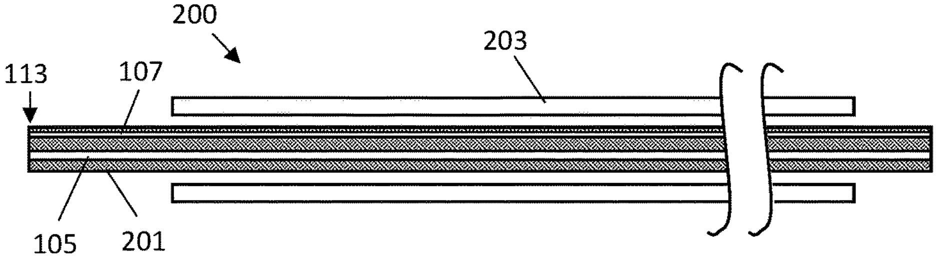
Figure 2C:
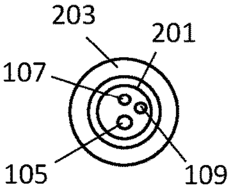

FIGS. 2A-2C illustrate an example of an assembly including an inner endoscope 201 that is coaxially arranged within an outer tube 203. The endoscope 201 may be similar or identical to the endoscope shown in FIGS. 1A-1C, and include one or more internal lumens 105, 107 (e.g., working channel 105) and may be configured to slide axially 220 within the outer tube 203. FIG. 2B show a section through the assembly of FIG. 2A and FIG. 2C shows a distal end view of the assembly of FIG. 2A. In some examples the assembly may be a telescoping assembly including the endoscope 201 and the outer tube 203 configured to be flexible but may be selectively rigidized. An endoscope or endoscope assembly such as those shown schematically in FIGS. 1A-1C and 2A-2C may be used with any of the endoscope sheaths (sheath devices) described herein.

Figure 3A:
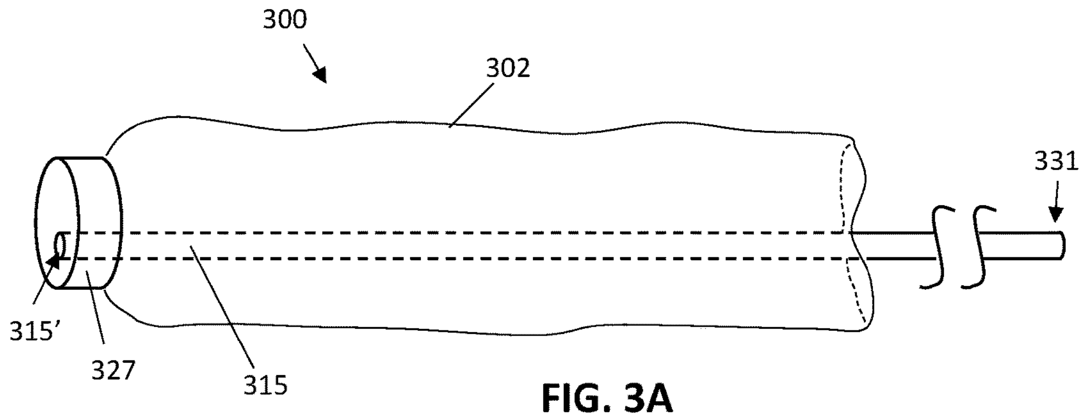
FIGS. 3A-3C schematically illustrate examples of endoscope sheaths as described herein.
Figure 3B:
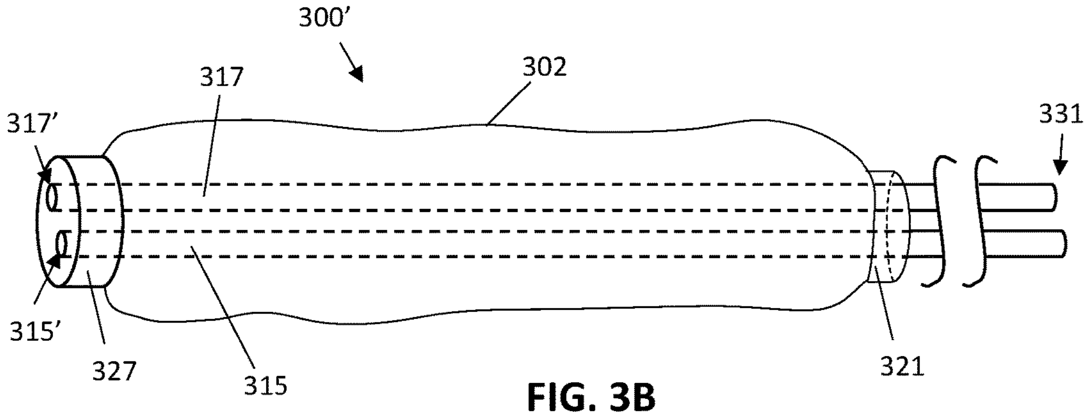
Figure 3C:
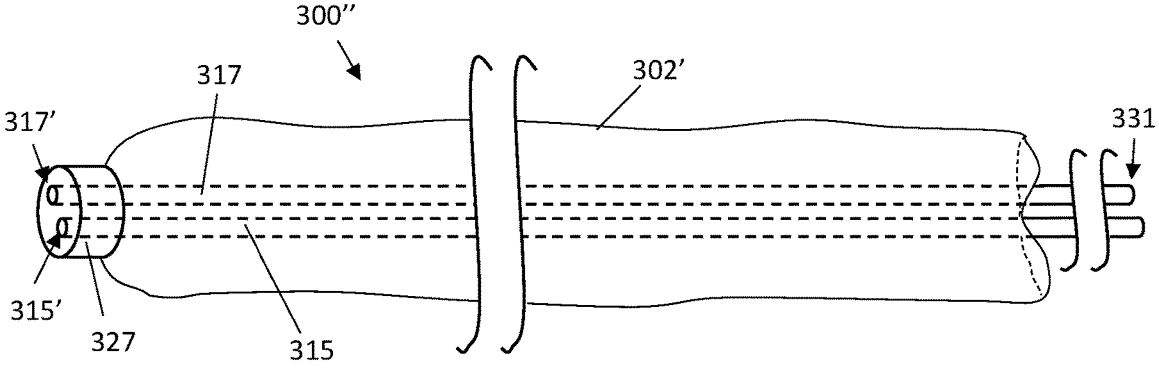

FIGS. 3A-3C illustrate examples of endoscope sheaths as described herein. The sheaths illustrated in FIGS. 3A-3C are shown unattached or unconnected to either an endoscope or an endoscope assembly (e.g., an outer tube and an inner endoscope member). In FIG. 3A for example the endoscope assembly 300 includes a cap 327 that is configured to secure to and over a distal end region of an endoscope. For example, the cap 327 may snap onto the distal end, e.g., the cap may connect to the distal end of the catheter by a deflectable snap on either the cap, the distal end of the endoscope, or both. For example, the cap may include a bendable or flexing member to releasably lock (e.g., by a "snap fit") the cap onto the distal end of the endoscope. In some examples the cap may secure (releasably secure) to a distal end of an endoscope by a clamping or spring-loaded mechanism. In some examples the cap may couple by engaging a screw-on or threaded region. In some examples the cap 327 may couple by a friction fit (e.g., the cap may include one or more shear surfaces that are configured to secure the cap to the distal end of the endoscope). In some examples the cap may couple magnetically to the distal end region of the scope to secure the cap to the distal end. In some examples the cap may be secured to the distal end of the scope by a bayonet connector.

In FIG. 3A an external sheath 302 is shown sealing connected (e.g., fused, welded, integrally formed, etc.) to the cap 327. The external sheath may be flexible and in particular may be sufficiently thin or thin-walled that it may be lightweight and may move relative to the outer tube (not shown) as the endoscope moves in and out of the outer tube and/or rotates relative to the outer tube. The example shown in FIG. 3A includes a single internal sheath 315 extending proximally within the external sheath, and sealing connected to the cap 327. The sealing connection between the cap and the internal sheath is such that the internal lumen of the internal sheath is open to the body so that fluids may be applied through the endoscope without compromising the barrier between the patient and the endoscope. In FIGS. 3A-3C the internal sheath forms only a single lumen is shown in this example, in other examples multiple lumen structures may be used, such multi-lumen catheters. Thus, as shown in FIG. 3A the internal sheath may form an opening 315' through the cap that is continuous with the internal sheath 315 shown.

In this example the external sheath 302 is shorter than the internal sheath 315, and the internal sheath 315 extends proximally 331 from out of the external sheath. In some examples, a short external sheath may couple to an outer tube (not shown in FIG. 3A) such as an overtube, and may seal to the outside so that the outer tube may act with the external sheath to protect the endoscope extending within the outer tube.

FIG. 3B illustrates another example of an endoscope sheath device 300' (e.g., sheath assembly) similar to that shown in FIG. 3A, but with a second internal sheath 317, having a distal opening 317' through the cap 327 that may pass material or tools into and out of the endoscope to treat tissue. In FIG. 3B the second internal sheath 317 may form a working channel liner that may line the working channel of the endoscope. The internal sheaths may be catheters, including multi-lumen catheters. The external sheath 315 in FIG. 3B may be similar to that shown in FIG. 3A and may be relatively short, e.g., may couple to an outer tube (not shown). In any of these sheath assemblies described herein the external sheath may include a proximal attachment on the external sheath configured to secure the external sheath to an outer surface of an outer tube that is coaxially arranged over the endoscope.

FIG. 3C shows a sheath assembly 300" similar to that shown in FIG. 3B, including a first internal sheath 315 that opens 315' through the cap 327 and a second internal sheath 317 (e.g., working channel liner) that also opens 317' through the cap 327, both sealingly attached to the cap, and an external sheath 302' that is elongate and sealingly coupled to the cap at a distal end and may optionally include a proximal attachment region or proximal attachment 321 for attaching to either the endoscope or an outer tube that is configured to coaxially fit over the endoscope.

In any of these examples the cap may be clear (transparent) to allow imaging through or may include a window region configured to align with a camera region of an endoscope. In some examples, the cap has an anti-reflective or anti-glare coating.

Figure 4A:
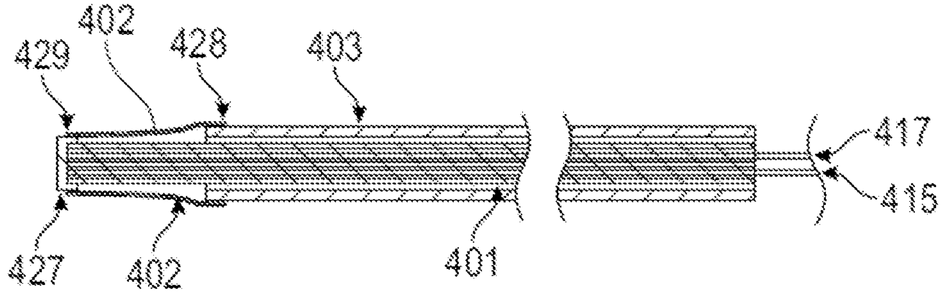
FIGS. 4A-4C schematically illustrate examples of endoscope sheaths shown attached to a telescoping (e.g., mother/child) endoscope assembly.
Figure 4B:
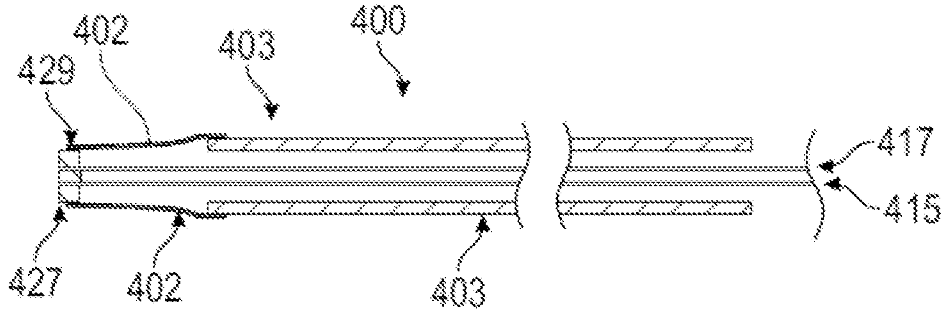
Figure 4C:
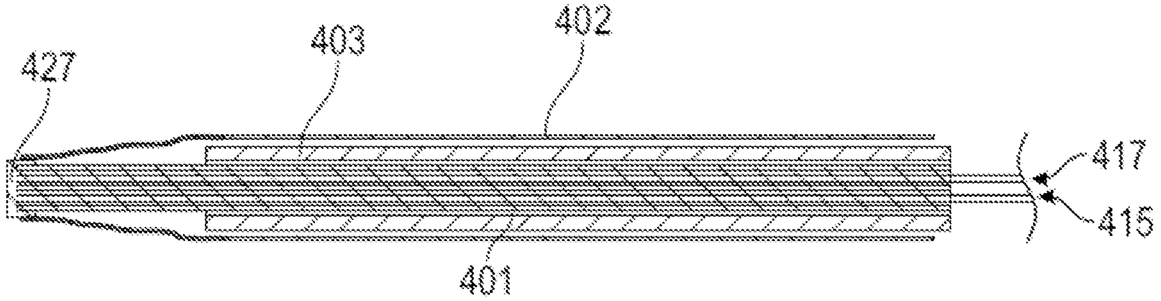

FIGS. 4A-4C schematically illustrate examples of sheath assemblies shown coupled to endoscopes and outer tubes that are coaxially arranged over the endoscopes to allow telescoping movement between the endoscope and outer tube.

In any of these apparatuses the sheath assembly may include the outer tube, which may therefore be a single-use component that may be coupled to the external sheath. For example, FIG. 4A shows a section through a sheath apparatus configured as a system including a flexible outer tube 403 for use with an inner endoscope 401 in a telescoping arrangement. In this example the elongate outer tube 403 is coupled (e.g., sealingly coupled 428) at a distal end region to an external sheath 402. The external sheath 402 is in turn sealingly coupled 429 to a cap 427 at the distal end of the external sheath. The cap 427 may then removably coupled to the endoscope 401 at the distal end of the endoscope. The external sheath 402 may be sealingly coupled around the outer perimeter of the cap, as shown. A pair of internal sheaths 415, 417 having one or more internal sheath lumen extend within the external sheath and within a lumen of the endoscope 401. The internal sheaths both sealingly couple to the cap so that the internal sheath lumen are open through the cap to allow material to pass through the endoscope. For example, one of the internal sheath lumen may connect to a water supply and the other may connect to a suction and/or may provide a working channel, e.g., for tools.

In this example, the outer tube may be connected to the sheath tip with a thin flexible external sheath which permits substantial movement of the sheath tip both away and towards the distal tip of the outer tube, e.g., allowing axial (reciprocating) and well as torsional ('roll axis') movement even with the external sheath. The internal working channels and supply lines of the endoscope contain the liner (e.g., internal sheaths) that are essentially long tubes the length of the endoscope so that the endoscope lumen sheathed with the internal sheaths that function as the tubes that deliver gasses and liquids or as the internal working channel through which surgical tools or suction vacuum may be delivered. The internal sheaths and external sheath are joined together at the cap (e.g., the sheath tip 427). The cap provides a transparent face for the endoscope's camera and illumination light, and may also incorporate nozzles (e.g., an exit for tip washing) and pass-through ports for the contents of the internal sheaths to be delivered through the cap. As mentioned, the cap may be configured to fasten to the endoscope tip so that it remains well attached during procedures but can then be decoupled to change out the sheath assembly. The combination of the outer tube sealed to the external sheath, the external sheath sealed to the cap, and the cap sealed to the internal sheaths therefore fully isolates the endoscope from the patient.

FIG. 4B shows the sheath assembly 400 of FIG. 1 without the endoscope 401, including the attached outer tube 403, cap 427, and the pair of internal sheaths 415, 417. The sheath assembly 400 may releasably couple to the endoscope, e.g. by inserting the internal sheaths 415, 417 through lumen of the endoscope and snapping or otherwise coupling the cap 427 to the distal end of the endoscope.

FIG. 4C shows an alternative example, similar to that shown in FIG. 3C, in which the external sheath 402 is not coupled to the outer tube 403, and extends proximally along much or all (or more than) the length of the outer tube 403. As shown in this example, the external sheath 402 extends proximally to the proximal end region of the endoscope and/or outer tubes.

Figure 5A:
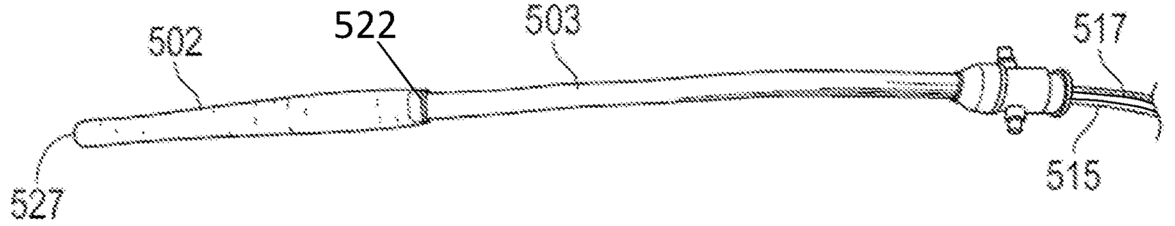
FIGS. 5A-5C show an example of an endoscope sheath attached to a telescoping endoscope assembly.
Figure 5B:
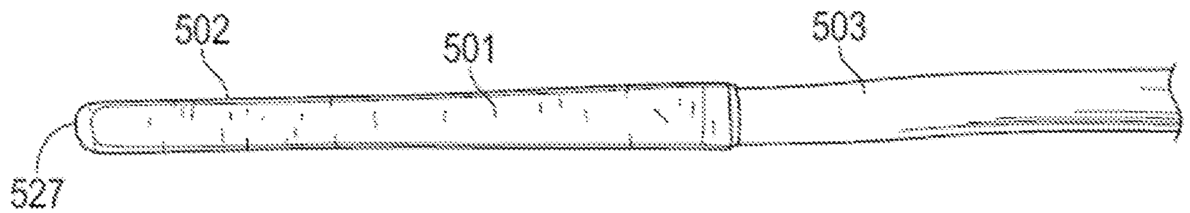
Figure 5C:
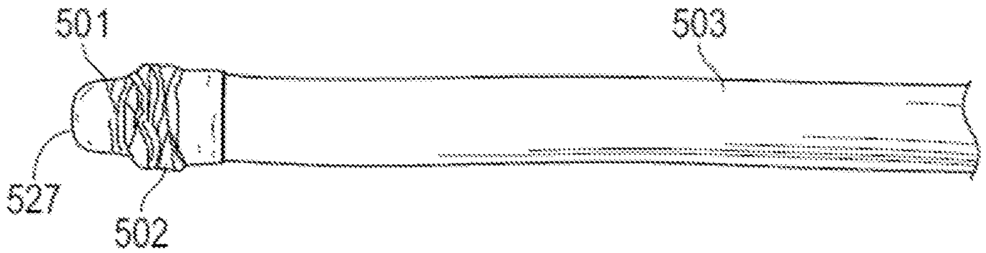

FIGS. 5A-5C illustrate an example of an external sheath 502 attached to an outer tube 503, and includes two internal sheaths 517, 515 (shown sticking out of the proximal end of the outer tube 503 in FIG. 5A). The external sheath in the device shown in FIGS. 5A-5C includes a base 522 at the proximal end of the external sheath that may seal to the outer endoscope 503 (e.g., overtube). The outer tube in this example is shown shorter than normal but is representative of the full-length version. The cap 527 of the sheath assembly is coupled to the distal end of the external sheath 502. In FIG. 5A the sheath assembly is not yet coupled to an endoscope. FIG. 5B shows an endoscope 501 inserted into the outer tube 503 with the endoscope 501 extended fully to the limit of the external sheath 502. The tip (cap 527) of the external sheath fastens to the distal end region of the endoscope and extends and retracts with the endoscope as described above.

FIG. 5C shows the endoscope 501 protected within the external sheath 502 and fully retracted into the outer tube 503 with the external sheath tip 527 still attached to the endoscope tip. Note that the external sheath 502 bunches up and does not restrict the retraction or extension or bending of the endoscope.

In operation, the configuration of the sheath assembly incorporating the outer tube as shown in FIGS. 5A-5C may be a one-time use and/or disposable. In this example, the endoscope may be inserted through the outer tube and fully into the external sheath and attached to the sheath tip. The outer tube and/or the endoscope in the example may be selectively rigidizing devices that are actuated by the application of positive pressure or negative pressure. In this example, after the endoscope, outer tube and internal sheaths are connected to external control, vacuum and supply lines, the system is ready to be used in a procedure, e.g., inserted into a body. The sheath may protect the endoscope 501 from contacting any material that may contaminate the endoscope. After the procedure, the internal sheaths and the outer tube may both be disconnected from the rest of the system and removed from the endoscope and then discarded. The endoscope can then receive a new sheath which incorporates a new outer tube with internal and the external sheaths and be immediately re-used. No high-level disinfection of the endoscope is required between procedures, which saves time and expense. As described herein, the removal process may include sealing the internal sheaths to prevent contamination.

In any of these apparatuses and method, after using the sheath assembly (e.g., endoscope sheath device), it can be pressure tested to confirm that it has remained leak-free and that the underlying structures (e.g., endoscope) therefore remains clean. To do so, the external sheath can be inflated at least partially, e.g., by injecting pressurized air through a pressure port. The external sheath may be sealed at either or both ends. The internal sheath can be sealed (for example, proximally, as it exits the liners). The method or apparatus may monitor pressure, e.g., using a pressure sensor configured to detect pressure within the external sheath when inflated. The pressure sensor may track a pressure decay curve that may be reported and/or analyzed to determine if there is a leak, suggesting contamination. The pressure data may be reported to the operator and/or the apparatus may automatically or semi-automatically determine if there is a leak based on the pressure data. For example the apparatus may include software, hardware and/or firmware to receive pressure data configured to analyze the pressure data (e.g., decay curve), compare the pressure response to predetermined values to determine if there is a leak.

In some examples the external sheath extends the entire length of the outer tube, and the outer tube is not incorporated into the external sheath, as described in FIG. 4C. In this configuration, the outer tube is also fully isolated from contamination and can be reused with a new sheath without needing to be disinfected.

Figure 6A:
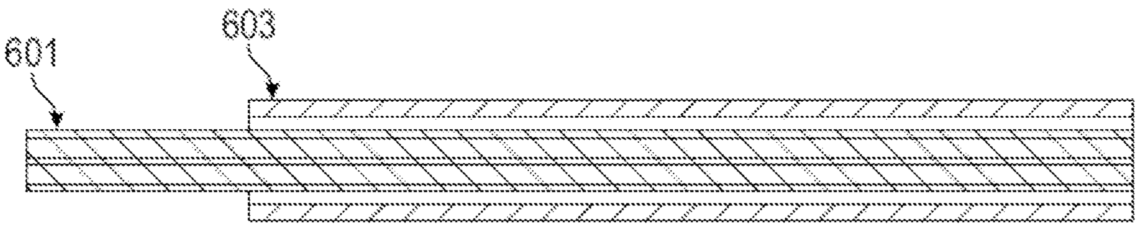
FIG. 6A schematically illustrates an example of a telescoping endoscope assembly.
Figure 6B:
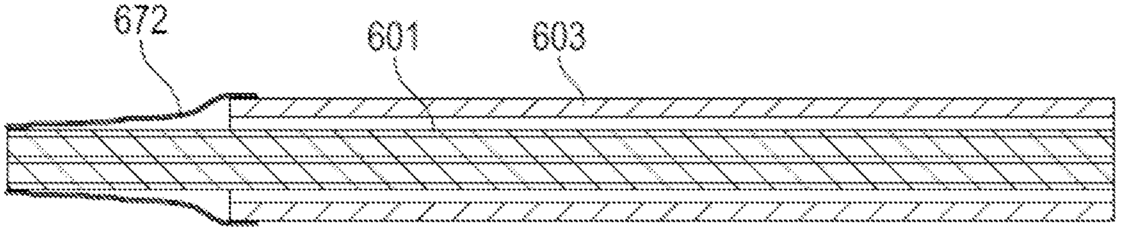
FIG. 6B schematically illustrates an example of a telescoping endoscope assembly with a partial sheath.

FIG. 6A shows a schematic example of a telescoping assembly, including an outer tube 603 and endoscope 601 shown without a sheath assembly attached. In contrast to the sheath assemblies described above, FIG. 6B shows an example of a system including only a partial external sheath portion 672 that is coupled between the outer tube 603 and endoscope 601, but does not include a cap or internal sheaths. In this example, although the space between the endoscope 601 and outer tube 603 may be kept fee of contamination, the outer surface of the outer tube and the inner lumen of the endoscope may both become contaminated.

Figure 7A:
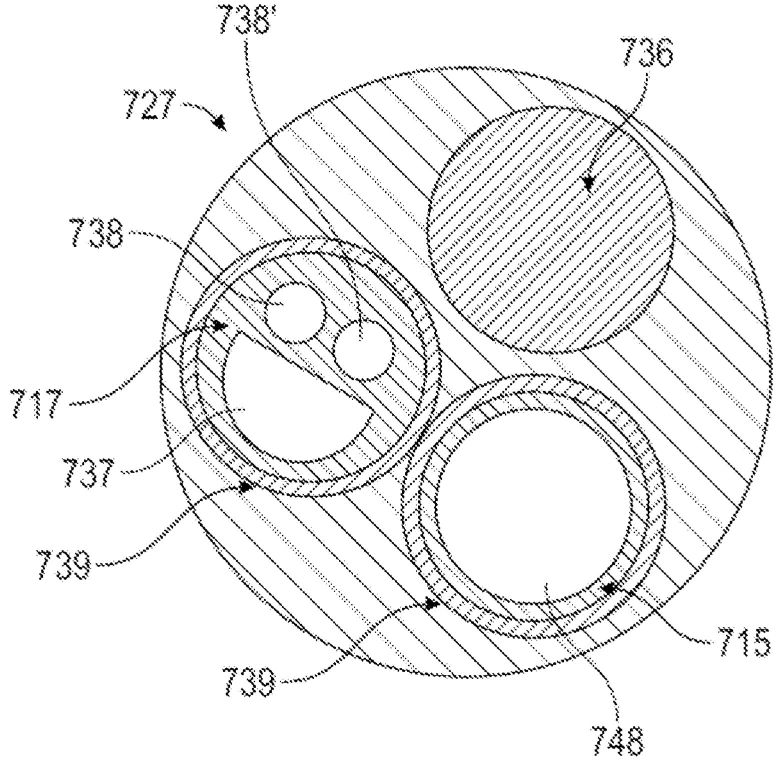
FIG. 7A schematically illustrates an example of a cap of a sheath assembly shown en face.

As mentioned above, any appropriate cap may be used. For example, FIG. 7A illustrates one example of a cap 727 shown in an end-on view. The cap may be formed of a clear material, such as clear polymeric material (e.g., polycarbonate (PC), polymethylmethacrylate (PMMA), acrylic, polyethylene terephthalate (PET), polyvinyl chloride (PVC), polyethylene (PE), cyclic olefin copolymer (COC), etc.). In some examples, as shown in FIG. 7A, a transparent camera window region 736 may be included. The cap may also include a sealed junction 739 to the fixed internal sheath ("fixed sleeve") such as a multi-lumen extrusion sheath 717 and/or a working channel sheath 715. The insides of these internal sheaths are open, as shown, to allow access to the body region at the distal end of the apparatus. For example, the multi-lumen extrusion sheath 717 includes three sub-lumen 737, 738, 738', e.g., a lumen for water 737, for air 738, and/or for vacuum 738' (or an additional air/water channel). In FIG. 7A the working channel sheath also include an open channel 748 that may be used to pass tools through the endoscope.

Figure 7B:
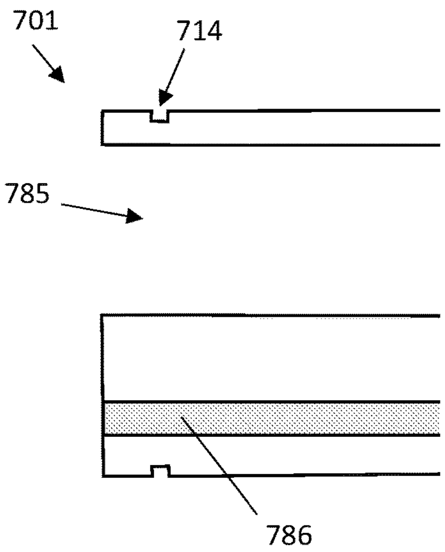
FIG. 7B is an example of a section through an example of an endoscope.
Figure 7C:
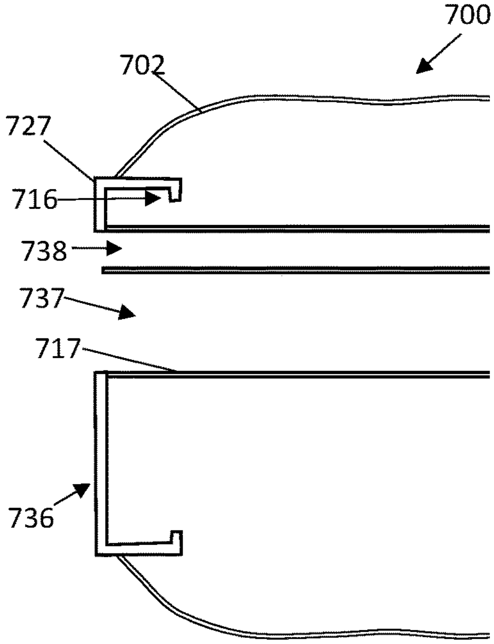
FIG. 7C shows a section through one example of a sheath assembly.

FIG. 7B shows a section through a distal end region of one example of an endoscope 701 that may be used with a sheath assembly as described herein. In FIG. 7B the endoscope 701 includes an internal lumen 785 that extends the length of the endoscope and opens at the distal end of the endoscope. FIG. 7C shows a sectional view through an example of a sheath assembly 700 including a cap 727, an external sheath 702, an interior sheath 717 that is configured as a multi-lumen 738, 737 extrusion sheath. The external sheath 702 may be coupled to an elongate outer tube (not shown in FIG. 7C) or may be long enough to extend down the full length of a separate elongate outer tube and/or endoscope.

Figure 7D:
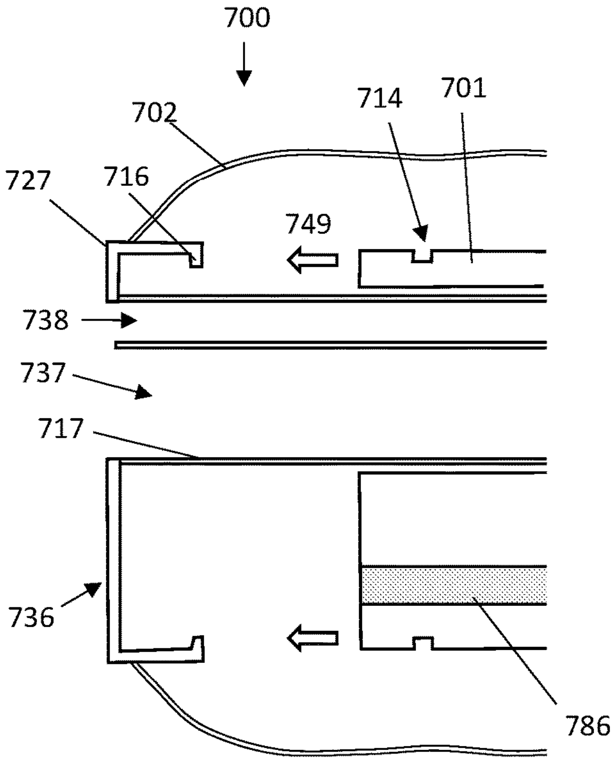
FIGS. 7D and 7E show side sectional views through one example of a sheath assembly of FIG. 7C coupling to the endoscope of FIG. 7B.
Figure 7E:
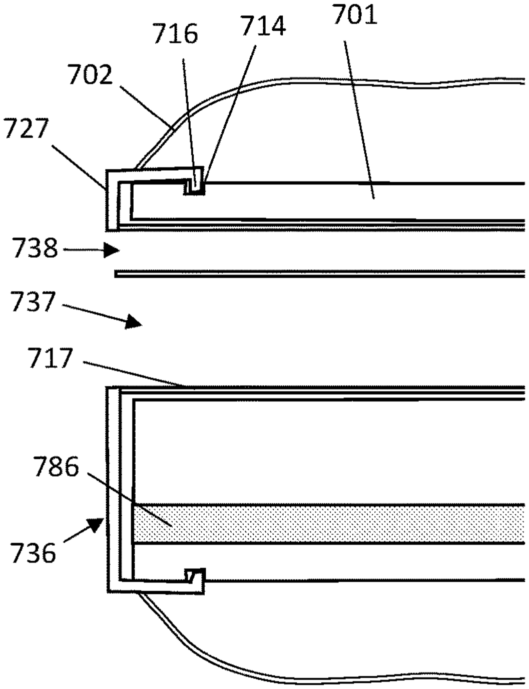

FIGS. 7D-7E illustrate the application of the sheath assembly 700 of FIG. 7C over the endoscope 701 of FIG. 7B. The proximal end of the interior sheath 717 may be first inserted into the internal lumen 785 of the endoscope and the endoscope may be advanced distally 749 until the cap 727 of the sheath assembly 700 can couple to the endoscope 701. For example, FIG. 7D shows a sectional view through the distal end region of the sheath assembly 700 with the endoscope 701 partially inserted. The external sheath 702 of the sheath assembly is sealed around the outside of the cap 727, and the internal sheath 717 is also sealed to the inside of the cap 727. As mentioned, the internal sheath 717 in this example has two lumen 738, 737 that open through the cap so that material (e.g., air, water, saline, etc.) may pass into or out of the lumen of the sheath, through the endoscope without contaminating the lumen of the endoscope 701. The cap 727 in this example is optically transparent at least over the camera window region 736, although in some examples the entire cap may be transparent, so that the imaging camera 786 of the endoscope 701 may image through the cap 727.

In FIG. 7D the sheath assembly is shown with the cap 727 not yet connected to the endoscope 701. The endoscope 701 may be driven distally 749 (or alternatively and/or additionally the cap may be driven proximally) to engage with the cap 727, as shown in FIG. 7E. In this example recessed region 714 at the distal end region of the endoscope may engage with a connector 716 (e.g., a deformable or deflectable connector) on the cap to secure the cap to the distal end of the endoscope, as shown in FIG. 7C. The recessed region 714 may be a cavity and/or it may be a lip, ridge or rim. In some examples the connector may include a shear surface configured to secure the cap to the distal end of the endoscope, a magnet configured to secure the cap to the distal end of the endoscope, a bayonet connector configured to secure the cap to the distal end of the endoscope, a threaded region configured to secure the cap to the distal end of the endoscope, or the like. Because the connection occurs within the external sheath or between the external sheath and the internal sheath(s), this connection does not need to form a seal, but should be secure so that as the endoscope is moved axially and/or in rotation, the cap remains at the distal end of the endoscope.

As mentioned above, in order to prevent contamination of the endoscope and/or the outer tube, in any of these example apparatuses described herein, the internal sheaths (e.g., working channels, multi-lumen catheters, etc.) may be sealed before they are removed from the endoscope (and in some cases the outer tube). This can be done in several ways. For example the one or more internal sheaths (which may be configured as catheters) may be plugged, crimped, blocked by an adhesive or other plug, heat sealed, etc. The sealing methods used may stay within the outside diameter of the internal sheath so that it can be withdrawn through the endoscope. For example, see FIGS. 10A-10C and 14.

The apparatuses described herein may incorporate internal working channels and supply lines into the disposable sheath. This may effectively make those elements of an endoscope disposable one-time-use elements which protects the patient as well as the endoscope equipment. As mentioned, these working channels (working channel liners) may be sealed before their removal.

In general, these sheath apparatuses described herein are configured so that the endoscope and the outer tube may roll relative to each other in addition to sliding axially. In some examples the external sheath can be intentionally torqued as it accommodates the rotation of one relative to the other. Movement of the inner endoscope and/or outer tubes may be done manually or robotically, and the sheath assemblies described herein may advantageously accommodate a variety of both longitudinal/axial movement as well as rotational movement between the inner endoscope and outer tubes.

Figure 11:
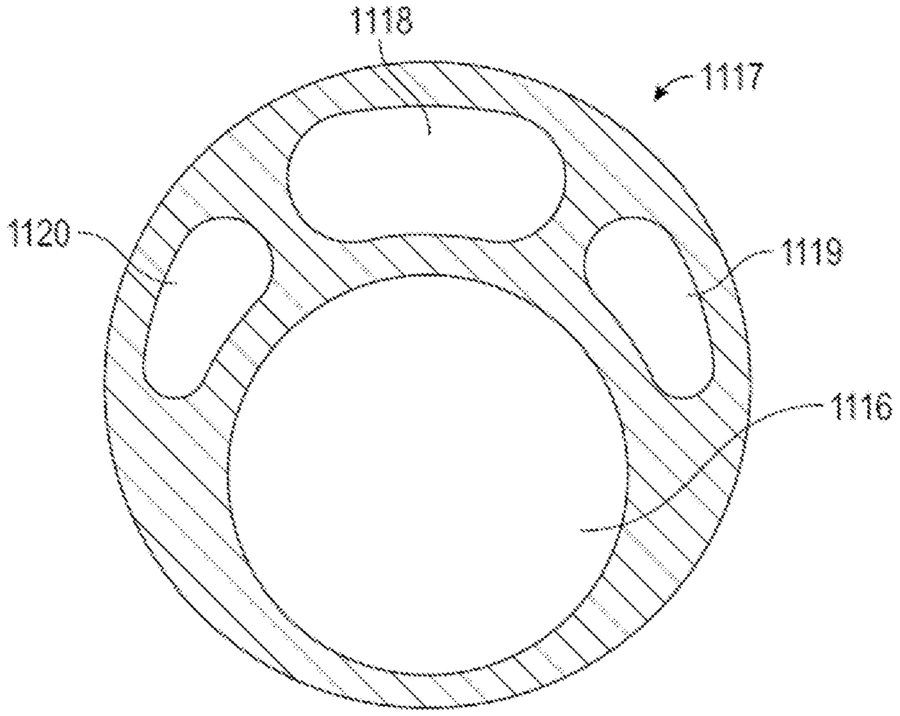
FIG. 11 is a section through one example of a multi-lumen catheter that may be used as an internal sheath as described herein.

Also described herein are port adapters for the easy fluid connectivity to small-bore, multi-lumen catheters (extrusions) that may be used as internal sheaths (working channel liners). For example, FIG. 11 illustrates a cross section of one example of an internal sheath (multi-lumen extrusion, MLE) 1117 that incorporates a working channel 1116 with 3 other water/gas channels 1118, 1119, 1120 into a single extrusion. Thus, in some configurations, only one internal sheath may be needed.

A multi-lumen internal sheath such as that shown In FIG. 11 may be used with a port adapter to allow access to all of the internal lumen within the internal sheath. Some of the lumens may connect in one direction (i.e., out the side), and some may connect in other directions (for example, axially or in-line). In any of these apparatuses and methods the proximal end of the multi-lumen catheter may be sealed, but one or more openings into the lumens may arranged along the sides of the distal end region, e.g., for mating with a port adapter, as described herein. In some examples the port adapter may instead be configured to couple with and access the distal end of the multi-lumen catheter forming the internal sheath (e.g., inner liner), for example, forming seals with the individual lumens of the multi-lumen catheter. Note that any of the port adapters described herein may be configured for use with a single lumen internal sheath (e.g., single-lumen catheter), by making a sealing contact with the lumen of the internal sheath, either through a side opening or at the distal end (or both).

Figure 8A:
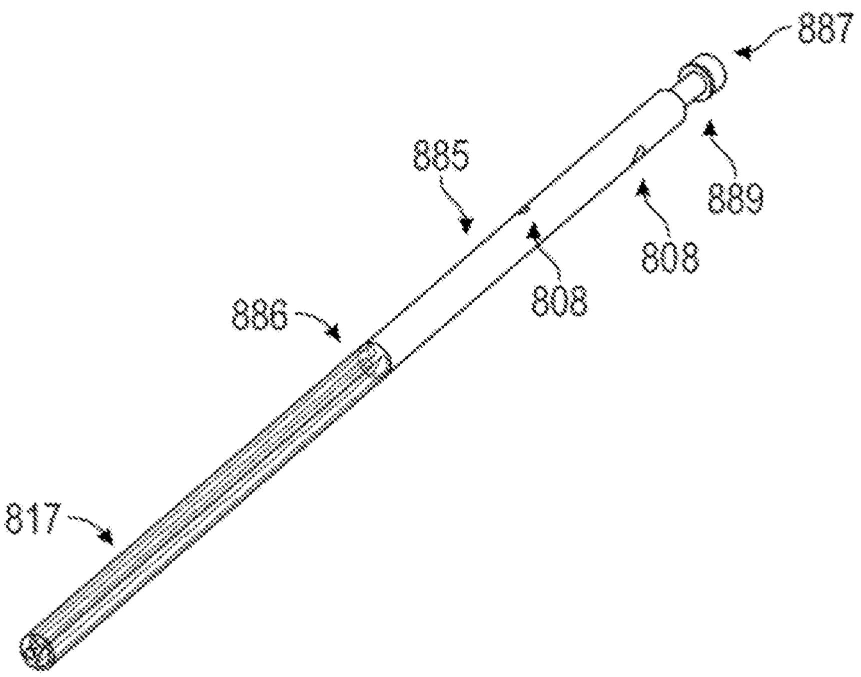
FIGS. 8A-8B illustrate the use of an example of a port adapter manifold for coupling to a multi-lumen catheter (of an internal sheath) as described herein.
Figure 8B:
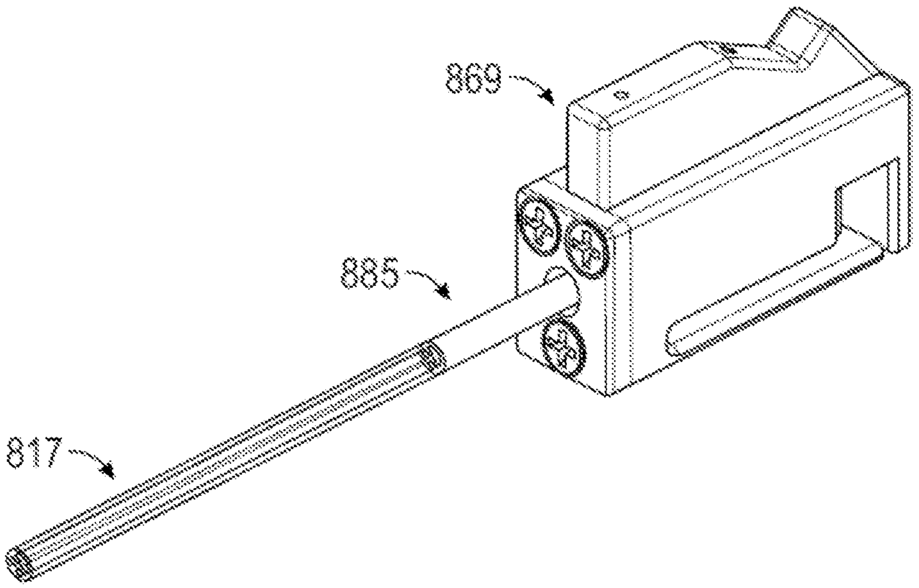
Figure 9A:
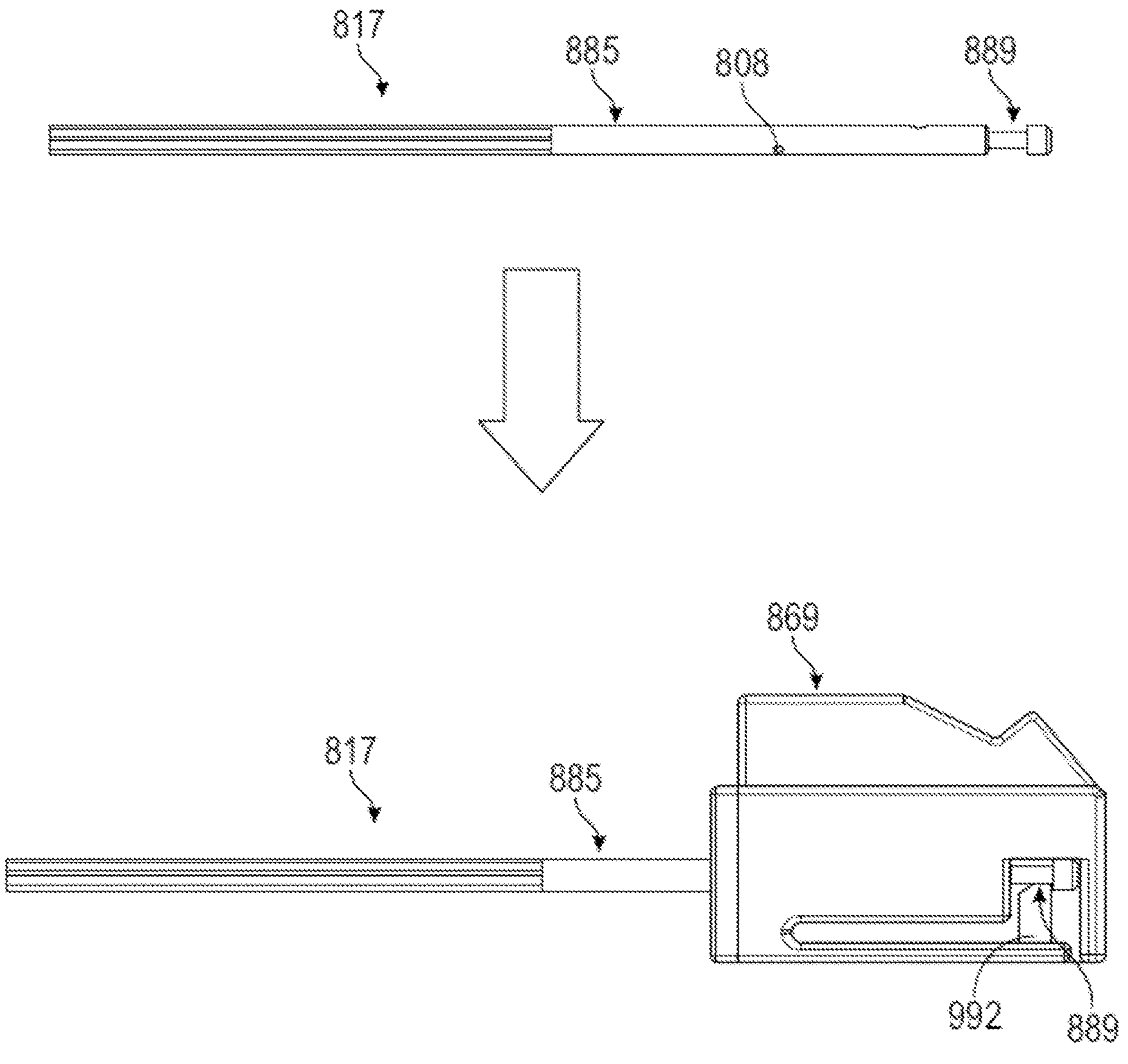
FIG. 9A schematically illustrates an example of a port adapter manifold engaging with a multi-lumen catheter.
Figure 9B:
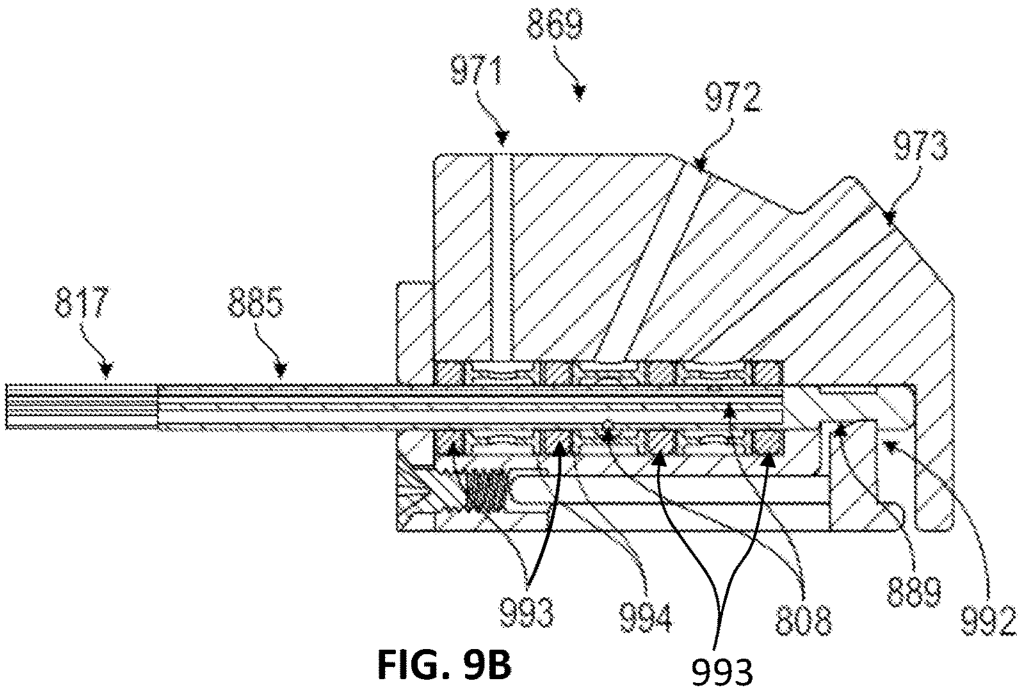
FIG. 9B shows a section through the port adapter manifold of FIG. 9A, which is similar to that shown in FIGS. 8A-8B.

Returning now to FIGS. 8A-8B, an internal sheath 817 configured as a multi-lumen extrusion (MLE) is shown with one example of a port adapter. In FIG. 8A, the internal sheath includes a rigid or semi-rigid connector tip 885 including lateral openings 808 into each of the lumen of the internal sheath 817, shown attached to the proximal end 887 of the internal sheath 817 at an optional joint 886. The joint may or may not be necessary, i.e., 817 may have the exit holes without the need for as a separate connector tip 885. The proximal end may also include an engagement structure (e.g., neck region 889) that may engage with a port adapter, as shown in FIG. 8B. In FIG. 8B, the connector tip 885 of the internal sheath 817 is inserted into a receptacle manifold of the port adapter 869 which provides connections for each lumen (or channel) in the internal sheath, as shown in FIGS. 9A-9B. In this configuration, the system is not radially positionally dependent, i.e., it may be inserted such that any radial configuration properly ports to the mating lumens. Between each of the radial ports is a separating and sealing gasket (e.g., O-ring). Between each sealing gasket is a spacer ring that permits through-flow.

FIG. 9A show an example of connection of the internal sheath 817 into a port adapter 869 which provides individual passthrough connections to each independent lumen in the multi-lumen catheter. In any of these port connectors, the proximal end of the internal sheath may engage with the port connector to secure it in place, and/or to align the openings 808 of the internal sheath with connectors of the port connector. In FIG. 8A the port connector 869 includes an internal sheath connector receptacle with a releasable locking mechanism 992 that engages with the engagement structure 889 at the proximal end region of the internal sheath. In alternative embodiments, 885 may have no special end geometry 889, and there could be, for example, an angled metal tang that 'grabs' the outside of the 885, serving to keep it retained. To remove, the tang could be deflected out of the way, such that it no longer contacts 885.

FIG. 9B shows an example of a cross section of the port adapter of FIG. 9A. In this example, the proximal end connector 885 of an internal sheath is inserted and latched into a receptacle manifold of a port adapter as shown in FIG. 9A. Flow from each lumen may be kept separate and passed through to individual ports 971, 972, 973 for connection to supply lines. A three-channel implementation is shown, but more or fewer channels (or lumens) could be accommodated using this technique.

In FIG. 9B, each individual port includes an annular sealing region 994 (for example, by the use of O-rings 993, which create two or more radial seals. In between the O-rings 993 are spaces that transmit flow: for example, rings with channels and cross-drilled geometry. When the internal sheath 817 is secured in the port connector, the lateral openings 808 into each lumen are aligned along the length of the proximal end so that they are positioned with an annular sealing region specific to each lumen. In FIG. 9B, the two annular sealing regions on the right side of the figure are each aligned with an opening 808 in the internal sheath. Thus, fluid may pass into or out of the opening from this annular sealing region that is fluid communication with a port 972, 973 on the port connector 869. These ports may be standardized for fitting any appropriate connector.

Figure 9E:
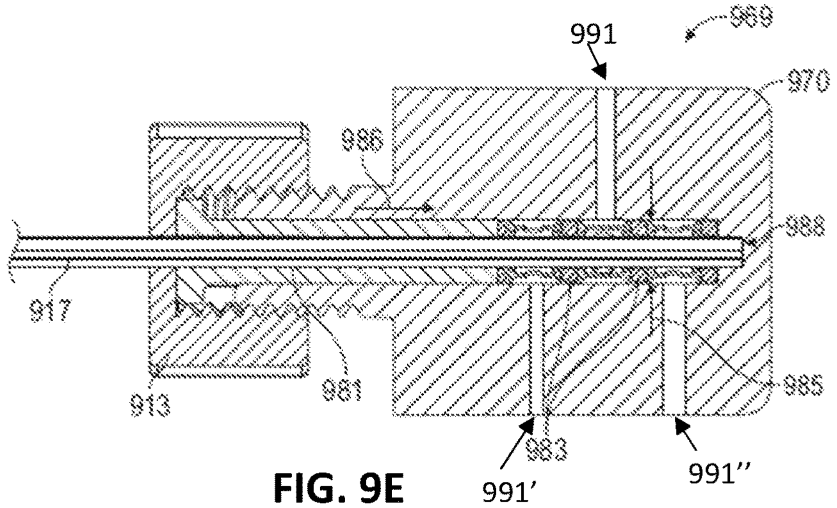
FIG. 9E is a sectional view through one example of a port adapter including a connector (e.g., a tuohy connector) for securing and sealing a multi-lumen catheter (e.g., an internal sheath configured as a multi-lumen catheter) as described herein.
Figure 9D:
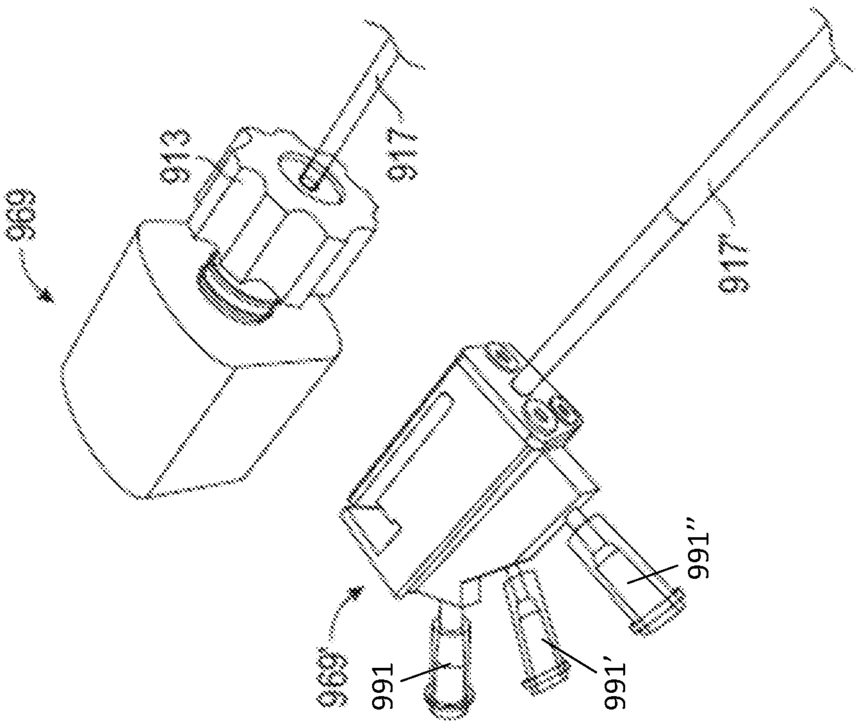
FIGS. 9C-9D show examples of port adapter manifolds that may be used as described herein.
Figure 9C:
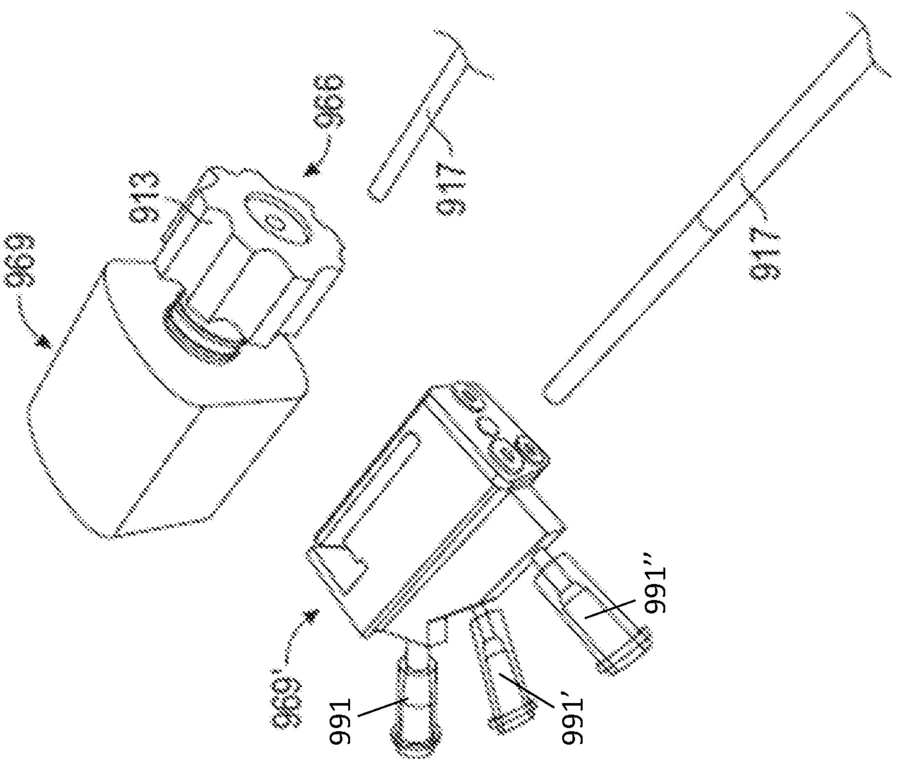

FIGS. 9C and 9D illustrate two examples of port adapters 969, 969' before (FIG. 9C) and after (FIG. 9D) insertion of the multi-lumen catheter forming an internal sheath of an endoscope sheath device. In FIG. 9C, similar to that shown in FIG. 9A, the first port adapter 969 is configured so that the multi-lumen catheter 917 may be inserted into the inlet 966 and may easily slide all the way until the distal end of the multi-lumen catheter is reaches the back (e.g., a stop 988) in the port adapter, as shown by the cross-sectional view of FIG. 9E. In this example, the inside of the port adapter may be divided up into regions or zones corresponding to the number of lumen in the multi-lumen catheter. The regions may be separated by one or more gaskets 983. The multi-lumen catheter may include one or more openings or holes through the walls of the multi-lumen catheter into each of the lumen of the multi-lumen catheter that are arranged along the length, so that openings into a particular lumen of the multi-lumen catheter will fall within a particular range of distance from the end of the multi-lumen catheter so that, once inserted into the port adapter, all of the holes corresponding to the particular lumen will be within a corresponding region or zone, as described in FIG. 9A.

Any of the port adapters ("port adapter manifolds") described herein may include one or more valves configured to control passage of fluid through the lumens of the multi-lumen catheter. Alternatively or additionally each port adapters may include a plurality of fluid line connectors 991, 991', 991", wherein each connector is configured to be coupled to a fluid line (liquid fluid line, suction line, etc.).

As the multi-lumen catheter (e.g., a multi-lumen channel liner) enter the receptacle manifold 970 of the port adapter, it may face high compression loads as, to seal, the O-ring inner diameter would be less than the outer diameter of the multi-lumen catheter. Although such a tight fit may help form the radial seals from the O-rings, this may lead to buckling of the multi-lumen catheter. The example port adapter 969 shown in the top of FIGS. 9C and 9D and in cross-section in FIG. 9E may avoid this problem by increasing the radial clearance of the O-rings and applying force to squeeze the O-rings down by axially compressing the component stack (e.g., the gasket stack), which translates into the requisite radial compression of the seals against the multi-lumen catheter. This motion (e.g., axial advancement by rotating a thread translating into a radial squeeze) is similar to what is done with a device at the back of a catheter (typically to adjust the back-end seal against a guidewire) by a tuohy (e.g., a Tuohy Borst adapter).

In the port adapter 969 shown in FIGS. 9C-9E, the gaskets 983 forming a seal between each of these separate zones may be o-shaped rings that have an inner diameter that may be larger than the outer diameter of the multi-lumen catheter. This may allow easy insertion of even very flexible or multi-lumen catheters and may help ensure full insertion of the multi-lumen catheter. As shown in FIG. 9E the port adapter may include a compression mechanism, such as a tuohy connector for securing the multi-lumen catheter within the port adapter. For example, the knob 913 may be twisted clockwise to compress the gaskets in the gasket stack (e.g., receptacle manifold) onto the multi-lumen catheter; tightening the knob drives a pusher 981 into the receptacle manifold (e.g., stack) of gaskets 983, axially compressing them and therefore radially compressing them 985, and tightening them over the multi-lumen catheter, forming seals. To remove the multi-lumen catheter, the knob 913 may be untwisted to release the compressive force 985 applied by driving 986 the pusher 981 into the gaskets of the receptacle manifold. In any of these devices and methods the port adaptor may be automated. For example, the port adapter may include one or more sensors so that insertion of the multi-lumen catheter could trigger a sensor at the end 988 of the port adapter, which may then automatically turn the knob or, with a linear actuator, simply slide it axially, thereby compressing the O-rings and creating a seal.

FIGS. 9C and 9D also illustrate a port adapter 969' similar to the port adapter 869 shown in FIGS. 9A-9B, which may include a catch or lock to secure the multi-lumen catheter within the port adapter. In any of the port adapters described herein the device may include a sprung pawl or catch-like means for securing the multi-lumen catheter within the port adapter. The port adapter may be one-way or releasable.

Figure 12:
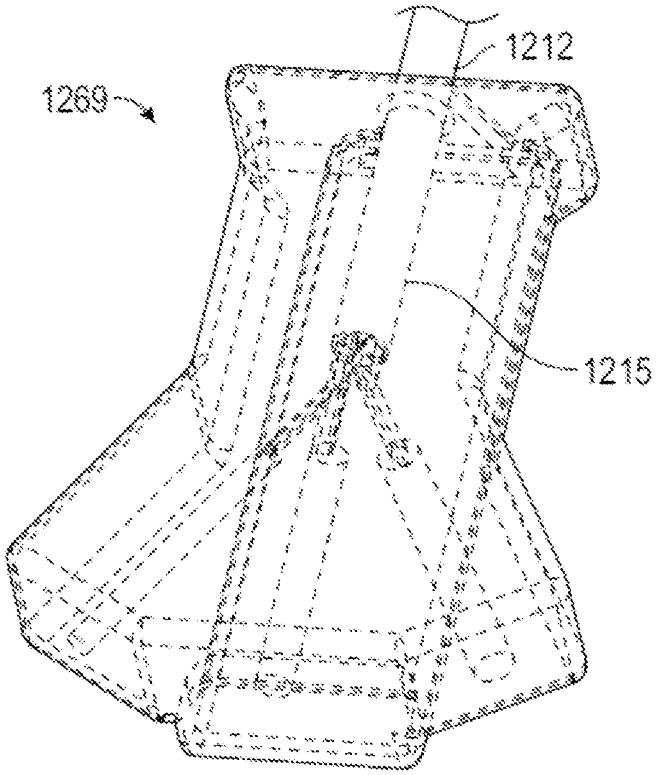
FIG. 12 is an example of a port adapter for coupling to a proximal end of a multi-lumen catheter forming an internal sheath.
Figure 13:
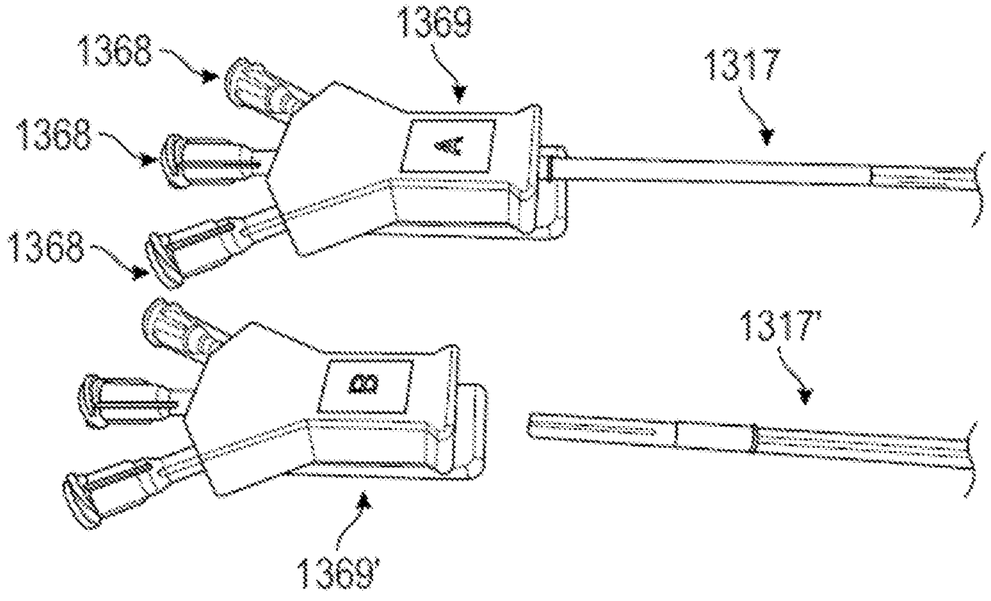
FIG. 13 shows an example of a port adapter for coupling to a proximal end of a multi-lumen catheter forming an internal sheath.

FIG. 12 illustrates an alternative port adapter 1269. In FIG. 12, the port adapter uses a face seal strategy. A male connector 1212 inserted into the female connector 1215. Each lumen in the male connector (three of them in this illustration) is fed by its own separate supply channel. The supply channels seal to the end of the male connector via a face seal so that there is no cross transmission between the channels. FIG. 13 shows another example of this type of port adapter. In this example, the face of the multi-lumen extrusion internal sheath may align each channel with a port, which may require rotational orientation of the input tube. In any of these examples, the shaft of the internal sheath 1212 may be keyed to guide orientation of the internal sheath relative to a port connector.

In FIG. 13, the internal sheath 1317 engages with the port adapter 1369 in a keyed manner so that the internal lumen may each engage a connector in the port connector that may seal to opening at the distal end of the internal sheath to permit access into and out of the lumen within the internal sheath. In the example shown in FIG. 13, the upper port connector 1369 is shown engaged with the internal sheath 1317, while the lower port connector 1369' is not engaged with an internal sheath 1317'. Each port connector includes three standard connectors 1368 that may be coupled to tubing for applying/removing material.

Figure 14:
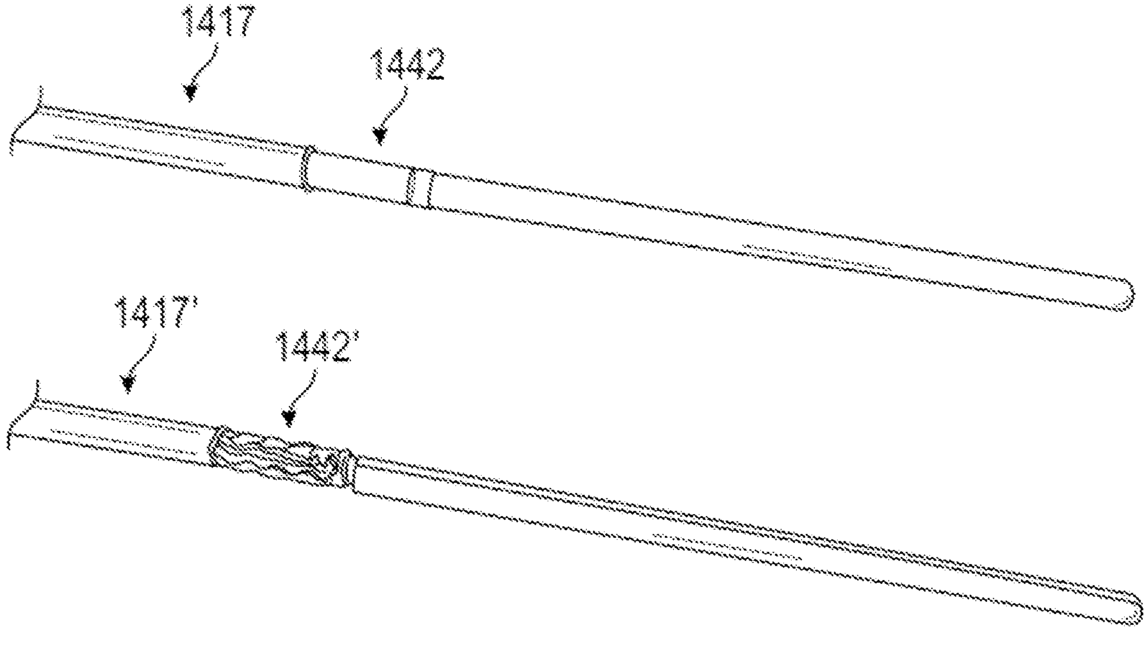
FIG. 14 illustrates a proximal end of an internal sheath including a crimping region to seal off the internal sheath before removing the endoscope from the sheath assembly.

As mentioned above, before removal of the sheath assembly, the internal sheaths may be blocked to prevent contamination. The internal sheath(s) may be sealed off by any appropriate manner, including thermal (e.g., melting with forces applied by heated dies), mechanical (e.g., crimping, pinching, stapling, etc.), or the like. FIG. 14 illustrates a crimp-based sealing method. A crimp 1442 may be included on the internal sheath, preferably near the proximal end region. This crimp 1442 may be crimped shut after a procedure. The compressed crimp 1442' seals the sheath to prevent contaminated fluids from leaking out of the sheath, and when compressed the crimp is smaller in diameter than the outside diameter of the internal sheath 1417, so that it can be pulled through. The internal sheath 1417 can then be wiped clean and removed by pulling it through the endoscope without contaminating the endoscope.

Figures 10A, 10B, 10C:
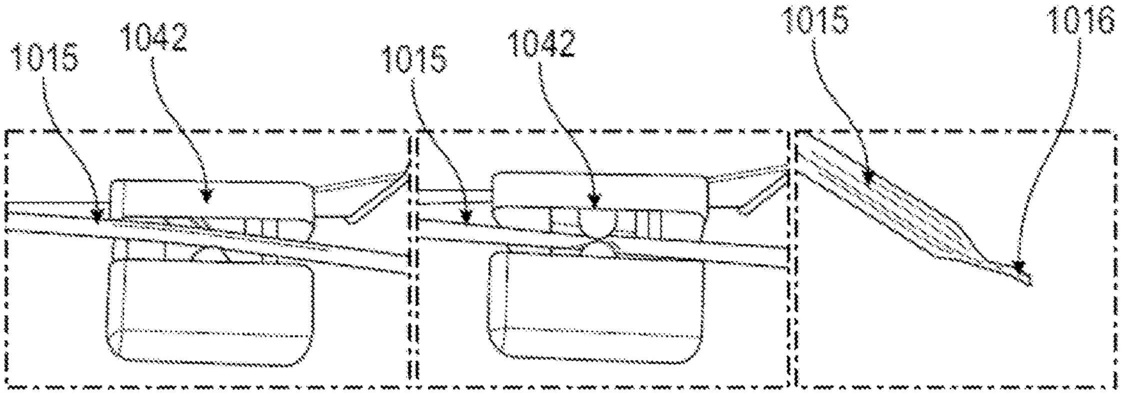
FIGS. 10A-10C illustrate one example of sealing a proximal end of an internal sheath.

Returning now to FIGS. 10A-10C, these figures illustrate an alternative to crimping in which an internal sheath 1015 is sealed by heat sealing after a procedure. Heat sealing hygienically seals the internal sheath keeping any contamination safely inside the sheath. Internal volume of the tube can locally be driven to zero, which greatly reduces the potential for contamination. Heat sealing could further reduce any problem associated with any potential residual matter. In FIG. 10A the internal sheath 1015 is inserted into the heat-sealing device 1042, so that heat (and/or mechanical pressure) may be applied as shown in FIG. 10B to melt the material of the internal sheath, resulting in a seal 1016 as shown in FIG. 10C. After heat sealing, or as part of the heat sealing operation, the internal sheath can be cut and withdrawn back through the endoscope with no risk of contamination. Heat sealing of tubes with liquids in them is routinely done for blood sampling and other applications.

The use of internal sheaths for the sheath assembly where the internal sheaths themselves become the supply lines and working channel for the endoscope and still run through the internal volume of the endoscope may be advantageous. The external sheath part cannot only bend side to side, but also is flexible enough to support extension and retraction of the endoscope relative to the outer tube while maintaining a physical barrier to contamination.

Figure 15A:
FIGS. 15A-15D illustrate an example of a system including an endoscope (FIG. 15A), a sheath device (FIG. 15B), and an outer endoscope (FIG. 15D).
Figure 15B:
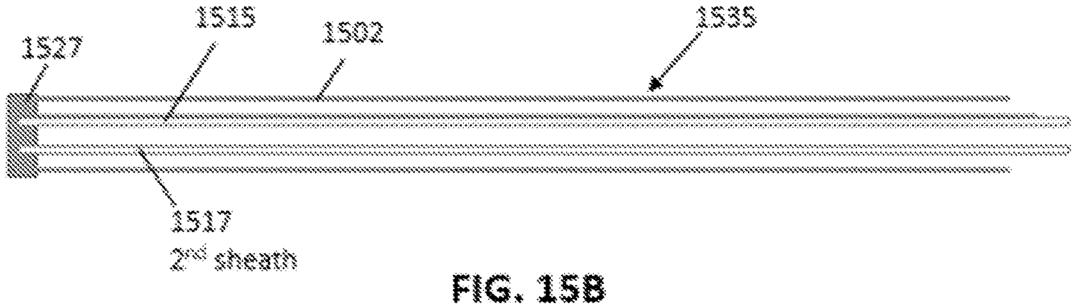

Any of the endoscope sheath devices described herein may be used with nested endoscopes, either robotic or manual. For example an endoscope sheath device may be part of a system including an elongate outer endoscope and an inner endoscope arranged in a telescoping arrangement. The endoscope sheath device may be configured to fit over both the inner endoscope (that is fit into the outer endoscope) and the outer endoscope. Alternatively, as shown in FIGS. 15A-15D, the endoscope sheath device may be configured to fit over the inner endoscope and then inserted through the outer endoscope. FIG. 15A shows an example of an inner endoscope 1500 that, in this example, includes a first lumen 1501 and a second lumen 1505. FIG. 15B shows an example of an endoscope sheath device 1535 that may be used with the first (inner) endoscope. The endoscope sheath device includes a cap 1525 to which an elongate, flexible and tubular external sheath 1502 is sealed. A pair of internal sheaths, e.g., a first internal sheath 1515 and a second internal sheath 1517 extend within the length of the external sheath and are also sealed at their distal end regions to the cap so that the cap is open to allow passage into the lumen of the first 1515 and second 1517 sheaths.

Figure 15C:
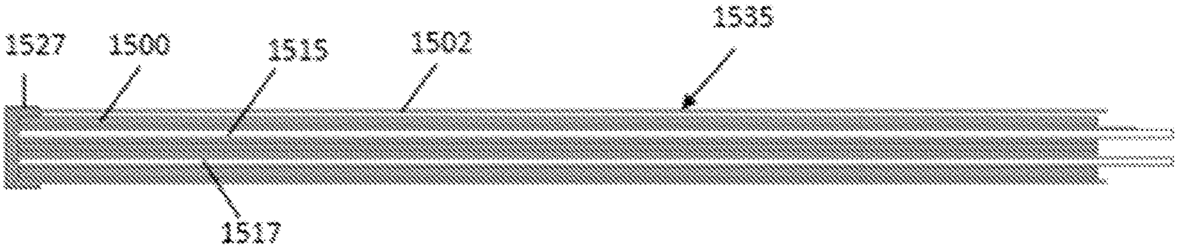

FIG. 15C shows the endoscope sheath device 1535 of FIG. 15B attached over the inner endoscope of FIG. 15A. the cap may be attached (e.g., latched, friction fit, snapped on, etc.) to the distal end region of the endoscope 1500. In FIG. 15C the endoscope may be inserted into a body without risk of contamination, because the endoscope sheath device forms a complete barrier for both the outer surface and the inner (luminal) surfaces of the endoscope. The endoscope sheath device does not prevent or limit (and may instead enhance) the operation of the lumen of the endoscope, while still maintaining a fluid-impermeable contamination barrier to prevent contamination. Thus, the inner endoscope may be reused after a procedure by removing the endoscope sheath device, as described herein, without contaminating the endoscope. For example, the internal sheaths may be sealed (by crimping, or otherwise) at their proximal end and the external sheath may be inverted over itself by pulling it proximally partially or completely, preventing contamination and trapping any contaminants within the inverted sleeve of the sheath.

The cap may include one or more transparent sections to allow use of the camera and illumination built into the endoscope 1500. The endoscope sheath device's two internal sheaths may include lumen that may be used to pass material through the endoscope by passing though the cap into the lumen of the internal sheaths. A multi-lumen catheter may be used for one of or both of the internal sheaths, and may include sub-lumen for irrigation, tip wash and/or insufflation lines, for example, which may be directed by the shape of the tip region, which may include a deflector, nozzle, etc. For example, the tip may include a tip wash deflector or nozzle that may direct fluid from the tip wash sub-lumen of the multi-lumen catheter forming one of the internal sheaths to direct fluid to clean a window for the camera on the tip. As described herein, in some examples the tip may include illumination built into the cap instead of being on the endoscope.

Figure 15D:
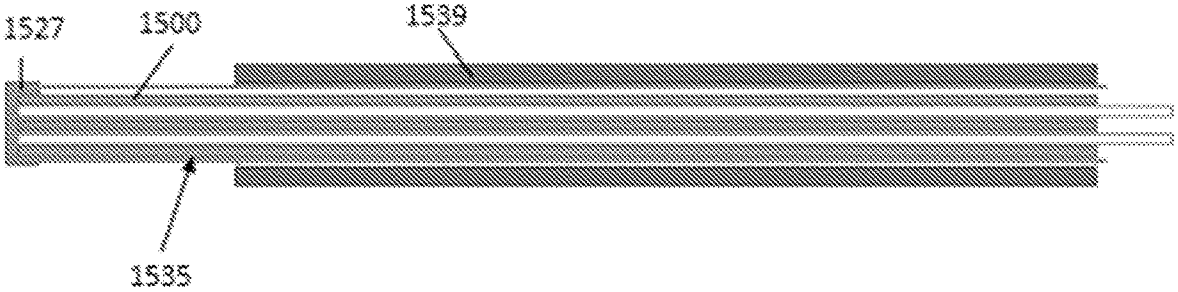

FIG. 15D also illustrates the use of the endoscope with the applied endoscope sheath device with a second (e.g. outer) endoscope. In FIG. 15D the outer endoscope 1539 includes a lumen into which the inner endoscope covered by the endoscope sheath device may be inserted. In this example, the outer endoscope 1539 may be configured to act as an overtube, and may be single-use or limited use (e.g., disposable). The endoscope 1500 may be a removable endoscope core that may be reusable. The endoscope 1500 may include one or more cameras, illumination, pull cables (e.g., for steering the distal end region), coil pipe assembly, bending section, etc. As mentioned, the endoscope may be inserted into a fresh endoscope sheath device and secured in place by coupling the cap to the distal end region of the endoscope and in some examples inserting into the outer endoscope for performing a procedure.

In general, these methods and apparatuses may therefore replace components having lower durability before each new procedure, including replacing the endoscope sheath device and any associated hydrophilic coatings on the outside (e.g., configured to be positioned between the outer endoscope/overtube and the inner endoscope), while the inner endoscope can be reused multiple times. The inner endoscope may therefore be hygienically draped by the endoscope sheath device, so that it can be reused without requiring high level disinfection (HLD). The inner endoscope may be fully shielded from any exposure to water and contamination which facilitates simpler and more cost-effective design and construction. Further, the patient is therefore fully shielded from the second endoscope, potentially simplifying biocompatibility and cleaning requirements for the endoscope. The use of the endoscope sheath device may also extend the lifetime of the endoscope, including some of the costliest components of the endoscope, such as the camera and bending section components. This configuration may also permit the removal and replacement of the inner endoscope during a procedure, while leaving the outer endoscope/overtube in place. These methods may also accommodate utilization of the exterior surface of the overtube for adding accessories, such as external working channels, as described in reference to FIGS. 16A-16B.

Figure 16A:
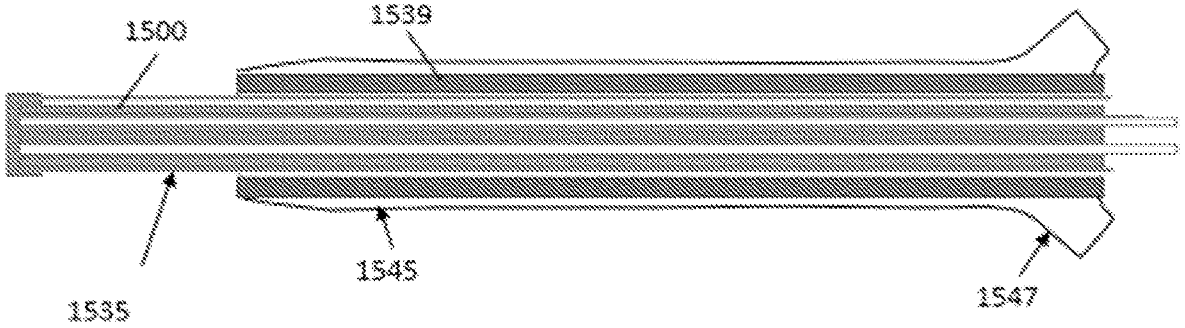
FIGS. 16A-16B illustrate a system including a sheath device, a separate outer rigidizing device and external working channels.

In general, any of the apparatuses described herein may include the use of external working channels over the endoscope sheath device and/or over an endoscope used in conjunction with the endoscope sheath device. FIG. 16A illustrates an example in which the apparatus shown in FIG. 15D (including an endoscope 1500, endoscope sheath device 1535 and outer overtube 1539) also includes external working channel 1545. Examples of external working channels may be found, for example, in U.S. patent application Ser. No. 17/940,906, titled "EXTERNAL WORKING CHANNELS," and filed on Sep. 8, 2022, and U.S. patent application Ser. No. 18/000,062, titled "RIGIDIZING DEVICES," and filed on May 26, 2021, each of which is herein incorporated by reference in its entirety.

Figure 16B:
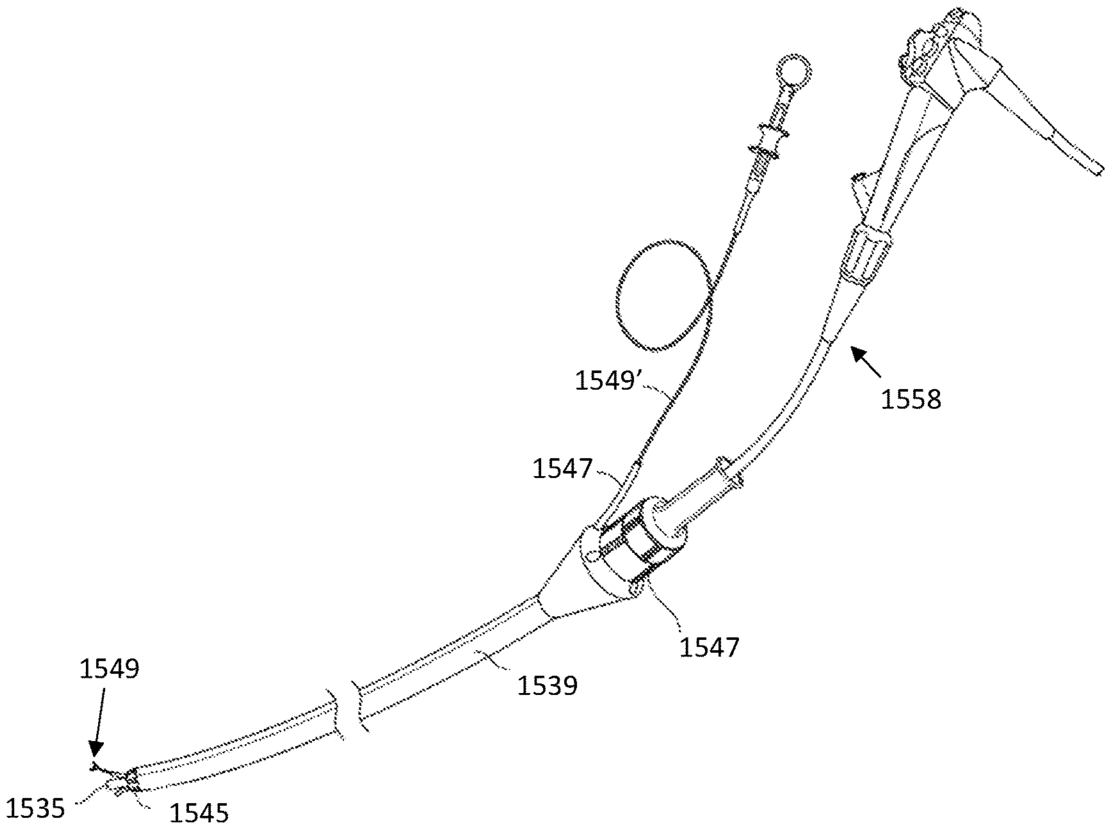

The one or more external working channels 1545 may be expandable from the outside surface of the outer endoscope 1539 and may include a proximal insertion guide region 1547 for inserting one or more device through the external working channel. FIG. 16B shows an example of a system including an inner endoscope covered by an endoscope sheath device 1535 such as that described in FIGS. 15A-15D, that is slidably arranged within the outer endoscope 1539. As mentioned, the outer surface of the endoscope sheath device may be coated with a hydrophilic coating to assist in axial movement between the outer and inner endoscopes. The system shown in FIG. 16B also includes external working channels 1545 configured as a cover over the outer endoscope that includes a proximal insertion guide 1547. In FIG. 16B a tool 1549, 1549' is shown inserted through the insertion guide 1547 passing into the working channel of the external working channel and extending distally from the distal end of the outer endoscope. The proximal end of the inner endoscope 1558 is shown extending from the proximal end of the outer endoscope. In this example, the internal sheaths (not shown) may extend proximally and may couple to, e.g., a source of aspiration, fluid, insufflation, etc. These working channels can co-exist with a sheathing system, such that the underlying endoscope maintains its cleanliness, even as tools go through its working channels and tools go through the external working channels.

In any of these examples the external working channels may be mounted on the overtube, as shown in FIG. 16B, e.g., using an overtube as described in FIG. 4A. In this case, the working channels may be disposed of out after each procedure, together with the overtube and the distal external sheath.

In some examples the external working channels may be mounted on the external sheath of the endoscope sheath device. For example one or more external working channels (including expandable working channels) may be incorporated into the external sheath, such as the full length external sheath, which may fit over the outside of the endoscope or endoscope assembly (e.g., FIG. >4C). In this configuration the working channels may be disposed of after each procedure together with the full length external sheath, but without requiring disposal of the overtube (which is protected under the full length of the external sheath).

Any of the endoscope sheath devices described herein may be configured as rigidizing endoscope sheaths. The endoscope sheath devices may be rigidized in any appropriate manner, including, but not limited to, pressure rigidizing devices. For example, the endoscope sheath devices describe herein may include a rigidizing external sheath configured to extend over an endoscope and may include a rigidizing layer comprising multiple strand lengths that cross over each other and a compression layer that is configured to apply force to the rigidizing layer when pressure is applied in order to rigidize the rigidizing external sheath from a flexible configuration to a rigid configuration.

For example, FIGS. 17A-17D illustrate a system including an endoscope 1700, having one or more lumens (e.g., in this example, a first lumen 1701 and a second lumen 1705), and a rigidizing endoscope sheath device 1735. The rigidizing endoscope sheath device includes a cap 1727 that is configured to attach to the distal end region of the endoscope 1700 and includes one or more internal sheaths (in this example, a first internal sheath 1715 and a second internal sheath 1717) that are configured to fit within the endoscope 1700. The rigidizing endoscope sheath device also include a rigidizable external sheath 1702. The rigidizable external sheath 1702 is a tubular sheath that is sealed to the cap 1727. The external sheath 1702 may have an inner diameter that is slightly greater than the outer diameter of the inner endoscope 1700.

The rigidizable external sheath 1702 may include a rigidizing layer or region that engages with a compression layer (which may be or may include a bladder) that applies force to the rigidizing layer to rigidize the rigidizing layer or in some cases, to de-rigidize (e.g., release from rigidization) the rigidizing layer. In some examples, these rigidizable external sheaths 1702 may include a rigidizing layer that could include a braid, knit, woven, chopped segments, randomly distributed or randomly oriented filaments or strands, engagers, links, scales, plates, segments, particles, granules, crossing filaments, or other materials forming the rigidizing layer. For example, the rigidizing layer may comprise multiple strand lengths or strand segments that cross over each other (e.g., as part of a braid, knit, woven, etc.); the compression layer may apply force to drive the crossing strand lengths or strand segments against each other. In some examples the rigidizing layer may be a braided layer, however any of these apparatuses may instead or in addition include a general rigidizing layer comprising crossing strand lengths or strand segments. The examples of rigidizing apparatuses described herein may use pressure (positive pressure) and/or negative pressure to selectively and controllable rigidize. In some examples the method described herein may be used with any appropriate rigidizing apparatus.

Figure 17A:
FIGS. 17A-17D illustrate an example of a system including an endoscope (FIG. 17A), a rigidizing sheath device (FIG. 17B), and an outer endoscope (FIG. 17D).
Figure 17B:
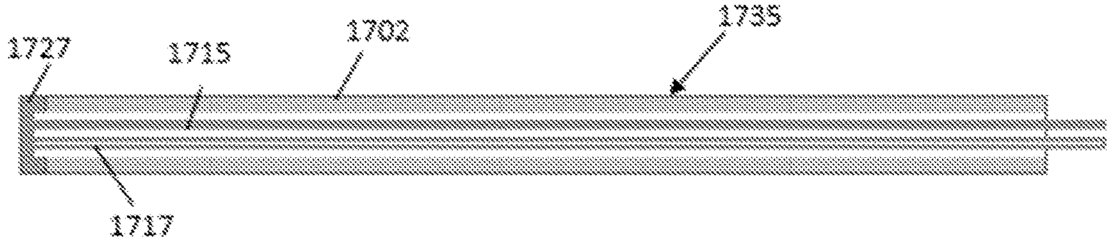
Figure 17C:
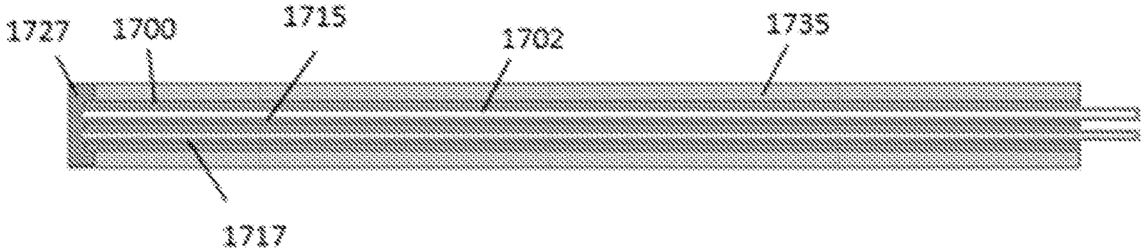

FIG. 17C shows an example of the assembled inner catheter 1700 and the rigidizing endoscope sheath device 1735. The inner rigidizing sheathes are inserted into the lumen of the endoscope, the cap is coupled to the distal end of the endoscope, and the outer rigidizing endoscope sheath 1702 extends over the outer surface of the endoscope.

Figure 17D:
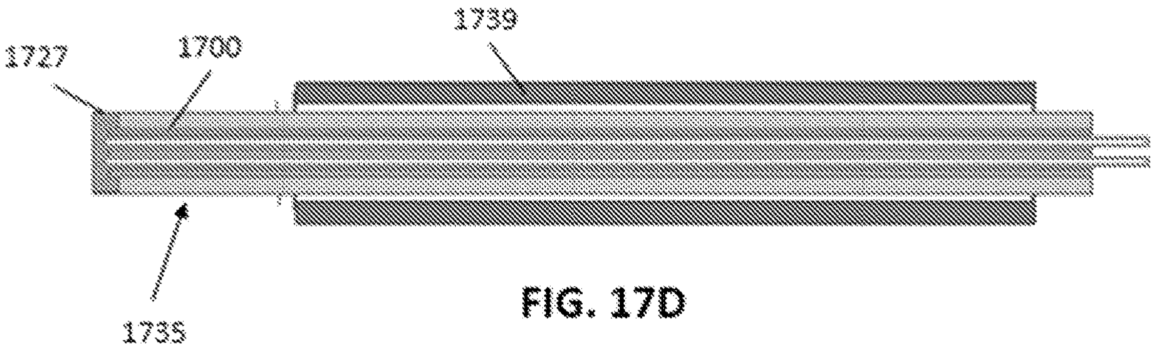

Any of these systems may also optionally include a second, outer, endoscope 1739, as shown in FIG. 17D. Thus, these apparatuses may be used in a nested configuration. The outer endoscope may also be rigidizing in some configurations.

As mentioned, the outer endoscope 1739 (e.g., overtube) may be one-time/disposable, and/or may be reusable (e.g., by cleaning or by sheathing). Similarly, the endoscope sheath device may be single use/disposable or may be reusable (e.g., by cleaning). The endoscope may be reusable, and may include, e.g., a camera, illumination, pull cables, coil pipe assembly, bending section, etc. The inner endoscope may be inserted into a fresh endoscope sheath device and secured in place for a procedure, and then unsecured and removed after a procedure.

In any of the apparatuses and method of using and making them described herein, the internal sheath(s) may be configured to both prevent contamination and to pass one or more materials or objects. In general, the internal sheaths are typically tubular sheaths that are sealed so that the distal outer edge is sealed circumferentially within an opening through the cap. Further the internal sheath(s) may be generally stiffer than external sheath and may sufficiently stiff so that they may be threaded into the lumen of the catheter. Further, the internal sheath may be sufficiently stiff so that it can allow unobstructed passage of a material when acting as an internal working channel (e.g., when the internal sheath is acting as a working channel liner). In some cases, however, particularly when used with a steerable endoscope, such as the one shown in FIG. 18, the internal working channel must be sufficiently flexible to allow bending of the endoscope.

Figure 18:
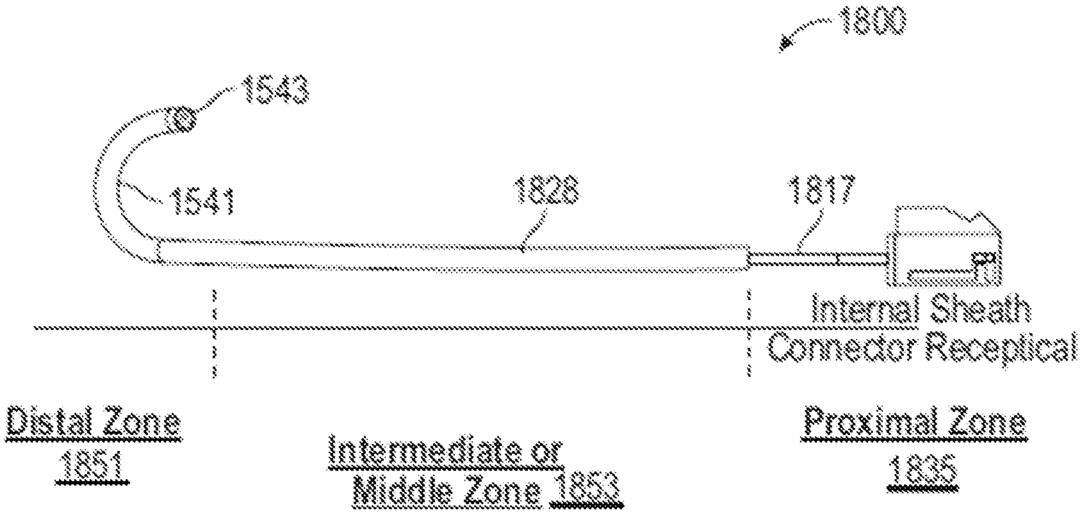
FIG. 18 illustrates an example of a sheath over an endoscope having a steerable distal end region.

For example, in endoscopes such as the one shown in FIG. 18, have different bend radiuses at the different zones. The distal end region ("distal zone") 1851 may be highly flexible, as shown, as the distal tip 1543 of the endoscope, to which the cap of the endoscope sheath device may be coupled may be steered by bending a bending section 1541 of the endoscope. The endoscope may be steered or bent by any appropriate technique or structure, including tendons/pullwires, etc. The bending of the tip region may be particularly challenging for the internal sheath, as bending beyond a particular radius of curvature may result in pinching or collapse of the lumen of the internal sheath. Thus, these apparatus may include tube reinforcement—particularly in the distal end region corresponding to this distal zone 1851. However, it should be appreciated that other regions may also be reinforced, including the intermediate or middle zone 1853, which may extend to, or almost to, the proximal end of the catheter. The proximal zone 1835 may include the extension of the internal sheath 1817 beyond the catheter and/or the external sheath 1828 and may extend, for example, to a port adapter 1868.

In some examples, the entire endoscope may be highly flexible, and the internal sheaths may be highly flexible to match. To achieve both high flexibility and sufficient stiffness/radial strength to prevent collapse and allow easy insertion of the internal sheath(s), in any of these apparatuses the internal sheath may be reinforced. Any appropriate reinforcement and extent of reinforcement may be used. For example, the internal sheath may be reinformed by one or more coils that are wound helically around and/or within the internal sheath to prevent localized buckling during tight curvature of bending (e.g., bending having a radius of curvature that is less than, e.g., 30 mm, less than 20 mm, less than 15 mm, less than 10 mm, less than 7.5 mm, less than 5 mm, less than 4 mm, less than 3 mm, less than 2 mm, etc.).

Figure 19A:
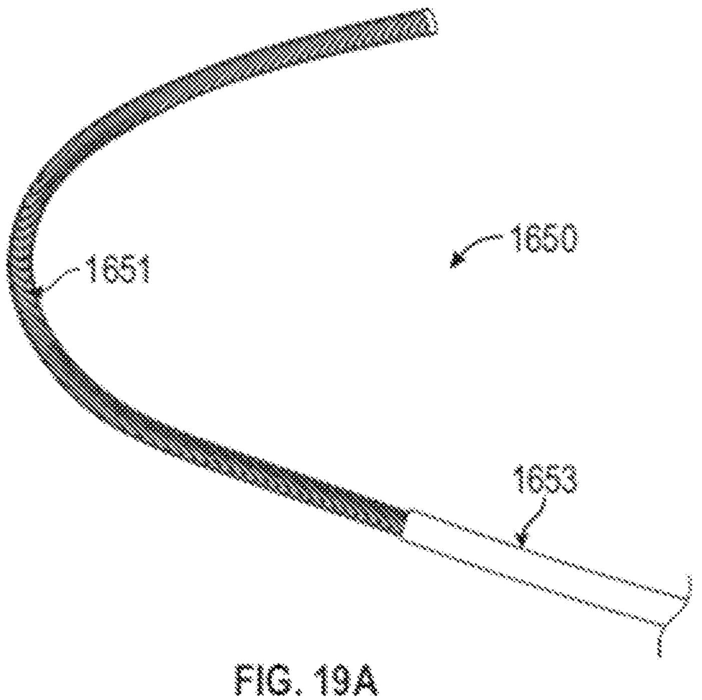
FIGS. 19A-19B illustrate examples of internal sheaths that are reinforced over a portion or all of their length.
Figure 19B:
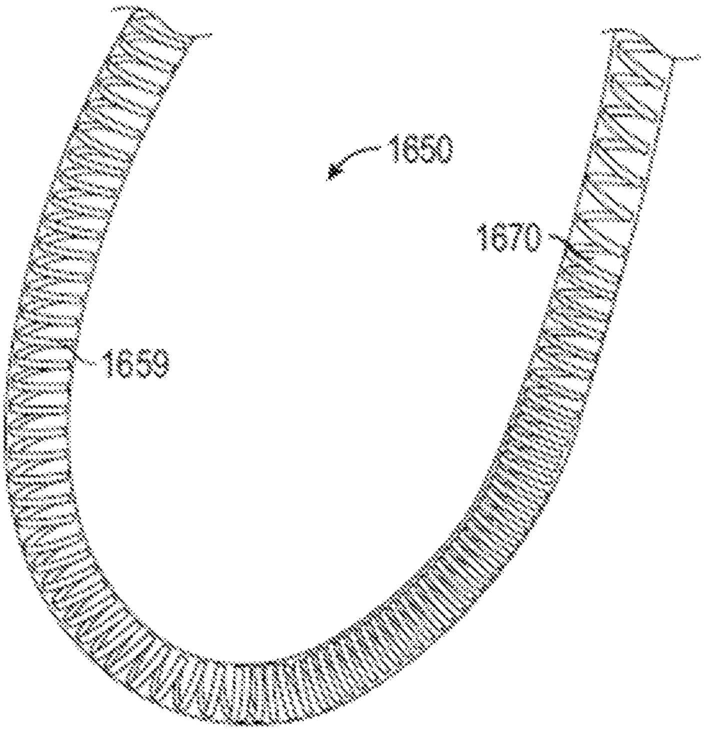

FIG. 19A illustrates an example of a first tubular internal sheath. This example is a single-lumen internal sheath, which may be referred to as a tube liner, as it lines the lumen of the endoscope. In FIG. 19A the internal sheath 1650 includes a reinforced distal region 1651 and an un-reinforced middle region 1653. The reinforced distal region 1651 may be reinforced by including an inner coil wound tube or by forming of a more flexible, yet collapse or buckling-resistant material (e.g., polymeric material). In some examples, as shown in FIG. 19B the entire length of the internal sheath 1650 is reinforced by a coil. Other internal sheaths may include more than one lumen and may be reinforced as well. In some example, multi-lumen internal sheaths may not need to be reinforced, as the division of the inner lumen into the multiple lumens may provide internal reinforcement.

The internal sheath in some examples is formed of an intermediate durometer elastomeric by, e.g., extrusion. A slip additive may be included to help make the internal sheath slippery so that it slides in easily, e.g., within the lumen of the endoscope, and relative to tools that pass within its inner diameter. In some examples the internal sheath may be formed as a composite structure. For example, a laminated coil wound tube may be used, with the coil pitch changing along the length, and the coils may be formed from a flat wire. The flat wires may be wound more densely in the distal zone to prevent buckling as the bending section is brought through a tight radius of curvature. The matrix material forming the body of the internal sheath may be a low durometer elastomer (70A urethane) material. The inner surface of the tubular internal sheath may have a hydrophilic coating so that tools can slide easily. This can make the sliding far superior to that possible with standard PTFE tubing. For example, a reusable scope with the standard PTFE tube may allow a tool to be inserted and perform two complete wraps (e.g., 2*360 degrees). With a hydrophilic coating, this can be increased to up to six wraps (e.g., 6*360 degrees). The drag in this situation scales exponentially, particularly in long, bend/bendable tubes, thus this is a major reduction is drag, and an advantage of the endoscope sheath devices described herein. The resulting low drag may enhance the tactile feel for the instrument. This is another example of how a sheathed system can outperform a reusable system.

Thus, the internal sheaths may be reinforced as described herein, and/or may be formed of a material having sufficient properties (e.g., wall thickness, stiffness in bending, bucking in bending, buckling along length, etc.) to prevent pinching or collapse when manipulating the endoscope. In general, the interior sheath may be made of the same material as the external sheath, or they may be made of different materials. Examples of appropriate materials for the internal sheath may include, but are not limited to: polytetrafluoroethylene (PTFE), fluorinated ethylene propylene (FEP), perfluoroalkoxy (PFA), high-density polyethylene (HPDP), low-density polyethylene (LDPE), polyether block amide (e.g., Pebax™) expanded Polytetrafluoroethylene (EPTFE, e.g., Fluroflex™), Urethane, etc. These materials may be extruded and may be combined with other materials, such as, for example, with a heat set metal coil, coil wound with round wire, flat wire, etc. Examples of materials for the external sheath may include (but are not limited to): LDPE, polyolefin plastomers, nylon, composite materials (for example, thin films laminated with a urethane, including high performance fibers inter-dispersed (for example, Dyneema, Technora, carbon fiber, fiberglass, etc.), silicone, and urethane. These may be manufactured by multiple methods, including, but not limited to: extrusion, blow molding (including bellows designs), lamination, heat sealing.

In general, the endoscope sheath devices described herein may include a tip that includes features that permit the endoscope sheath device to easily and effectively secure to the distal end region of the endoscope, the permit the external sheath and the internal sheath(s) to form a seal with the cap, and that may include integrated features to assist in the functioning of the endoscope to which the endoscope sheath device is attached. For example, an endoscope sheath device may include a tip having any of the feature shown in FIG. 20A-20D, 21C, 22A-22C, 23A-23B, 24A-24B, 25, 26A-26B, 27A-27C, 28A-28D, 29A-29B, 30A-30B, 31A-31B, 32A-32B, 33A-33B, 34A-34B36A-36B or 38.

Figure 36A:
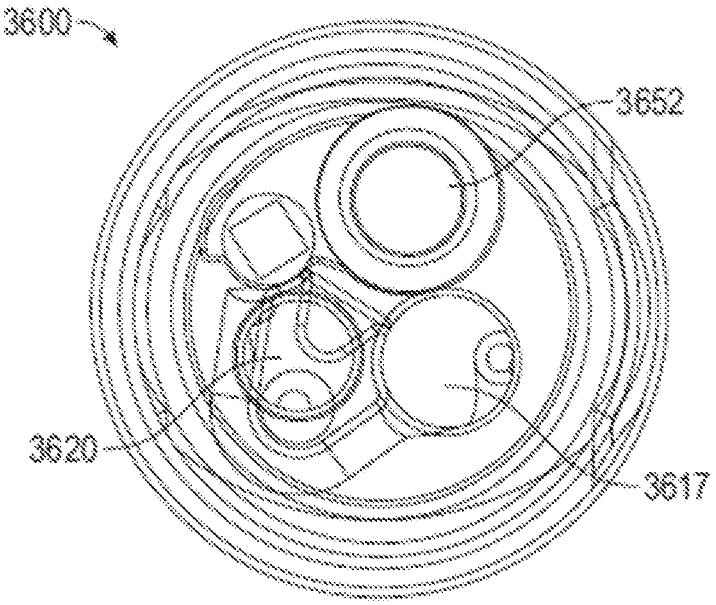
FIGS. 36A and 36B illustrate examples of a cap for an endoscope sheath device that includes an integrated optical lens as part of the cap.
Figure 36B:
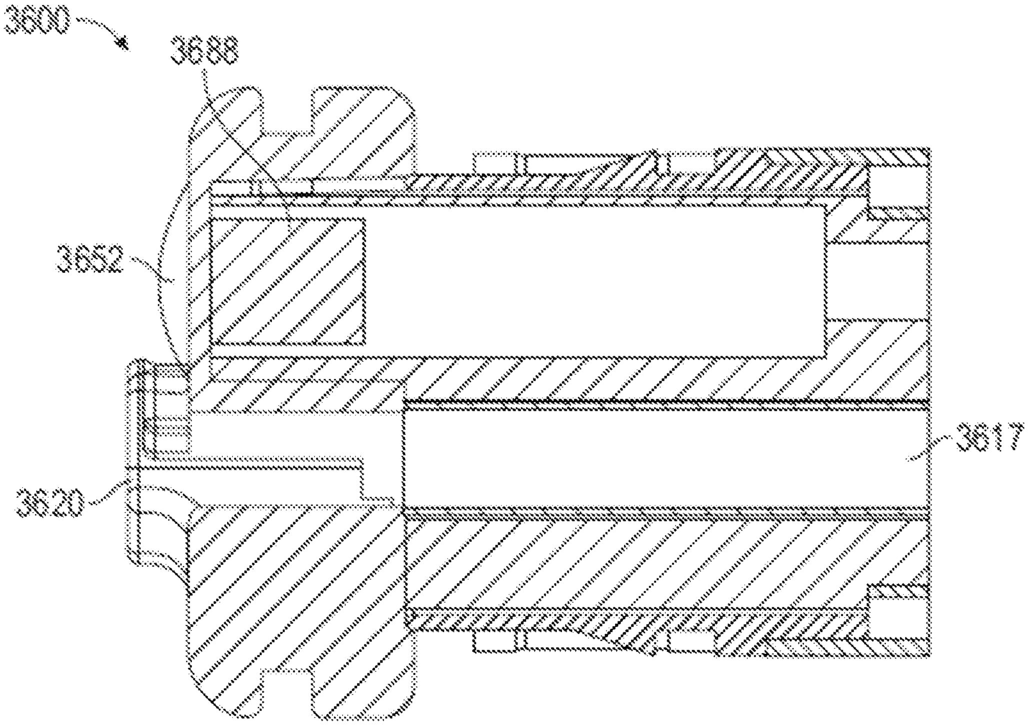

For example, FIGS. 20A-20D illustrate one example of a cap including features that may be included in any of the endoscope sheath devices described herein. The cap shown includes a distal face that may be all or partially transparent, and may include a transparent camera region 2026 through which a camera on the endoscope may image. As shown in FIGS. 36A-36B, in some examples the cap may include integrated lenses or cameras. In some examples the cap may further include a transparent light-passing region 2024 allowing transmission of light through the cap from the endoscope. The cap 2018 may also include one or more optical components (e.g. diffuser, lens, etc.) for modifying the illumination light. In some examples the cap may alternatively or additionally include one or more light sources, e.g., LEDs. The cap may include one or more openings corresponding to the internal sheath regions, including the opening into the lumen of the first internal sheath 2023 and/or the second internal sheath 2022. Any of these apparatuses may also include one or more flow directors or displacers 2020 that may direct (or re-direct) flow of one or more agents (e.g., wash solution, air, etc.) from the proximal end of the device. For example, the cap may include a wash nozzle or wash director outlet 2021 which may be part of the fluid displacer 2020 on the cap.

Figure 20A:
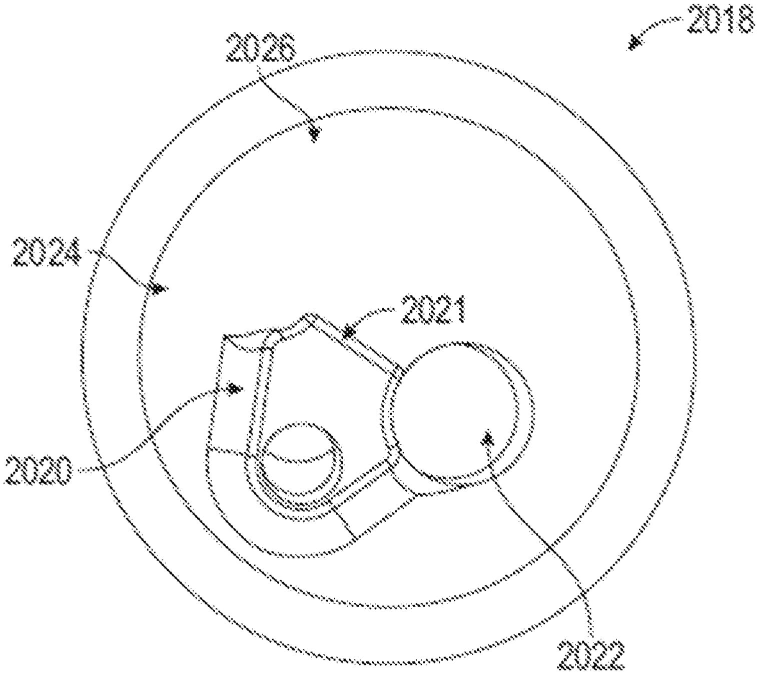
FIGS. 20A-20D illustrate an example of a cap for an endoscope sheath device.
Figure 20B:
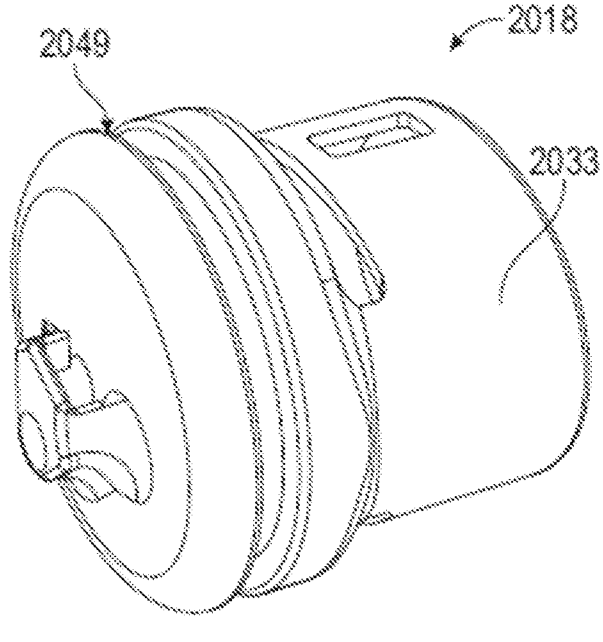

For example, FIG. 20A shows an end view of the cap in this example. FIG. 20A shows an end-on view of the cap. FIG. 20B shows a side perspective view, including a cylindrical mating region 2033 that may initially be oval, as shown in FIG. 20D. The oval-shaped mating region may, in an unconstrained configuration, have an oval cross-section, transverse to the long axis of the device. The side view of FIG. 20B also shows that the cap may include one or more regions for coupling with all or a portion of the cylindrical external sheath; in FIGS. 20B and 20C, the cap includes a recessed mating region 2049 into which the external sheath may be sealed, for example, with an elastic member (elastic retaining ring, not shown) and/or adhesive and/or a heat seal.

As shown in FIG. 20D the cap 2018 may include an oversized rim 2036 extending around the cylindrical mating surface 2033. FIG. 20D shows the inside of the cap region. Showing the recessed or cut-out inlets 2022, 2023 for receiving and sealingly bonding to the internal sheaths. The inside of the cap also includes a recessed region 2039 for receiving the optics from the endoscope (e.g., camera, lens, light director, etc.).

Figure 20C:
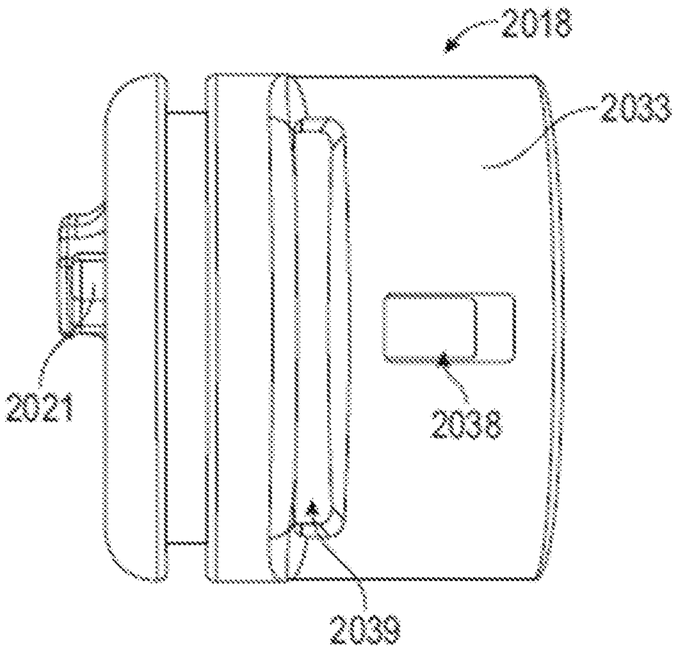
Figure 20D:
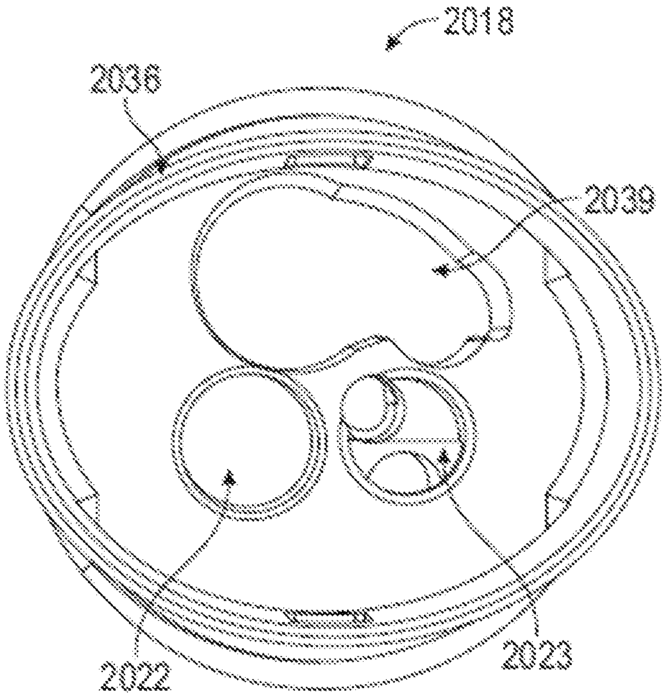

The end cap shown in FIGS. 20B-20D also includes a latch region 2038 extending through the mating surface that is configured to mate with a distal end of the endoscope, by compressing the mating surface from an oval resting cross-sectional configuration into a circular mating cross-sectional configuration. The latch 2038 may be formed in this example as an opening into which a protruding latching member, e.g., on the distal end region of the endoscope, may engage. Alternatively in some examples the protruding latching member may be on the cap and may engage with a latch opening on the distal end of the endoscope.

Any of these caps may also include one or more stress relief regions 2039, including stress-relief cutout regions, that may make it easier and more reliable to compress the cylindrical mating region 2033 (e.g., wall).

Figure 21C:
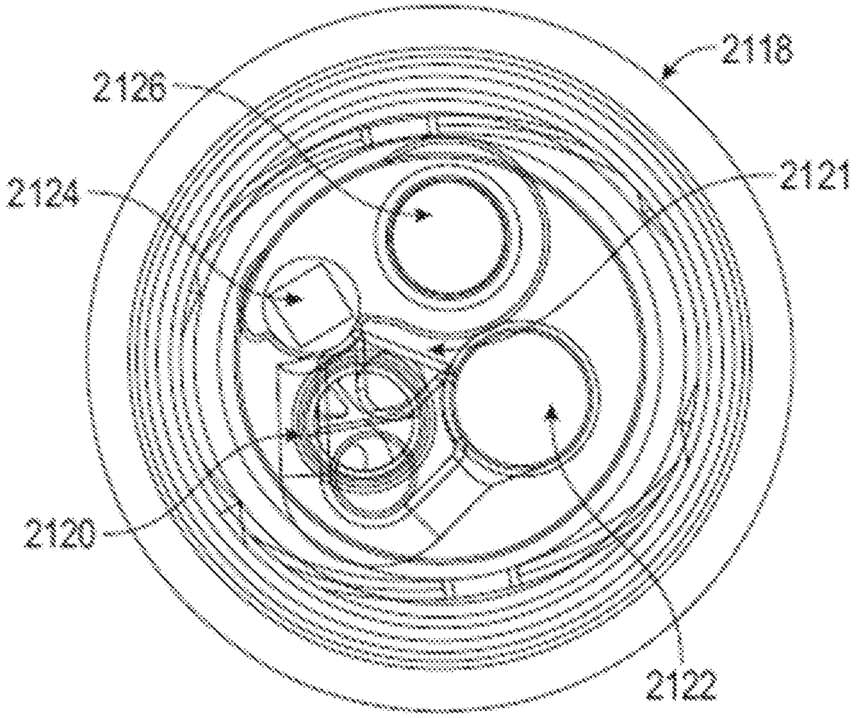
FIG. 21C shows an end view of the endoscope shown in FIGS. 21A-21B with a cap similar to that shown in FIGS. 21A-21B attached to the distal end region of the catheter.
Figure 21A:
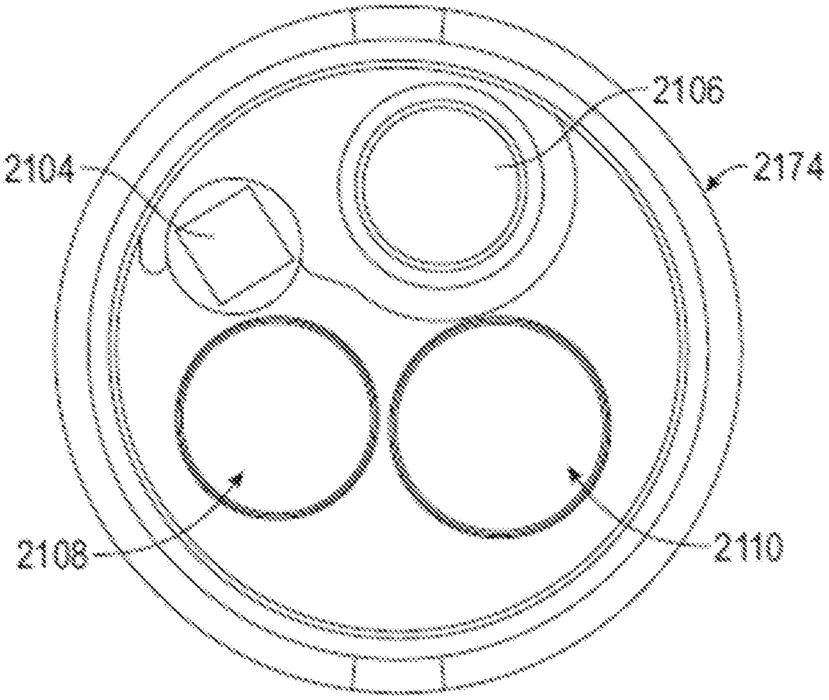
FIGS. 21A and 21B shows a distal end region of an endoscope configured to receive the cap of the sheath device shown FIGS. 20A-20D.
Figure 21B:
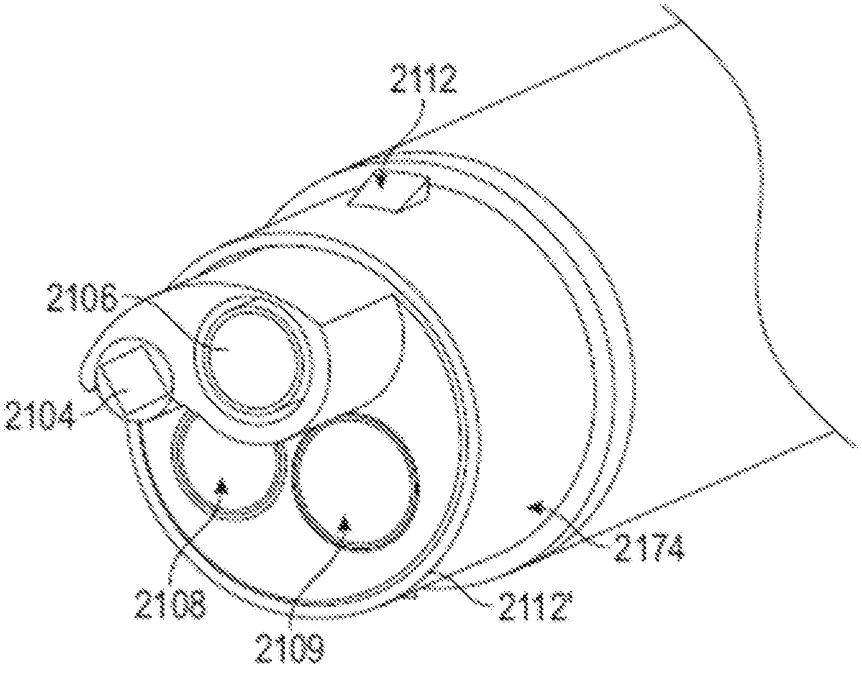
Figure 26A:
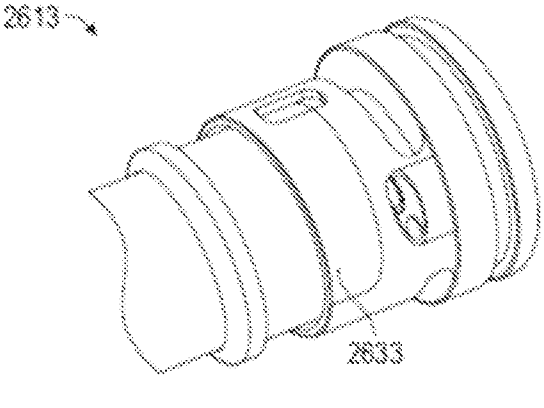
FIGS. 26A-26B illustrate attaching one example of a cap for an endoscope sheath; for convenience the inner and external sheath are not shown.
Figure 26B:
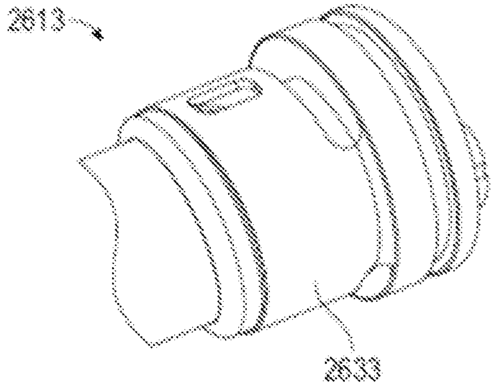

For example, FIGS. 21A and 21B show examples of the distal end of an endoscope including a camera 2106, light 2104, and first 2108 and second 2109 lumen through the endoscope. The endoscope in this example also includes an outer diameter surface 2174 on which the mating latch component (e.g., a ramped latch protrusion 2112, 2112' in FIG. 21B) is present. FIG. 21C shows a front view of the endoscope sheath device of FIGS. 20A-20D attached to a distal end of an endoscope. The cap 2118 in this example may be applied by first applying pressure (e.g., squeezing the cap) to circularize the oval mating wall then sliding it over the distal end and engaging the latches 2112 on upper and lower regions. This is illustrated in FIGS. 26A-26B. In this example, the cap 2613 includes a cylindrical mating surface 2033 that is formed in an (at-rest) oval cross-sectional shape. Transitioning from the oval cross-sectional shape to a more round shape matching the perimeter of the catheter may allow the endoscope sheath device to be slid onto the more circular endoscope distal end and mate with the latching components. Once pressure is released, the cap may return to a slightly more oval configuration, applying force to the hold cap onto the distal end region.

As in shown in FIG. 21C the cap may include one or more structures, such as a fluid displacer 2120 that may allow the cap to direct the flow of material (e.g., wash) from the lumen of the internal sheath. In FIG. 21C the internal sheath in this lumen of the catheter is a multi-lumen catheter partitioned into three regions: insufflation, wash and irrigation.

Figure 22A:
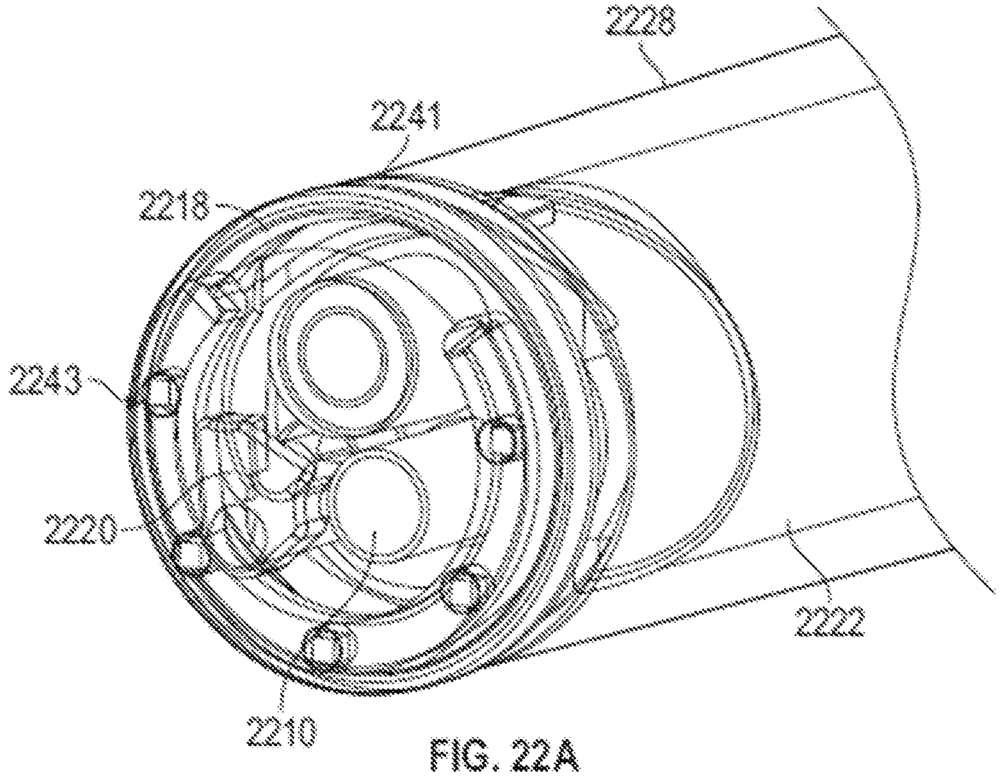
FIGS. 22A-22C illustrate an example of an endoscope sheath device having a cap including a plurality of LED light sources integrated therein. The endoscope sheath device is shown attached to an endoscope.
Figure 22B:
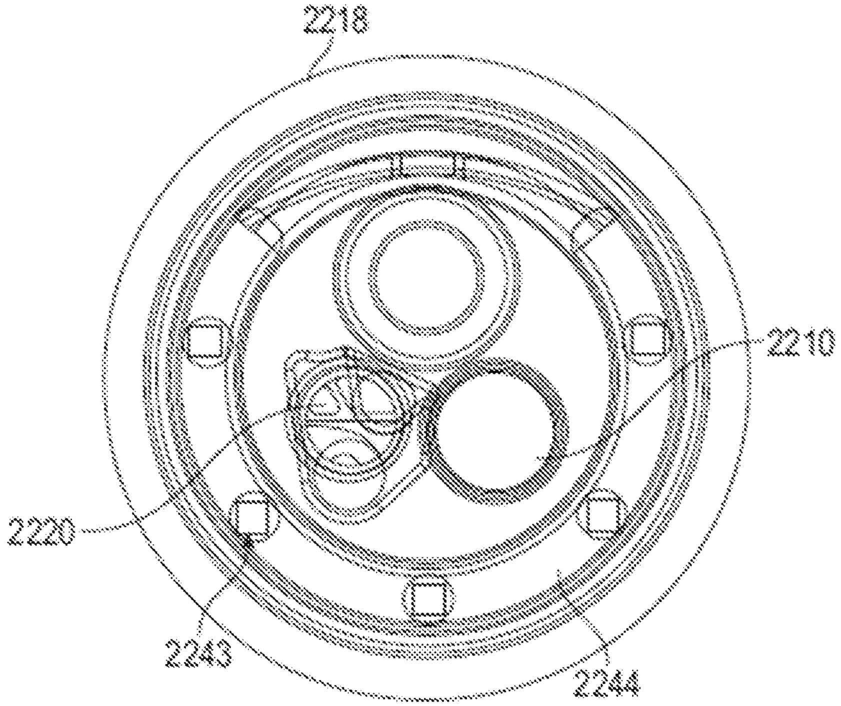
Figure 22C:
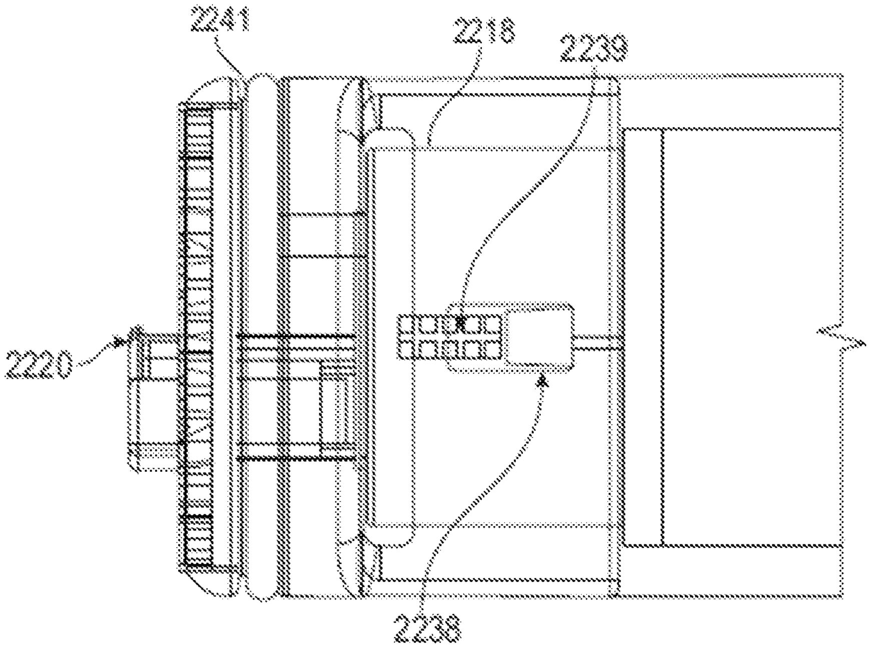

As mentioned, any of these caps and therefor any of the endoscope sheath devices described herein may include one or more light sources integrated into the cap. For example, FIGS. 22A-22C illustrate one example of an endoscope sheath device that includes a cap 2218 with an integrated set of LEDs in the lens (rather than, or in addition to, transmitting light from the endoscope). In FIG. 22A the endoscope sheath device includes an external sheath 2228 sealed to the perimeter of the cap 2218, e.g., within a channel that secures the external sheath by a gasket 2241. A pair of internal sheaths 2210 extends from the cap (e.g. through the cap and sealed around the inner surface of the openings through the cap) and into the lumen of the endoscope 2222. The cap may include other features, including a fluid displacer 2220.

The cap 2218 shown in FIGS. 22A-22C also includes a plurality of LED lights 2243 that are arranged at least partially around the perimeter of the cap. The LEDs are attached to a substrate 2244 that is held or formed within the cap. The LEDs may be powered by including one or more electrical contracts on the inside of the cap that may make contact with corresponding contacts on the end of the endoscope. For example, FIG. 22C shows a region of multiple electrical contacts 2239 on the endoscope that make electrical connection with one or more pads, pins and/or contacts on the cap once the cap is applied. In this example, the oval mating wall may include one or more of the electrical contacts needed to power the LEDs. These contacts may also be configured to be on the regions of the walls near the minor axis of the cross-section through the oval (e.g., elliptical) mating wall; this same region may include the latch 2238 (e.g., latch opening and/or latch projection).

Figure 23A:
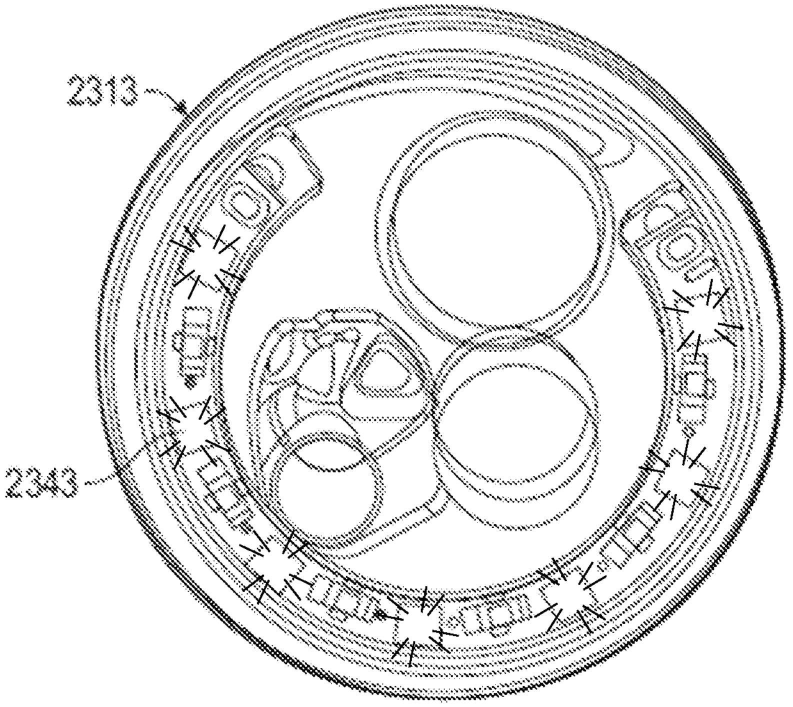
FIGS. 23A and 23B illustrate an example of a cap of an endoscope sheath device that is transparent and includes a plurality of LED lights arranged thereon.
Figure 23B:
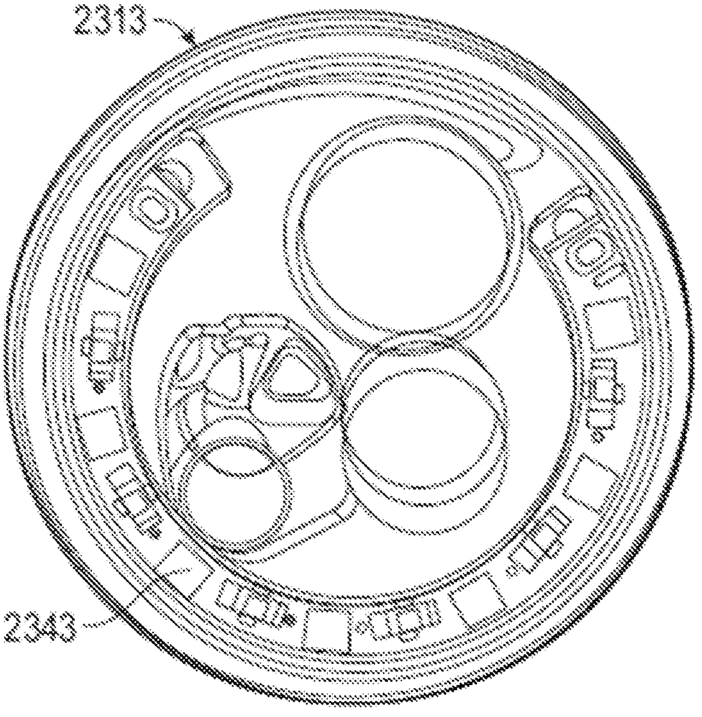

FIGS. 23A-23B illustrate another example of a cap portion of an endoscope sheath device including a plurality of LEDs 2343, similar to the arrangement of FIGS. 22A-22C. In FIGS. 23A-23B the cap is configured as a disposable cap with a transparent window. The endoscope sheath device may be placed over an endoscope in use. However if the endoscope has a camera and illumination ports, this may cause reflected light from the illumination ports to create reflection artifacts in the camera image. To avoid this problem, in some examples the cap may include illumination ports, for example, including LEDs as described above. For example, the LEDs can be placed along the outside edge of the disposable cap. Arranging illumination on the disposable cap would also free up valuable space on the face of the endoscope to support other features, or to decrease the diameter of the endoscope. One embodiment may include one to three white light LEDs. In the case of multiple LEDs, the different LEDs may be arranged at equidistant intervals around the outside perimeter of the cap (facing forward), but could be arranged in other patterns.

Some imaging arrangements may use illumination other than white light. For example, green, blue, and ultraviolet (UV) light may be used to highlight surface features of the tissue. Infrared illumination may be used with fluorescence, with or without other bands of illumination. Alternate illumination schemes may be "steady state," with the vision system switched into an alternate imaging mode and staying there until the user switches back to white light illumination. Alternatively, the vision system may change illumination patterns at frame rates, alternatively illuminating a frame with white light, then with alternative illumination, or using other temporally varying patterns. Image interpolation may be used by the systems described herein to display an alternative image overlaid with a white light image. An array of LED's, lasers, or other illumination devices on the disposable cap could enable these alternative imaging approaches. For example, a cap with three LEDs each of red, green, blue, and UV light could allow the vision system to image both in white light, and in an alternative mode to highlight details on the surface of the tissue. In the example shown in FIG. 25, these LEDs 2543 are arranged in three clusters spaced 120 degrees apart on the face of the cap 2513, with each cluster containing a red, green, blue, and UV LED closely spaced. Other configurations may be used.

In some examples wires (e.g., wire leads) may be used to power the LEDs. These wires may be routed through the endoscope, with electrical contacts between the cap and endoscope body as mentioned above. Alternatively, wire leads could be integrated into the external sheath that is attached to the cap, for example, running in a spiral around the external sheath in order to prevent limiting movement of the endoscope. Alternatively, in some examples the wires may run down or through the internal sheath (or more than one internal sheath). For example, the wires may be encapsulated thin wires.

Figure 24A:
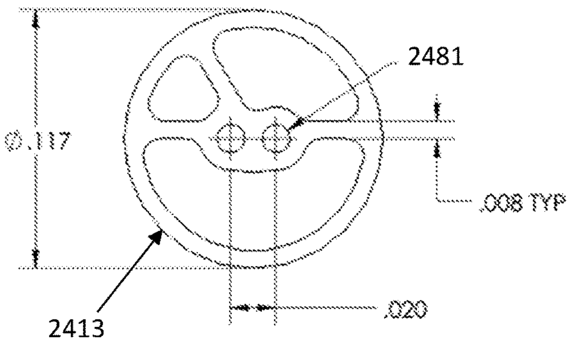
FIGS. 24A and 24B illustrate examples of caps including multi-lumen extrusions holding the wires for controlling (e.g., powering) the integrated LEDs on the cap.
Figure 24B:
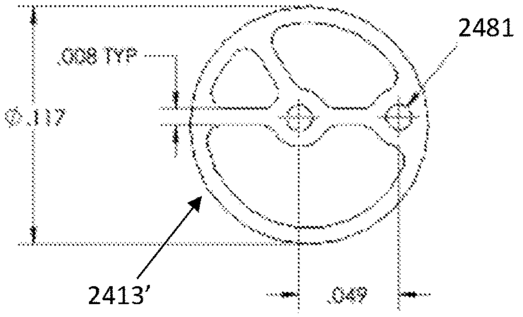
Figure 25:
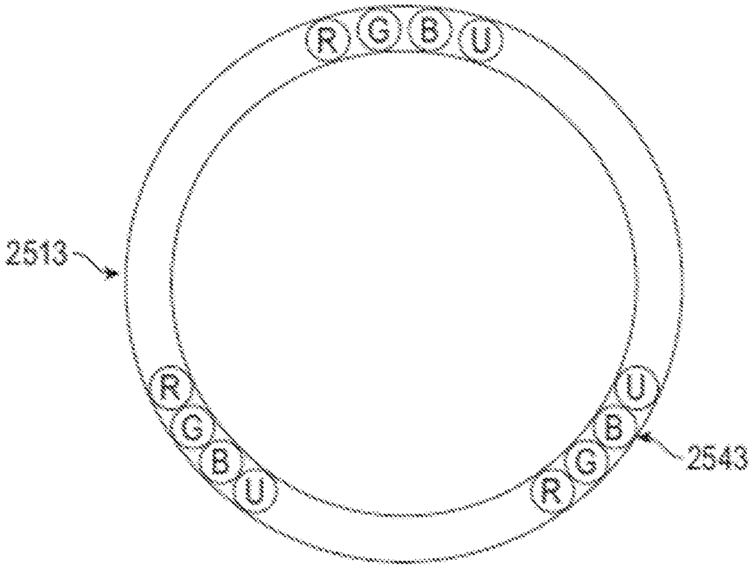
FIG. 25 schematically illustrates a cap including a plurality of LEDS of different wavelengths (e.g., colors) that may be controlled to illuminate in different colors or color combinations.

FIGS. 24A and 24B illustrate examples of multi-lumen extrusions with embedded wires (in this example, the wires are enclosed in twin 0.013" lumens). In FIG. 24A the embedded wires 2481 may be coupled to one or more LEDs (not shown) and the frame may be configured to fit over the distal end of the device as described above, including cut-our regions to allow imaging and/passage of light.

Figure 27A:
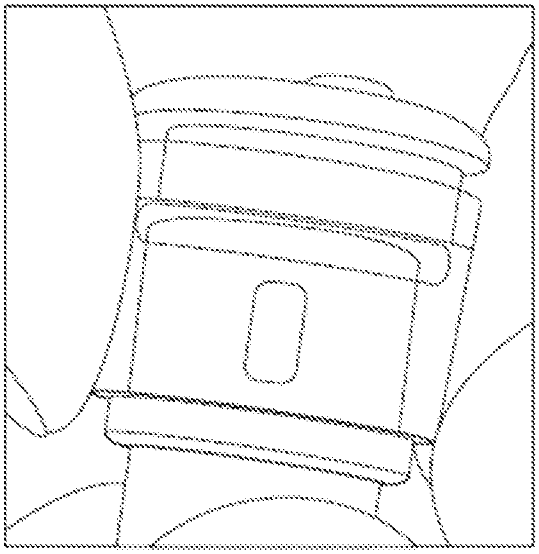
FIGS. 27A-27C illustrate one example of a method of disengaging a cap of an endoscope sheath device, which may be part of the method of removing the endoscope sheath device.
Figure 27B:
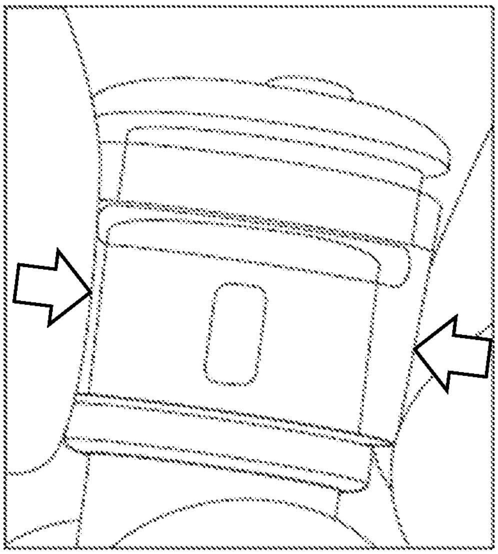
Figure 27C:
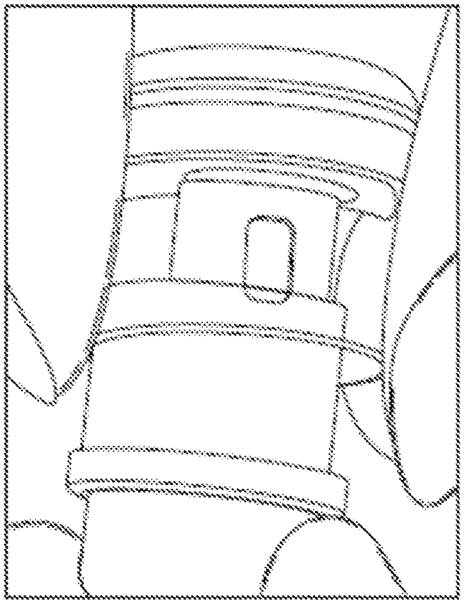

As mentioned above, in some examples the caps may be applied and/or removed from the endoscope by applying compression across the large axis of the oval, cylindrical mating wall. For example, FIGS. 27A-27C illustrate removal of a cap (the external sheath has been removed to show the application of a compression force to remove the device from the tip). As shown, the cap is disengaged by squeezing the cap to deform the mating wall to allow the latch members to uncouple (FIG. 27B) so that the cap can be pulled up and off of the endoscope, leaving the endoscope clean and ready for another use.

Figure 28A:
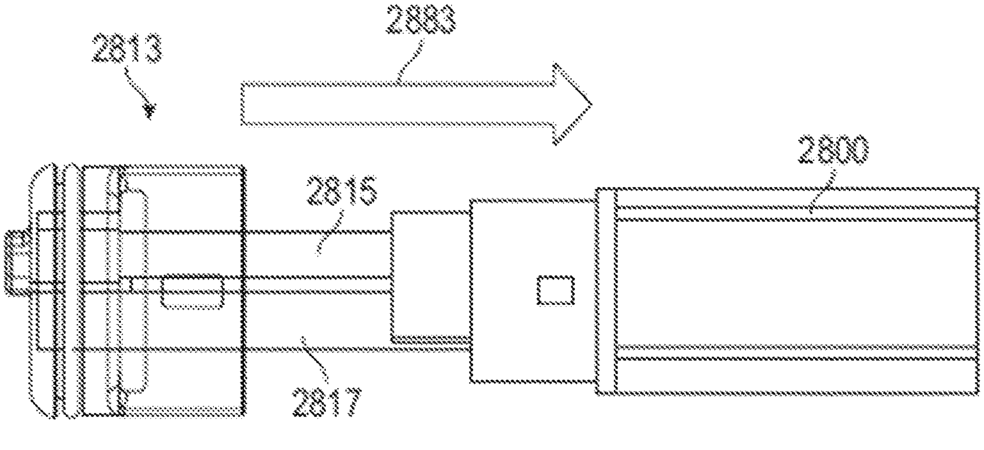
FIGS. 28A-28D schematically illustrate another example of a method for applying a cap of an endoscope sheath device which may be part of the method of applying the endoscope sheath device to an endoscope.
Figure 28B:
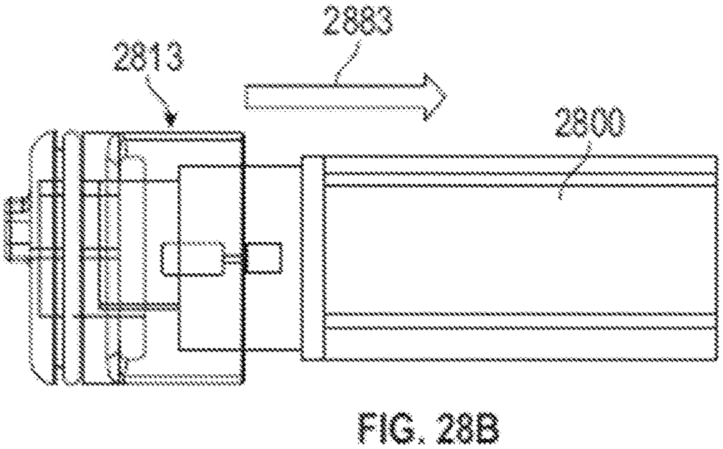
Figure 28C:
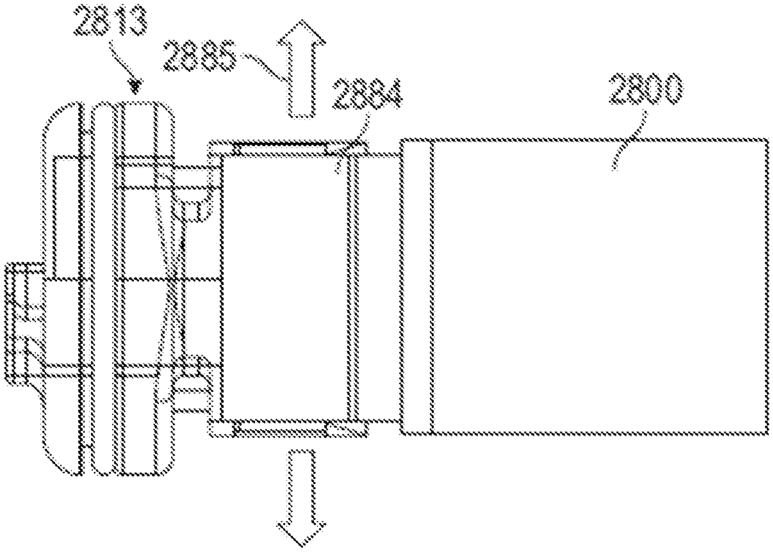
Figure 28D:
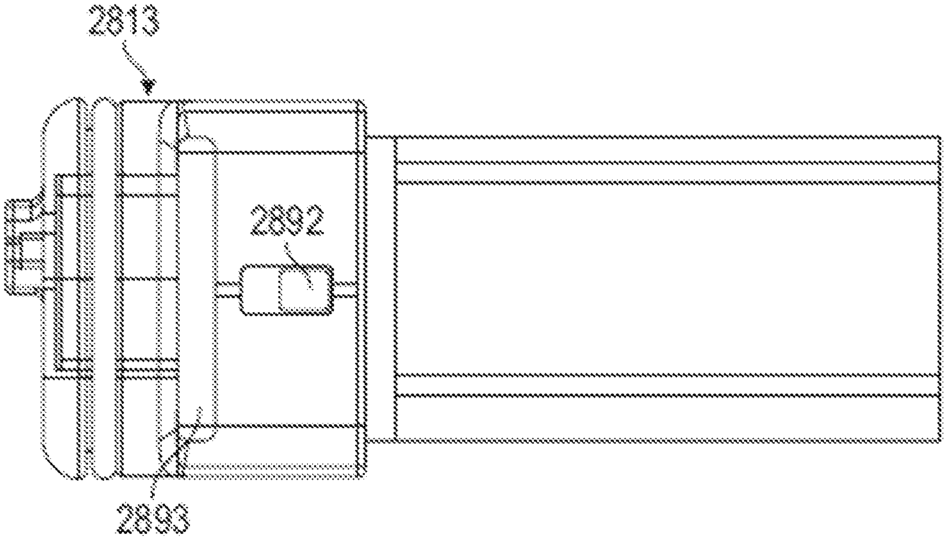
Figure 29A:
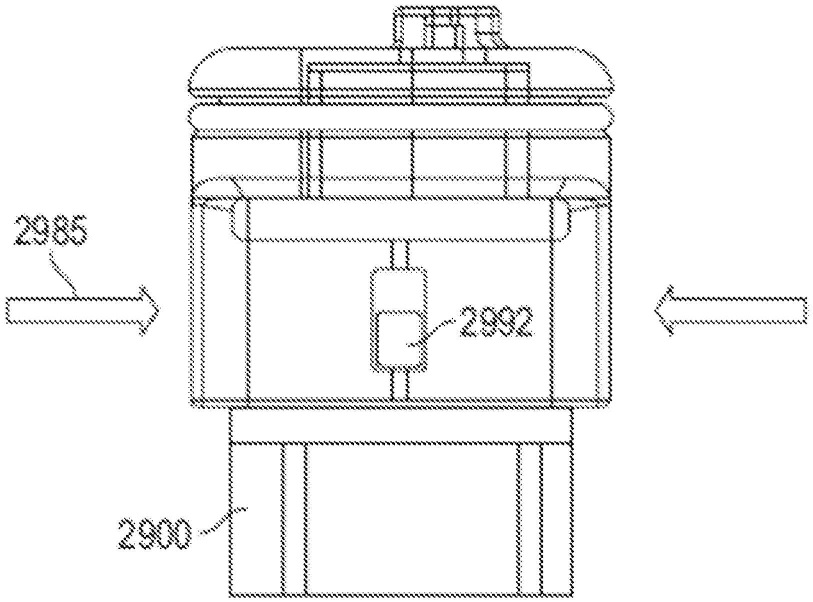
FIGS. 29A-29B schematically illustrate a method of mating a cylindrical mating surface of a cap of an endoscope sheath device with a distal end of the endoscope by compressing the sides of the cylindrical mating surface of the cap to transition the cap from an oval resting cross-sectional configuration into a circular mating cross-sectional configuration.
Figure 29B:
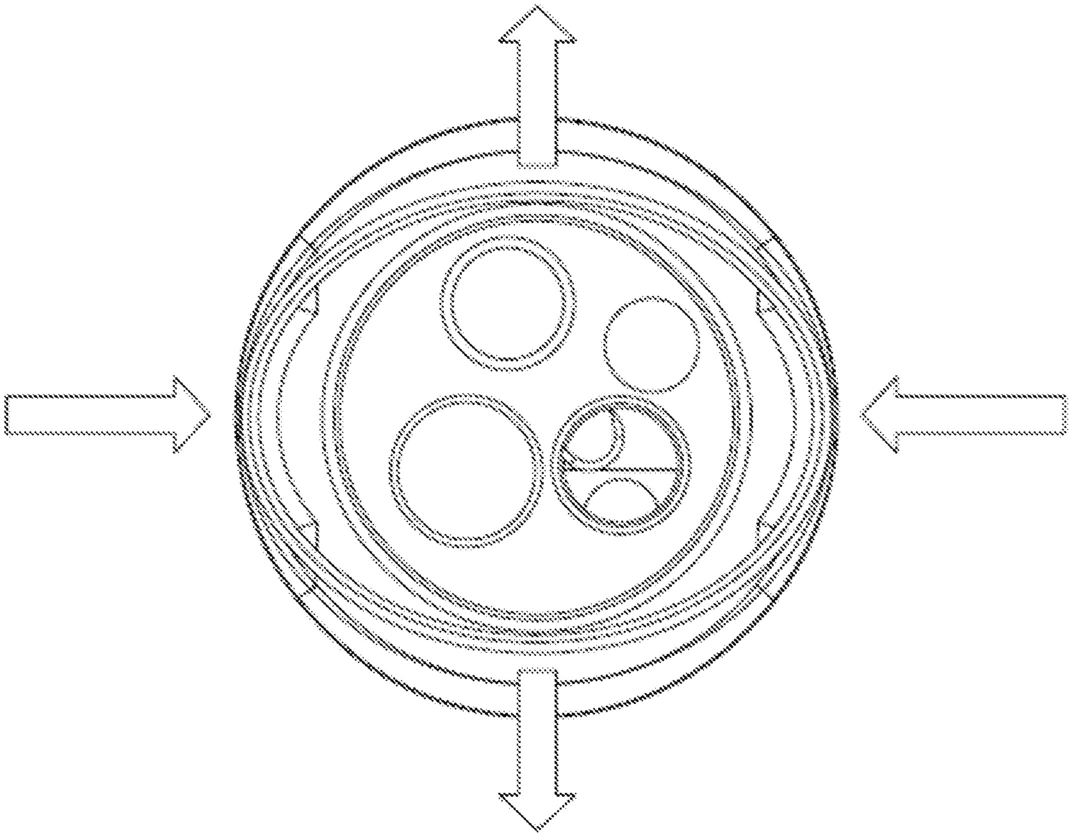
Figure 30A:
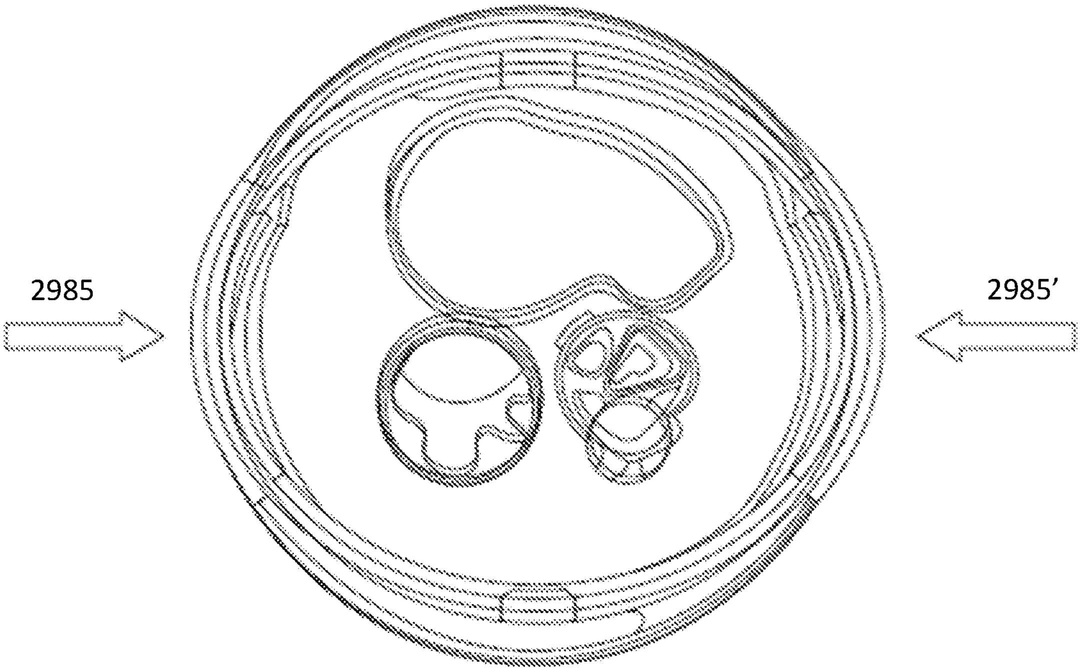
FIGS. 30A-30B show an example of a transparent cap for an endoscope sheath device similar to that shown in FIGS. 29A-29B.
Figure 30B:
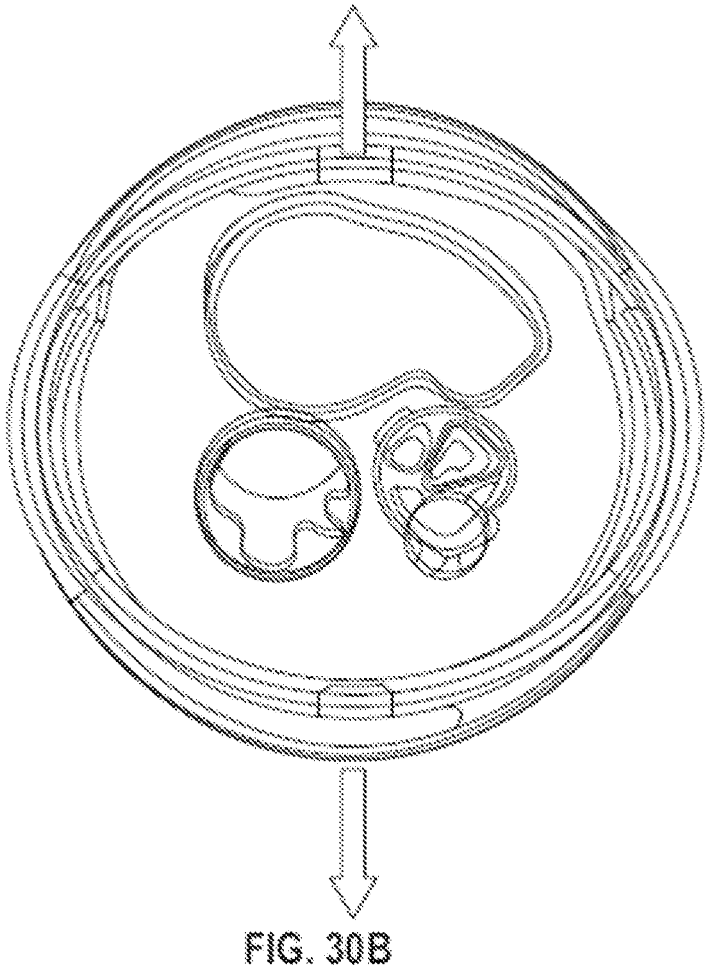
Figure 31A:
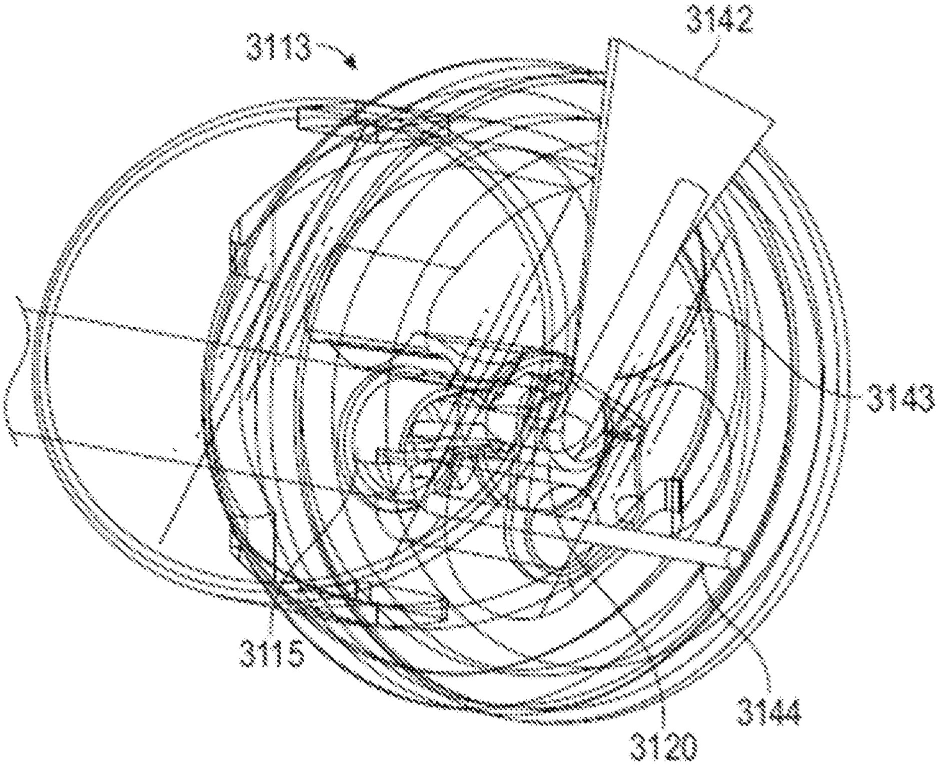
FIGS. 31A-31B illustrate operation of the multi-lumen internal sheath and cap for an endoscope sheath device.
Figure 31B:
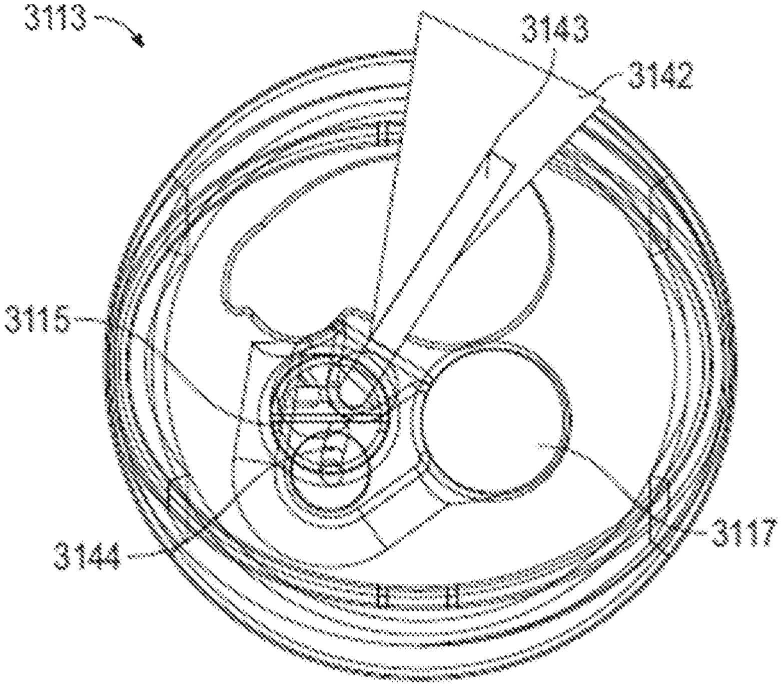
Figure 32A:
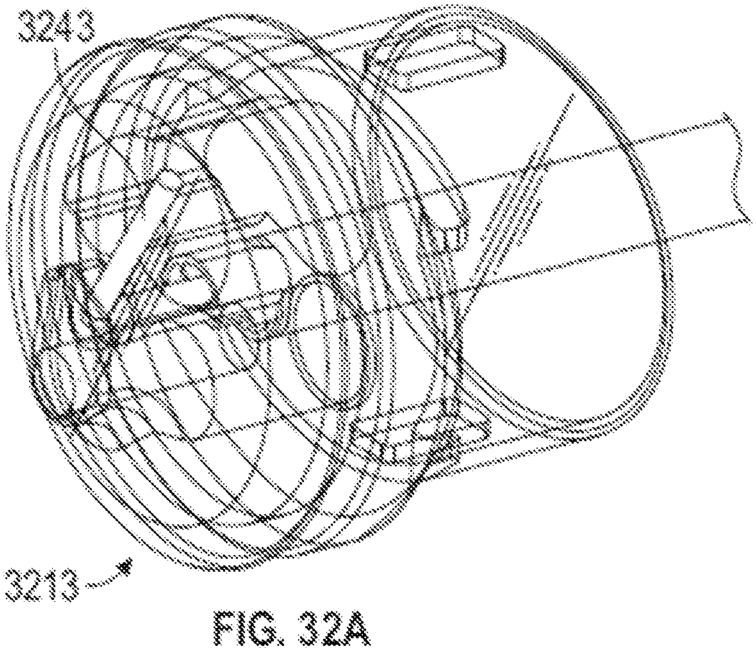
FIGS. 32A-32B illustrate the endoscope sheath device of FIGS. 31A-31B delivering a wash fluid to wash the optics of the cap in a side perspective view (FIG. 32A) and a sectional view (FIG. 32B).
Figure 32B:
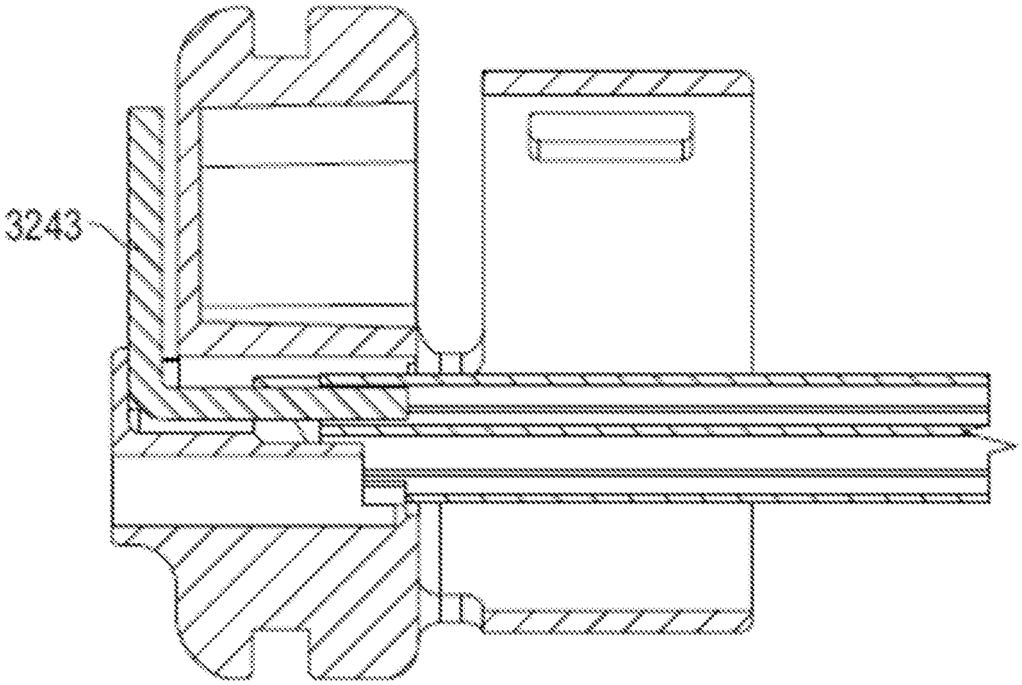
Figure 33A:
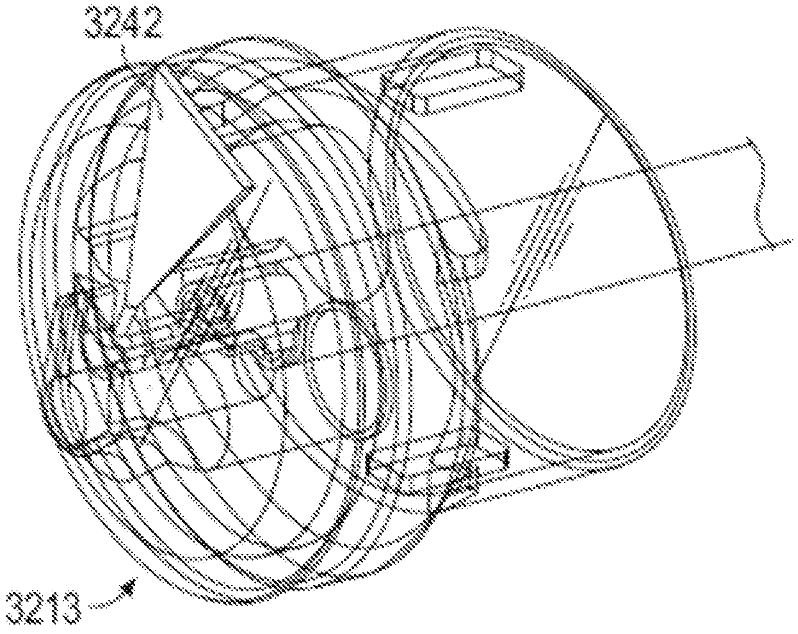
FIGS. 33A-33B illustrate the endoscope sheath device of FIGS. 31A-31B delivering insufflation from the cap in a side perspective view (FIG. 33A) and a sectional view (FIG. 33B).
Figure 33B:
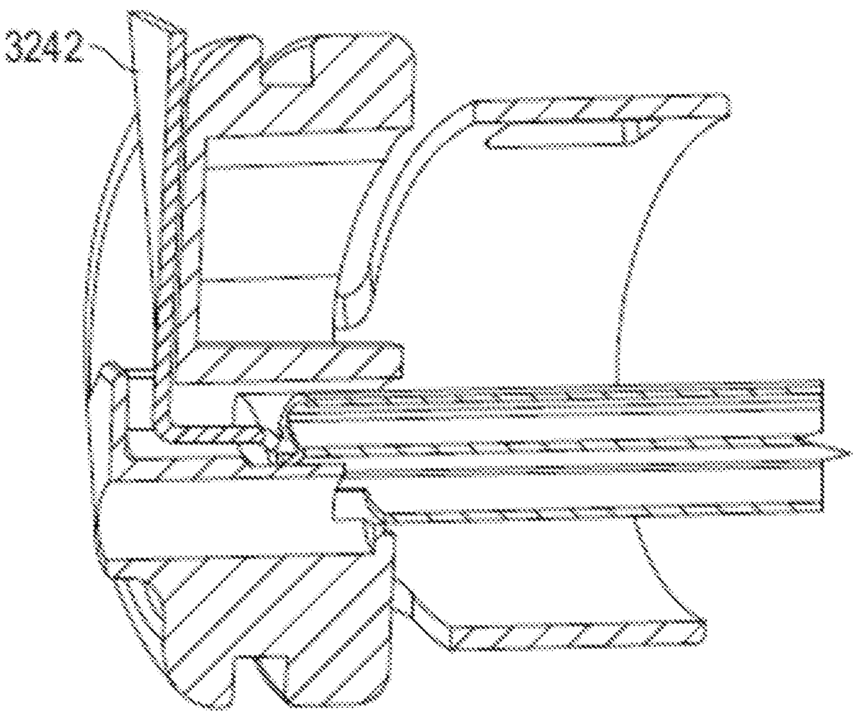
Figure 34A:
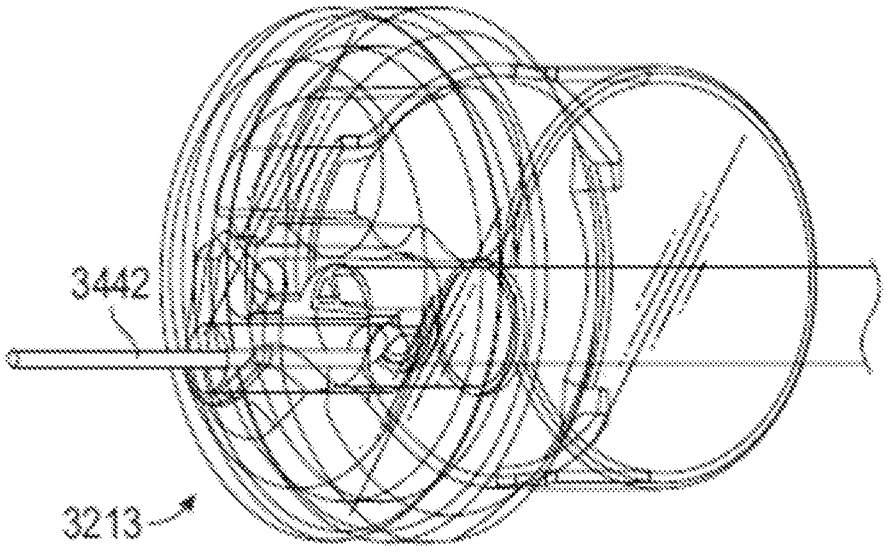
FIGS. 34A-34B illustrate the endoscope sheath device of FIGS. 31A-31B delivering an irrigation fluid from the cap in a side perspective view (FIG. 34A) and a sectional view (FIG. 34B).
Figure 34B:
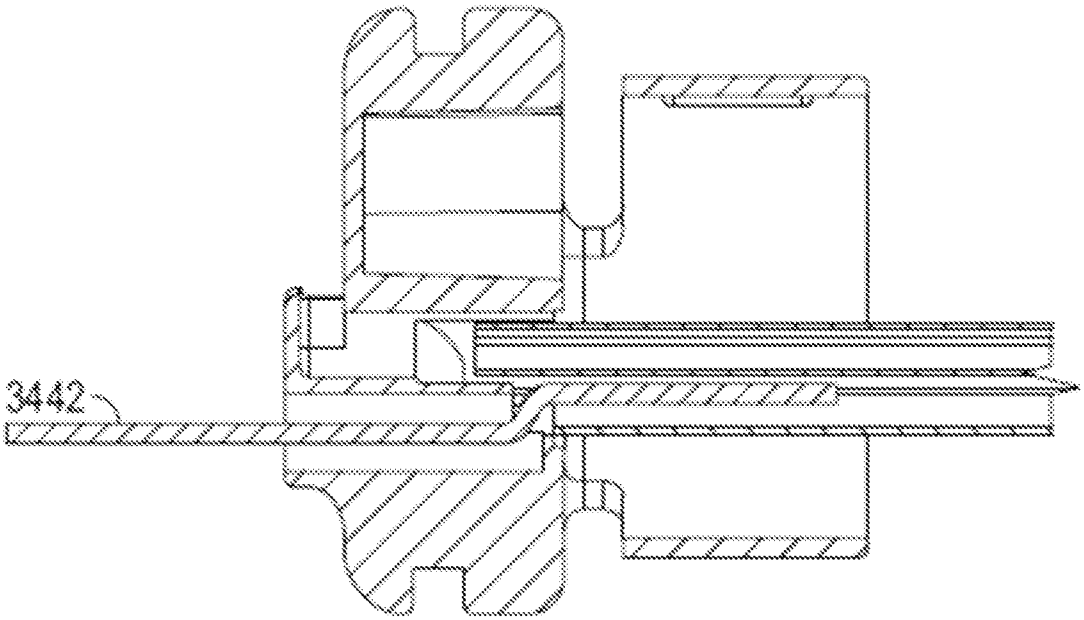

FIGS. 28A-28D and 29A-29B schematically illustrate this method. For example, in FIG. 28A the first set for attaching the endoscope sheath device to the endoscope 2800. The internal sheath(s) 2815, 2817 of the endoscope sheath device may be inserted into the lumen of the endoscope and the endoscope sheath device may be slid 2883 proximally until the cap 2813 is near the distal end region of the endoscope, as shown in FIG. 28B. Once the cap 2813 is in position, the user may use their fingers to compress the cap and deform the shape of the cylindrical mating wall 2884 so that it may fit over the distal end region of the endoscope, as shown in FIG. 28C; the pressure applied to the large axis of the cylinder may circularize this otherwise oval cross-sectional area until it can fit over the endoscope, which has a round cross-sectional area, shown in FIG. 28D. The position and extent of the stress-relief window 2893, cut through the cylindrical mating way on the opposite sides of the minor axis of the transverse section through the cylindrical wall, may make changing the cross-sectional shape of the cylindrical mating way from the oval to a more circular shape easier. The application of this compressive force 2985 may also help engaging or disengaging the latch 2992. FIGS. 30A-30B illustrate the application of compressive force 2985 to elastically deform the cylindrical wall having an oval cross-section, as described above.

Figure 35A:
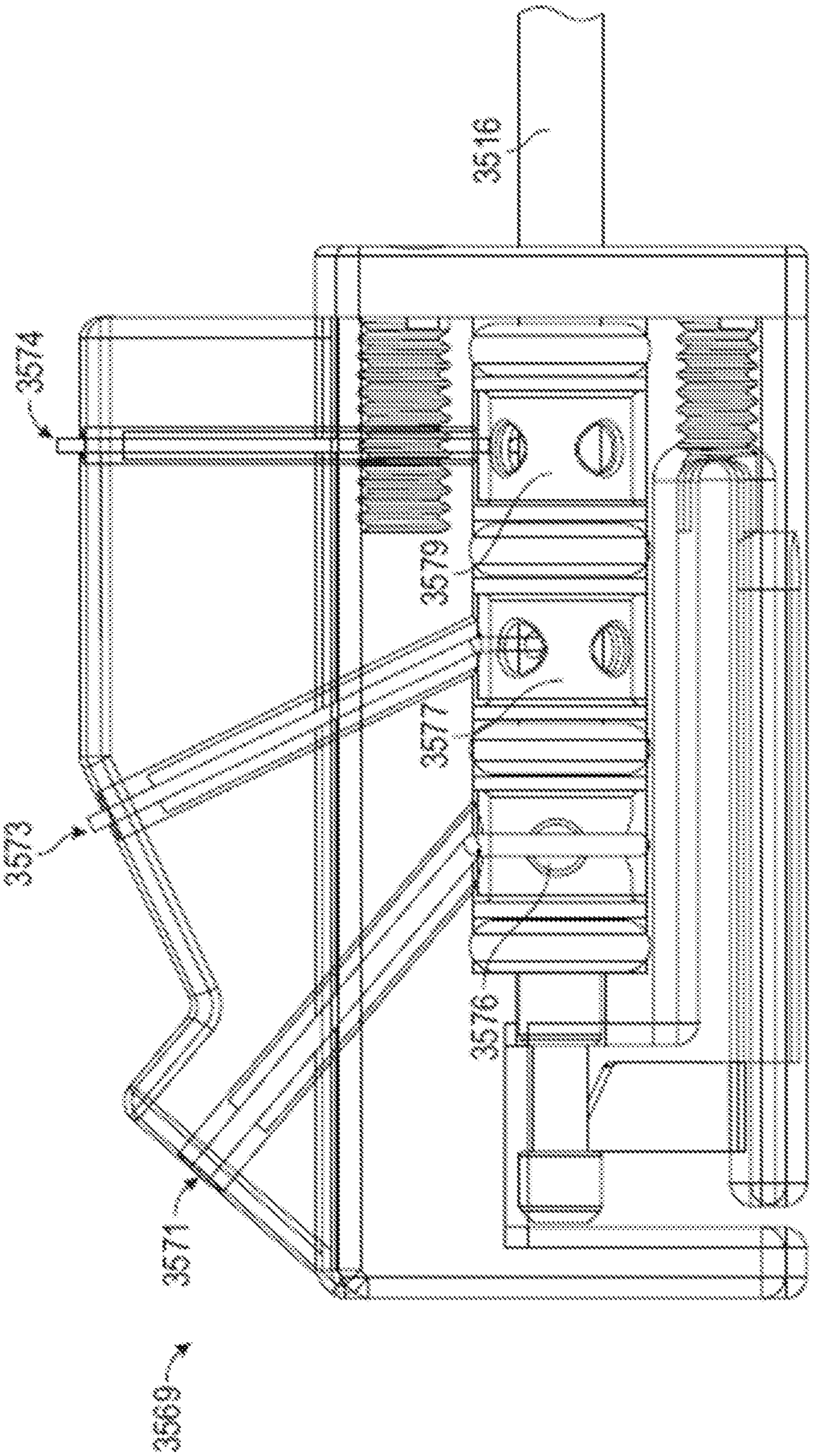
FIG. 35A illustrates one example of a port adapter that may be used with a multi-lumen catheter forming an internal sheath.
Figure 35D:
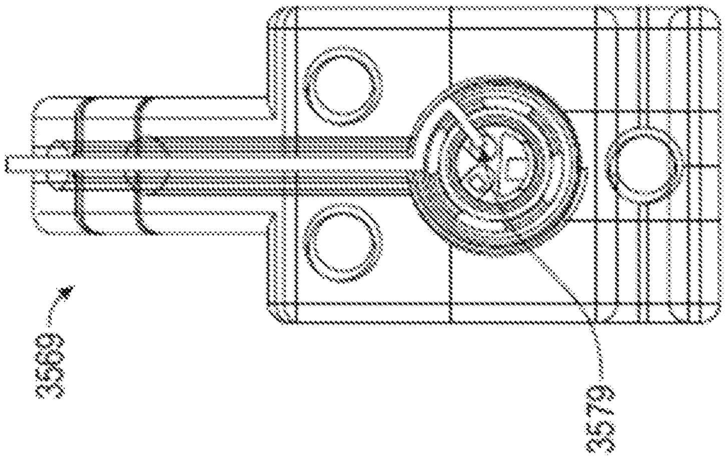
FIGS. 35B-35D show examples of end views of the (transparent) port adapter of FIG. 35A, illustrating the separation of ports for each of irrigation fluid (FIG. 35B), wash fluid (FIG. 35C) and insufflation (FIG. 35D).
Figure 35C:
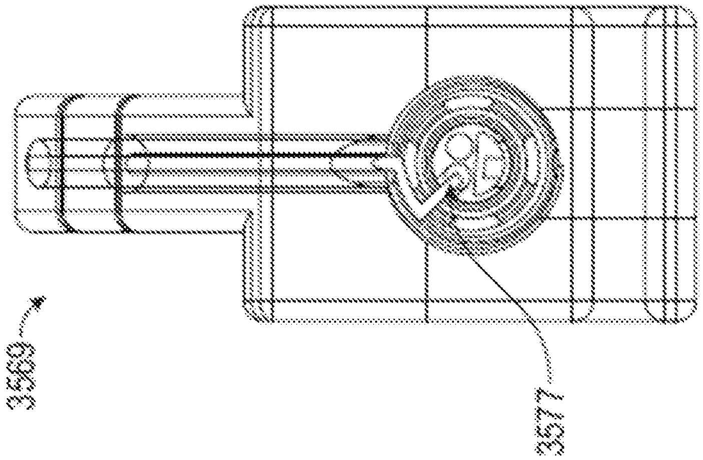
Figure 35B:
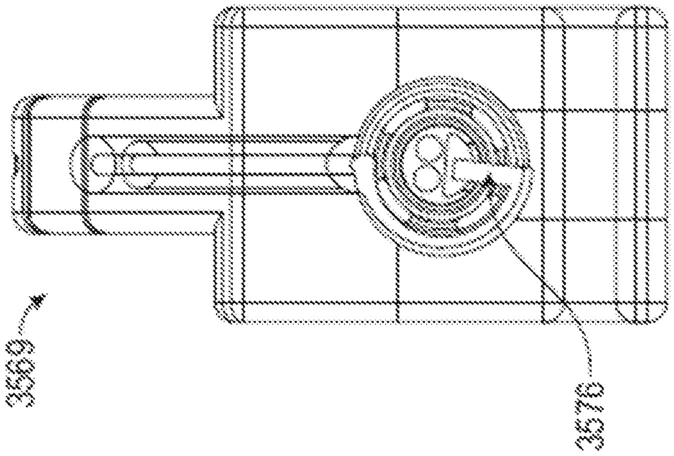

As mentioned above, any of the caps for the endoscope sheath device may include one or more features for directing the flow of material into or out of the endoscope. For example, the endoscope sheath device including a cap such as the one shown in FIGS. 31A and 31B may include integrated or attached features to direct the flow of fluid wash, fluid irrigation, and/or insufflation. In this example the endoscope sheath device includes a multi-lumen catheter 3115 forming one of two tubular internal sheaths. A second single-lumen sheath 3117 is also included. The multi-lumen sheath 3115 in this example is divided up into three sub-lumen that may be accessed at the proximal end of the device by a port adapter to apply each of: insufflation 3142, wash fluid 3143 and irrigation fluid 3144. This is illustrated in FIGS. 35A-35D, showing the operation of an example of a port adapter 3569. In this example the multi-lumen internal sheath 3516 is inserted fully into the port adapter until a latch engages with the distal end of the port adapter, indicating that the lateral openings into the different lumen arranged at different longitudinal positions along the length of the internal sheath are aligned with the appropriate sealing regions of the receptacle manifold of the port adapter. For example, in FIG. 35A the irrigation port 3576 into the first lumen is accessed from the position so that irrigation fluid may be applied through the port adapter input for irrigation fluid 3571. The wash fluid port 3577 into the second lumen is accessed from the middle position so that wash fluid may be applied through the port adapter input for wash fluid 3573. The insufflation port 3579 into the third lumen is accessed from the more proximal position so that insufflation may be applied through the port adapter input for insufflation 3574. FIGS. 35B-35C show end views of these different ports.

Returning now to FIGS. 31A-31B, the insufflation 3142 may be directed out of the multi-lumen catheter forming the internal sheath 3115 by the deflector 3120 so that the insufflation 3142, 3242 is directed across the camera region. This is shown in greater detail in FIGS. 33A-33B. The flattened triangular component is representative of the general location of the insufflation. Similarly, the wash fluid 3143, 3243 is directed out of the multi-channel lumen of the internal sheath by a deflector 3120 on the cap 3113 that may direct the wash fluid across the outer surface of cap 3213 to clear debris that may otherwise occlude the camera. This is shown in greater detail in FIGS. 32A-32B. The bent cylindrical shape shown to represent the wash fluid 3243 is representative of the general direction of flow of the wash fluid. Irrigation fluid 3144, 3442 may be directed from out of the multi-lumen catheter forming the internal sheath as shown by the representation of irrigation in both FIGS. 31A-31B and 34A-34B.

As discussed above, the cap may also include one or more optical components integrated into (including formed integrally in) the cap. For example, any of these endoscopic sheath devices may include a cap having an integrated lens or lenses for the camera of the endoscope, as shown in FIGS. 36A-36B. In this example a domed lens 3652 is formed as part of the cap 3600, which may include other components such as a fluid displacer 3620. When the cap is attached to the distal end region of an endoscope as shown in FIG. 36B by cross-section, the camera of the endoscope 3688 is in direct communication with the lens 3652 formed on the cap. The endoscope sheath device 3600 of FIGS. 36A-36B also includes a second internal tubular sheath 3617 that is configured as an internal working channel and is lined by the second internal tubular sheath 3617.

Figure 37A:
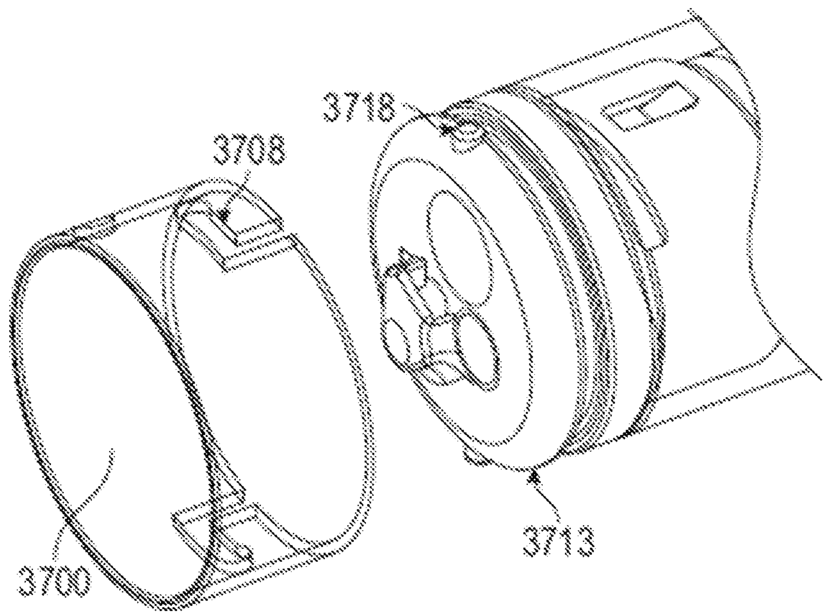
FIGS. 37A-37C illustrate removable components (e.g., scope caps) that may be used with any of the endoscope sheath devices described herein.
Figure 37B:
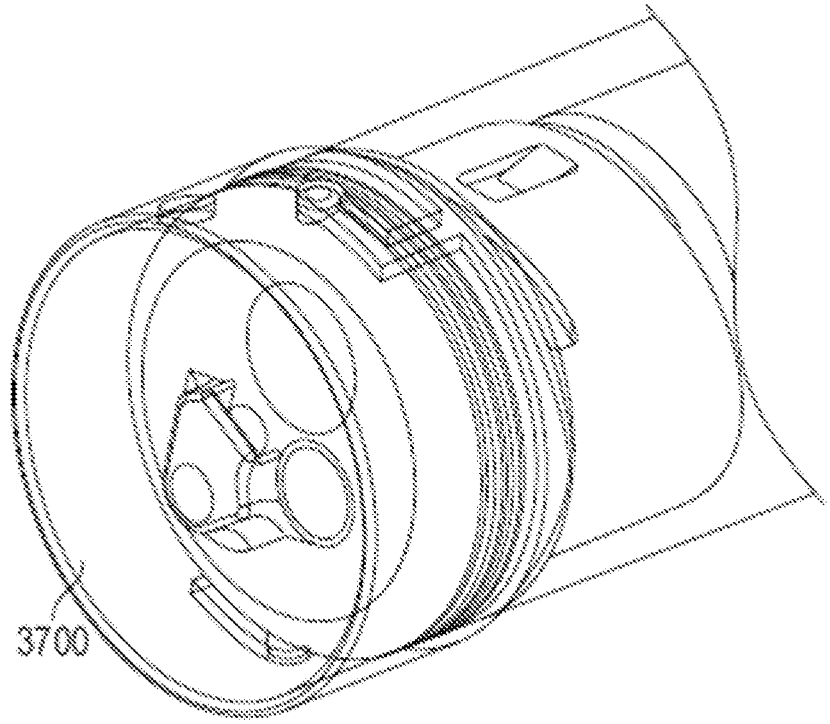
Figure 37C:
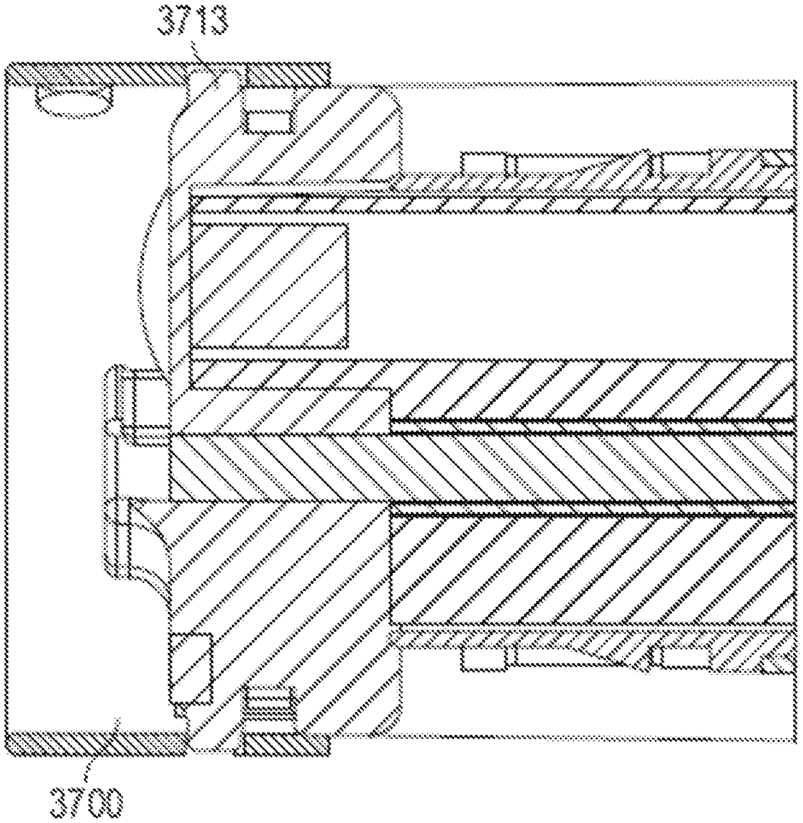

Any of the apparatuses described herein may include one or more accessory elements that are configured to be used with the endoscope sheath device, such as scope caps and the like. These accessories may be added or coupled to the endoscope sheath device after or before it has been applied to an endoscope, or they may be integrated into the endoscope sheath device, e.g., as part of the cap. For example, FIGS. 37A-37C illustrate an example of a removable scope cap 3700 that include a retention feature 3708 (in this example, configured as a bayonet type attachment). In FIG. 37A the removable scope cap 3700 is separate from the endoscope sheath device (e.g., the cap 3713 of the endoscope sheath device) and in FIG. 37B the removable scope cap 3700 is coupled to the cap of the endoscope sheath device. FIG. 37C show a side sectional view of FIG. 37B.

Figure 38:
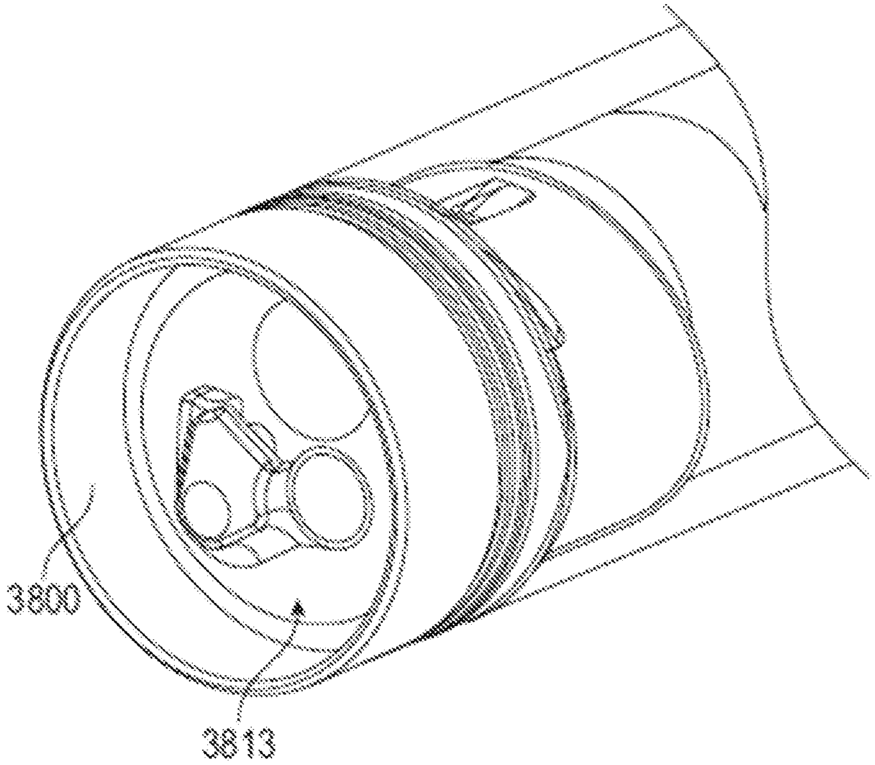
FIG. 38 shows an example of an endoscope sheath device with an integrated (e.g., molded or overmolded) end cap.

In general, the methods described herein may include attaching, removing and/or swapping out of different scope caps depending as necessary to the user. In some examples the endoscope sheath device may be configured to integrate one or more of these features, such as a scope cap extending from the distal end. FIG. 38 illustrates an example of a cap 3813 in which the scope cap portion 3800 is integrally formed with the rest of the cap.

Figure 39A:
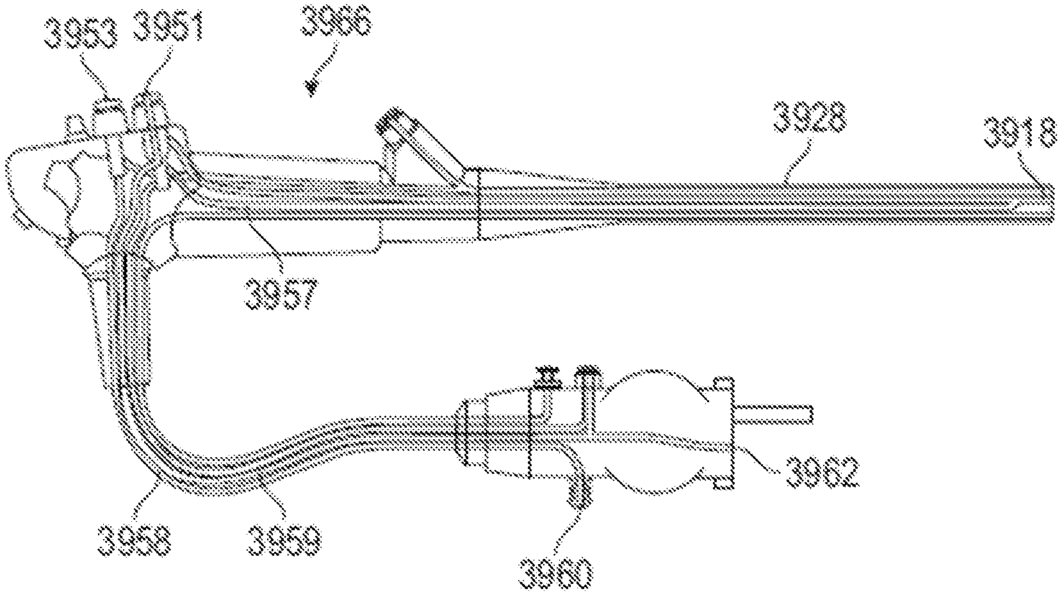
FIG. 39A illustrates an example of a prior art endoscope.

Also described herein are endoscopes that may be modified to more easily operate with the endoscope sheath devices described herein. For example, FIG. 39A illustrates an example of a prior art endoscope including an elongate body 3928 having a distal end region 3918 and a plurality of internal lumen 3957. In this example the lumen are coupled to suction 3958 and air/water 3959. The device may also include valves, such as suction valves 3953 and air/water valves 3951 that may regulate the flow of suction, air and/or water within the lumen. The handle region 3966 may be coupled to the elongate body 3928 and to a cord that may connect to the source of suction and/or air, e.g., via a suction connector 3960 or air pipe 3962.

Any of the apparatuses described herein may include an endoscope that is adapted for use with an endoscope sheath device; these systems may include endoscope devices in which the valves controlling the flow of material (e.g., vacuum, water, air, etc.) in the lumen of the endoscope may be separate from the separate and/or may be disposable. For example, a catheter adapted for use with an endoscope sheath device may include a handle region that is configured to pass the internal sheath(s). In some examples the endoscope has an elongate member with a lumen extending from a handle. The system may also include an endoscope sheath device that includes the external sheath, an internal sheath comprising one or more lumens and a cap as described above. The system may also include a manifold block that is removably coupled to the handle of the endoscope, wherein the manifold block comprises one or more valves in fluid communication with the lumen of the endoscope. The internal sheath may be configured to engage with the manifold block so that the one or more valves control passage of fluid through the one or more lumens of the internal sheath.

Figure 39B:
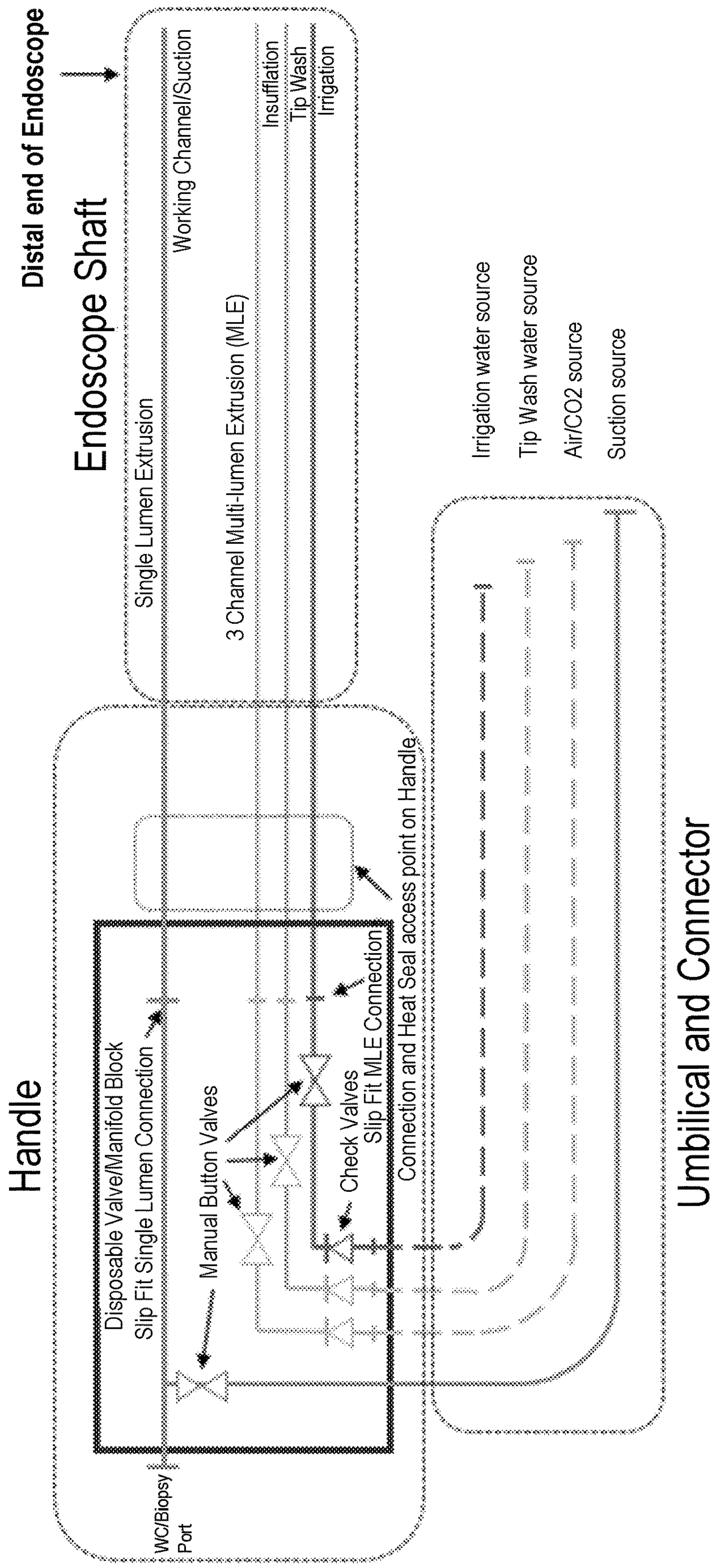
FIG. 39B schematically illustrates an example of a manual endoscope adapted for use with an endoscope sheath as described herein.

For example, FIG. 39B schematically illustrates an endoscope as described herein. In this example the endoscope includes an elongate shaft (endoscope shaft) having two internal lumen. The first lumen is for accepting a working channel and/or suction channel. The second lumen is for accepting a multi-lumen channel that may couple to insufflation, wash fluid and irrigation fluid. In FIG. 39B the elongate shaft is coupled to a handle region. The handle region may also include a disposable manifold block that may include a plurality of valves and/or controls for engaging with the internal lumen and/or for controlling the flow within the lumen. For example, the disposable manifold block may include manual button valves and/or check valves that prevent flow in the reverse direction, but permit flow of fluid from the handle to the distal end of the shaft. The apparatus may also include a sealing/crimping region (e.g., a heat sealing access point) to allow the internal shafts to be sealed when use is complete. Finally, the apparatus may also include a line ("umbilical" line) and connectors for coupling to the sources of irrigation (water), wash, insufflation (air/CO2) and/or suction.

In general, the device shown in FIG. 39B is configured for use with an endoscope sheath device so that the external sheath may cover the outside of the distal end and shaft (and in some examples, the handle, and optionally the umbilical) and the internal sheaths may extend within the lumen and through the manifold block to couple with the connectors. Thus the manifold block may be adapted to receive the internal sheaths and the valves and controls may operate on the internal sheaths.

Any of the apparatuses and methods described herein may be configured to apply positive or negative pressure between the external sheath of the endoscope sheath device and the outer surface of the endoscope. Thus, any of these apparatus may be configured to apply negative pressure (e.g., vacuum) to adhere the external sheath to the outside of the endoscope, which may make it easier to hold and use (e.g., apply torque). The use of pressure, including negative pressure, may also alert the user to any leaks or ruptures in the sheath. Alternatively, any of these methods and apparatuses may use positive pressure to inflate the external sheath, which may help with navigation, deployment and/or leakage detection.

In any of these apparatuses and methods the endoscope sheath device may be configured to allow pressurization of the external sheath by forming a seal at the proximal end region of the external sheath, e.g., on the endoscope sheath and/or handle. The distal end region, including the cap, may also form a seal, or in some examples may not seal, but may be sealed around the more proximal ends of the internal sheath(s).

Figure 40A:
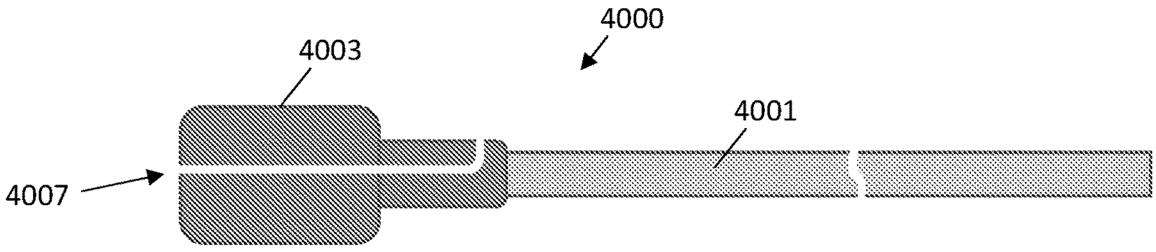
FIGS. 40A-40C illustrate examples of an endoscope sheath device in which the external sheath may be inflated and/or collapsed (e.g., deflated).
Figure 40B:
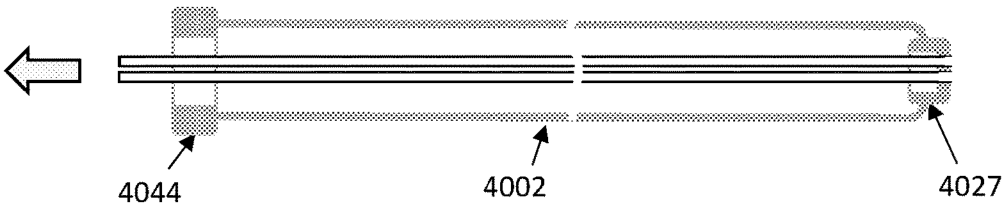
Figure 40C:
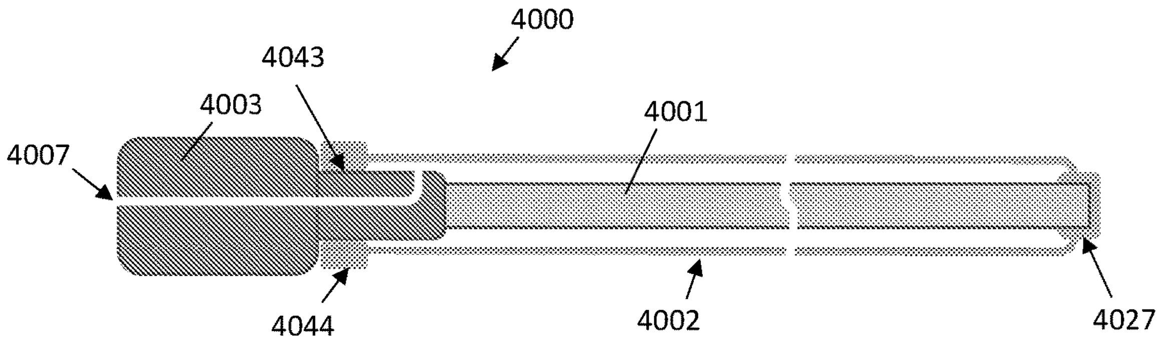

FIGS. 40A-40C illustrate a first example of a system including an endoscope sheath device that is configured to pressurize the external sheath of the endoscope sheath device. FIG. 40A schematically illustrates an example of an endoscope 4000 that include an elongate shaft 4001 and a handle region 4003. In this example the endoscope handle may include a pressure line 4007 (e.g., for positive or negative pressure) that may be used to apply pressure between the endoscope and the external sheath. In some examples the pressure line is coupled to the endoscope sheath device, e.g. at the sheath proximal collar. The pressure line may be integrated into either the endoscope or the endoscope sheath device or it may be a separate and individually positioned line.

FIG. 40B schematically illustrates an endoscope sheath device that includes a pressurized external sheath 4002, and a pair of internal sheaths, as well as a cap 4027 sealed to the external sheath and internal sheath. The endoscope sheath device also includes a proximal collar 4044 that is configured to maintain a seal between the endoscope and the proximal end of the external sheath.

FIG. 40C shows the endoscope of FIG. 40A with the endoscope sheath device of FIG. 40B applied, creating a sealed zone or region between the external sheath and the endoscope that may be pressurized, e.g., by applying vacuum to collapse the sheath onto the endoscope or applying positive pressure, e.g. to expand or inflate the external sheath. The collar 4044 may be activated to form an airtight seal 4043 (e.g., proximal sealing collar). In FIG. 40B the external sheath of the endoscope sheath device has a substantially uniform diameter along the proximal-to-distal length. In some cases it may be beneficial to have regions of different radial diameter along the length and/or regions of different elasticity so that the different regions may be inflated differently.

The proximal sealing collar 4043 may be configured to seal the outer sheath to the outside of the endoscope. Any of these apparatuses may also or alternatively include a seal (e.g., an O-ring or other annular seal) between the inner sheath and the inner lumen of the endoscope. Thus, in any of these examples pressure may be applied between either or both the outer sheath and the endoscope and/or the inner sheath and the lumen of the endoscope (or multiple inner sheaths and lumens of the endoscope). In some cases the cap may include one or more openings or channels to allow passage of pressurized fluid (e.g., air, saline, water, etc.) from between the outer sheath and the outer surface of the endoscope and between the inner sheath(s) and the lumen(s) of the endoscope. Thus the patency of the entire sheath (both outer sheath and one or more inner sheaths) may be concurrently examined. Alternatively, these apparatuses and methods may determine a leak in outer sheath alone.

Any of these apparatuses may include an indicator configured to indicate, based on a decay of pressure from between the external sheath and the endoscope, if the sheath device has a leak indicating potential contamination. The indicator may be analog, digital or both. The indicator may include indicator circuitry having logic to determine if a pressure leak above a threshold (pressure leak threshold) corresponds to a tear, rip or disruption of the outer and/or inner sheath(s) and therefore a likelihood of contamination. The indicator may be coupled to the sheath and/or to the endoscope. In some examples the indicator is coupled to an inlet for pressurizing the space between the outer and/or inner sheaths and the endoscope. The inlet may be part of the sheath device (e.g., part of the proximal collar) and/or part of the endoscope and/or part of a pressure source coupled to either the endoscope and/or the sheath device. The indicator may include a speaker, display, etc.

Figure 41A:
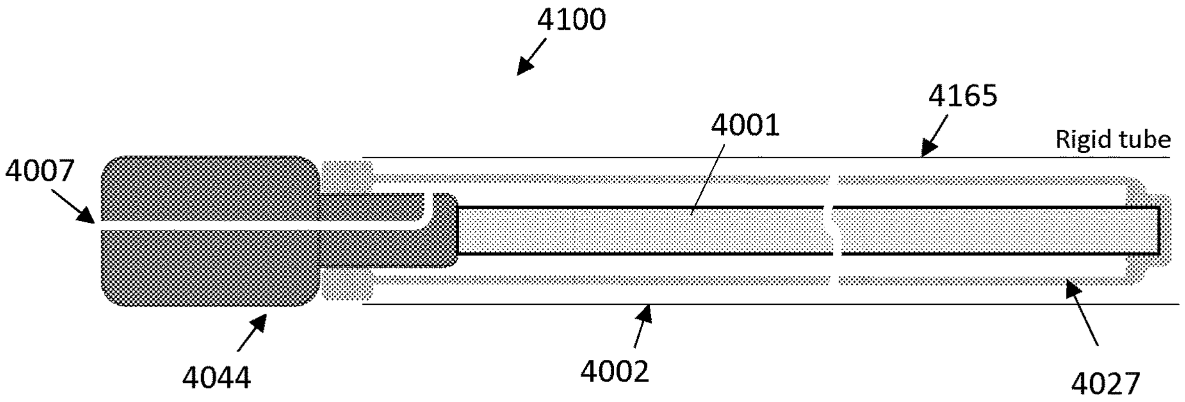
FIG. 41A schematically illustrates an example of an endoscope sheath device coupled (and sealed to) the endoscope. The tubular external sheath of the endoscope sheath device has a uniform profile along the length of the sheath, and is shown with a tube that can be used to assist in installation of the endoscope, allowing the external sheath to be vacuum expanded (outward) during installation.
Figure 41B:
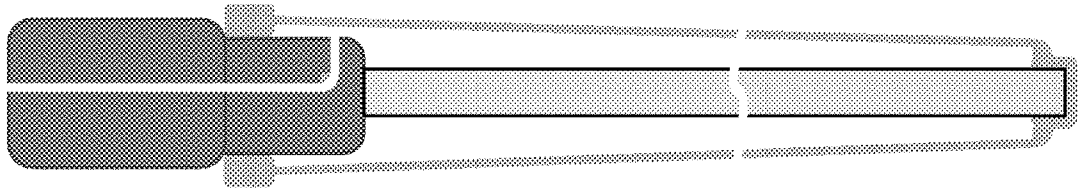
FIG. 41B schematically illustrates an example of an endoscope sheath device (having a tapered profile) coupled (and sealed to) the endoscope.
Figure 41C:
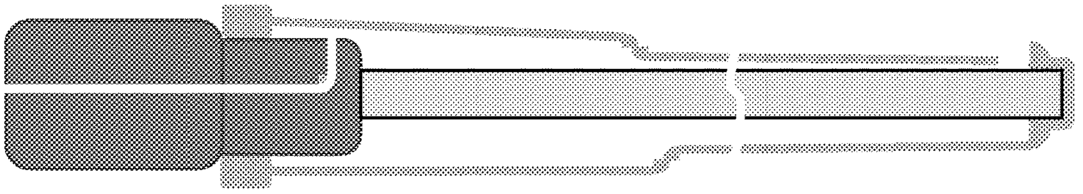
FIG. 41C schematically illustrates an example of an endoscope sheath device coupled (and sealed to) the endoscope. The tubular external sheath of the endoscope sheath device has a stepped-down profile along the length of the sheath.

For example, FIGS. 41A-41C illustrate examples of endoscope sheath devices having different configurations of the external sheath. These different configurations may be particularly helpful during inflation. The flexible external sheath portion of the endoscope sheath device may have a constant cross-section as shown in FIG. 40B. Alternatively, the cross-section may be nominally larger than the shaft, such that it can slide on easily with a small annular gap. Any of these external sheaths may be relatively elastic, such that they may be vacuumed out to expand it (for example, by sealing at either end into a rigid tube, with the annular space between them a space that is then vacuumed). Once in place, e.g., with the sheath fully positioned over shaft, the vacuum could be released so that the sheath elastically recoils and then lies snugly against the shaft. This is illustrated in FIG. 41A, showing the external sheath having a constant diameter but held within an outer, e.g., rigid, tube. The external sheath is then vacuumed out into this space to expand it during install. In FIG. 41A the external sheath 4027 has a constant width. Once in place, vacuum may be released, and the external sheath may elastically return to the released size to snugly conform to shaft.

In some examples the external sheath may be substantially larger (e.g., greater than 1.5× diameter, 2× diameter, 2.5× diameter, 3× diameter, 3.5× diameter, 4× diameter, 5× diameter, etc.) than the shaft. This configuration may be advantageous once inflated by positive pressure, as it may help position, stabilize, anchor, and/or guide the device within the anatomy, particularly tortious anatomy.

In some examples (see, e.g., FIG. 41B) the external sheath may have a tapered or a stepped cross section (see, e.g., FIG. 41C), larger at the proximal end. This sort of profile could assist with removal—it is everted back on itself during removal, thereby 'capturing' biological debris on the outside, making its disposal cleaner and easier. This may also facilitate installation and hygienic removal of the replaceable sheath. In some examples the endoscope sheath device may be configured to seal at either end, such that it could then be vacuumed down against the elongate shaft.

In any of these methods and apparatuses the sheath may be installed over the device, either as a manual device (scope or catheter) or as a robotic device (a tele-operated device).

During use, the external sheath may be snug, or it may be loose relative to the endoscope shaft. The external sheath may be a sealed structure once it is co-joined with other structures—including the shaft or install tools. At the proximal end, it may have a port that allows access to that (annular) space. Through that space positive or negative pressure may be applied. As negative pressure is applied, the sheath would be suctioned down to the underlying structure, such that it is vacuum co-joined with that structure. If the device is manually operated, that enables the hand to better grip that surface, and for the sheath and the underlying shaft to move as one. Should the sheath not be vacuumed, such movement would be difficult, as the sheath would be moving and shearing relative to the elongate shaft during attempts at movement.

During installation, the sheath may be co-joined with an installation tool. Once it is co-joined, the annular space between them (the installation tool and the sheath) could be vacuumed, thereby causing the sheath to elastically expand. This would give it a larger inner diameter, such that it could more easily expand over the shaft. Once it has been loaded over the shaft, vacuum would be released and it would elastically reduce its diameter, such that it would be snug to the shaft.

In any of these methods and apparatuses, the sheath can be inflated with positive pressure. When inflated, the sheath can contact the anatomy. For example, it can contact the inside of the lungs, the inside of the GI tract, etc. This may similarly function in other anatomies, including but not limited to gynecology, abdominal, orthopedic, vascular, neurovascular, and peripheral vascular. This application of positive pressure and its interaction with anatomy creates co-joined stability. This contact could present locally (i.e., as a single balloon), in multiple locations (serial balloons), or over a long length (constant diameter interaction, tapered geometry interaction, etc.).

Figure 44:
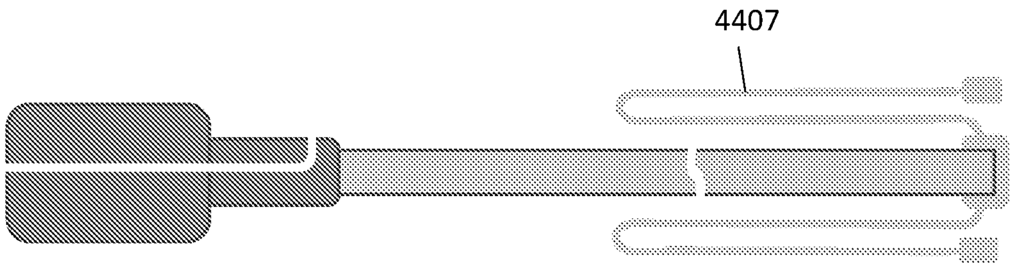
FIG. 44 is a schematic illustration of an example of an endoscope sheath device configured to evert over itself for removal from the endoscope after use.

The endoscope sheath device may be packaged in multiple configurations, including straight and coiled. These packaging configurations may be created to decrease installation difficulty and time, and to reduce packaging, shipping, and sterilization costs. The endoscope sheath device may be configured to easy removal. For example, after use, the outside surface of the device may be contaminated with feces, blood, and other bodily fluids. It may be difficult or cumbersome to handle. The device may be configured such that it everts (i.e., rolls back on itself). By doing so, it thereby reduces the effective sheath length (everting doubles the wall, and thereby reduces the length by half). Everting also serves to have the exterior (contaminated) surface facing inwards, with the clean surface facing outward, such that it can be removably handled in a more sanitary manner. For example, FIG. 44 illustrates an everting sheath 4407 that is configured for easy removal.

In some examples it may be important to have the sheath electronically register with the base device. This registration may transmit information, including about the device type, its operation, its manufacture, its authentication, its sterility, or the legality of its integrative use. A reader and/or transmitter (e.g., RFID) may be installed, for example, on the base. As the sheath proximal collar is in proximity, it may register or transmit information.

Figure 42:
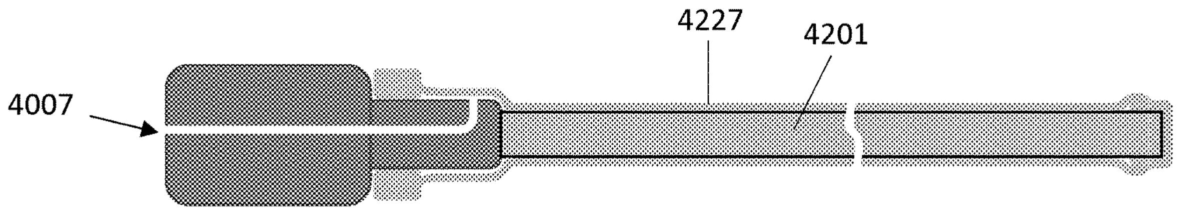
FIG. 42 schematically illustrates an example of an endoscope sheath device coupled (and sealed to) the endoscope after the application of negative pressure, showing the tubular external sheath vacuumed down against the outer surface of the endoscope.

FIG. 42 illustrates an example of an external sheath 4227 being vacuumed onto the endoscope 4201. The sheath is sealed onto the endoscope shaft due to an applied vacuum 4007 between the sheath and shaft. The application of negative pressure (vacuum) pulls the external sheath inwards, against the endoscope. Applying a vacuum (e.g., between the shaft and the sheath) shrink-fits the flexible sheath onto the endoscope flexible shaft. For a manual endoscope, this may improve the ability to manually grasp and control the shaft by preventing slippage between the external sheath and the shaft, both longitudinally and torsionally. The vacuum can be released to remove the sheath. Further, measuring for vacuum leaks can be used to determine if there is a leak in the sheath.

Figure 43A:
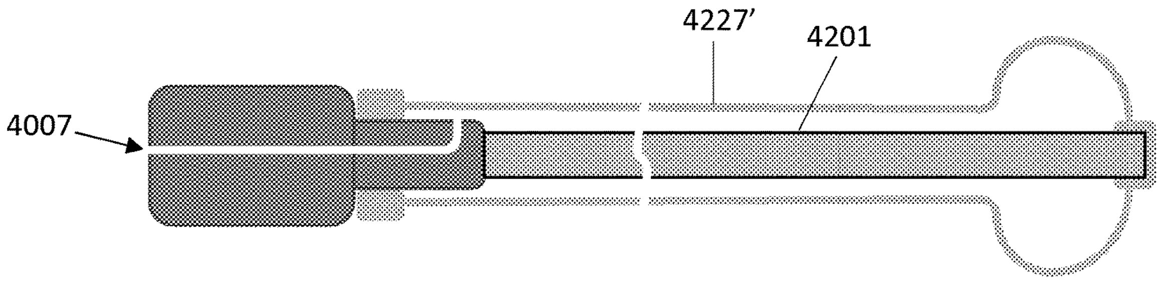
FIGS. 43A-43B are schematic illustrations of examples of endoscope sheath devices coupled (and sealed to) an endoscope in which positive pressure has been applied between the external sheath and the endoscope to inflate the tubular external sheath.
Figure 43B:
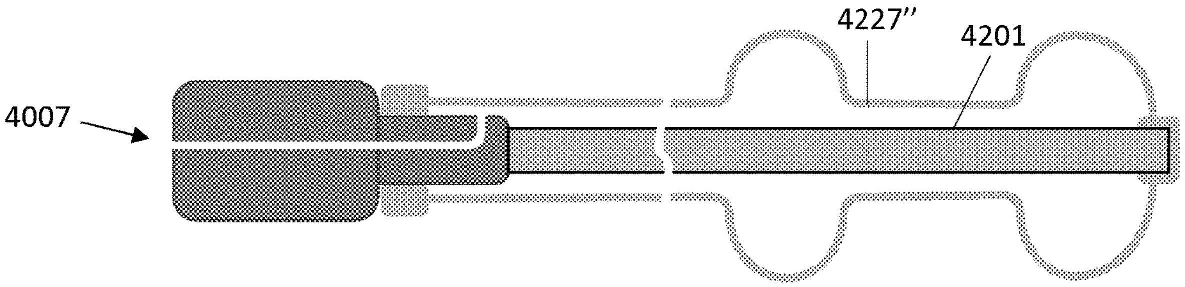

FIGS. 43A-43B illustrate the application of positive pressure. FIG. 43A shows an example of an endoscope sheath device having a single distal "balloon" shape when inflating the external sheath 4227'. FIG. 43B shows an example of an endoscope sheath device with multiple annular balloon shapes. In these examples, when positive pressure is applied the sheath 4227" can inflate similar to a balloon. Pressurized gas or fluid may be pumped into the space between the sheath 4227', 4227" and the endoscope shaft 4201. Various expanded balloon profiles can be utilized which can include, but are not limited to: single distal balloon shape, multiple annular ring balloon shapes, helical balloon shape, constant diameter etc. The expanded balloon can help stabilize and center the device in the anatomical lumen.

Figure 45:
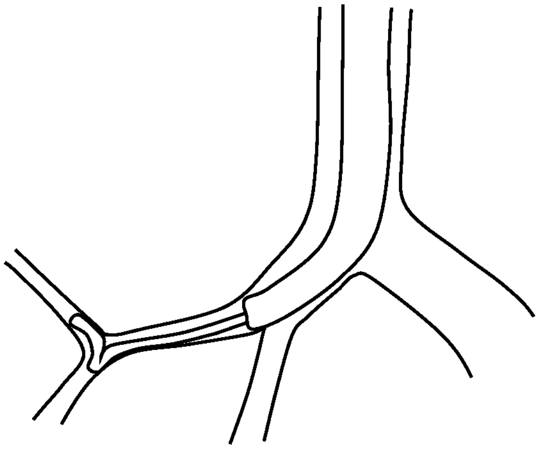
FIG. 45 illustrates the problem of buckling of an endoscope (e.g., catheter) when advancing within a tortious anatomy.

Also described herein are flexible devices (endoscopes, catheters) that can get deep into anatomy (e.g. the lungs periphery, the GI tract). However, when they are small and flexible enough to do, kinematic issues become apparent, including looping, prolapse, 'tram-tracking', and buckling. Although there are many strategies to overcome these issues, including by reducing clinical expectations, changing patient position, pushing on localized anatomy, and attempts to solve this by using steering, sheaths, and overtubes, in many instances (for example, in the lungs) the overtube may become too large such that it cannot progress forward. This sort of buckling, as depicted in the lungs, is shown in the FIG. 45, showing buckling of the endoscope while trying to get to the lung periphery. The use of a sheath, coupled with the use of positive pressure to inflate the sheath, may help to solve this problem. As shown in FIGS. 45A-46B, the apparatus may have an external sheath 4607 that goes over the device and overtube 4674. The accordion, zig zag region on the sheath indicates a stretcher material.

Figure 46A:
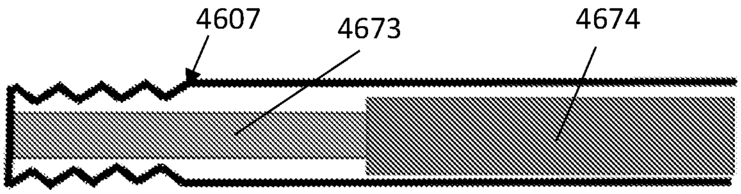
FIGS. 46A-46B illustrate the use of an endoscope sheath device to deploy (e.g., advance) an endoscope member as described herein.
Figure 46B:
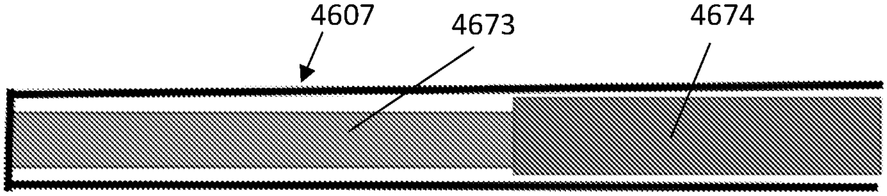

At the point where the overtube 4674 can no longer progress any farther without pulling the scope back, since the anatomy is too tight, the sheath may be pressurized (by the application of positive pressure) to the region between the sheath and the endoscope/overtube. Inflating the sheath potentially does two things: it stabilizes the outer diameter of the device through local anatomical contact, and it turns the device into a pneumatic or hydraulic cylinder, thereby facilitation forward movement of the tip through the application of the positive pressure. This may minimize the buckling risk of pushing a very flexible scope forward from the proximal end. This is shown in FIGS. 46A and 46B.

Figure 47:
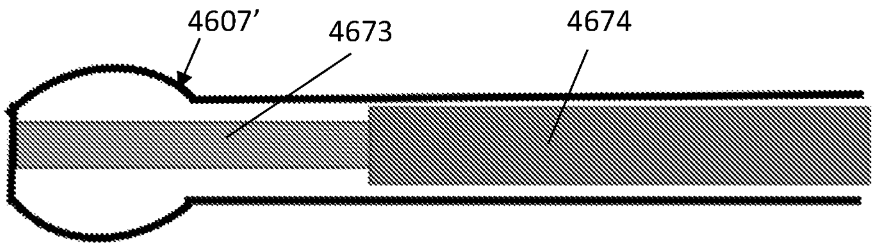
FIG. 47 illustrate another example of an endoscope sheath device including an inflatable sheath applied to a nested endoscope.
Figure 48:
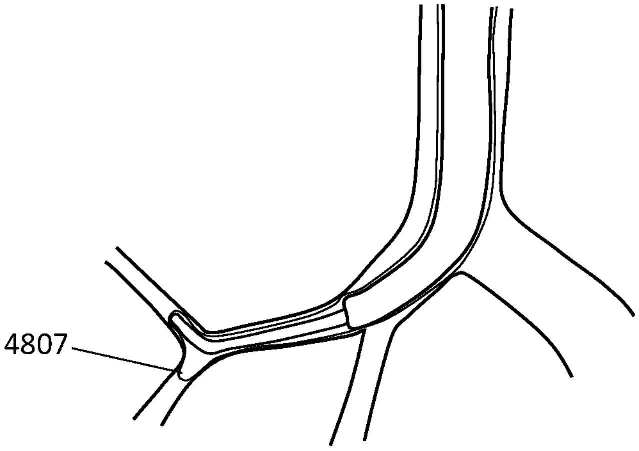
FIG. 48 is similar to FIG. 45 and illustrates the use of an inflatable endoscope sheath device to help guide the positioning of the endoscope within the tortuous anatomy.

The overtube 4674 (e.g., outer endoscope of a nested pair of scopes) may be moved forward in tight anatomy without dragging the device backwards by further inflating the sheath but hold the device stationary. This may cause the sheath 4607' to balloon out, and can be used as an anchor against anatomy and then the device becomes similar to a more stable guidewire that can guide the overtube forward without getting pulled back itself. This is shown in FIG. 47. Once the clinician has reached their anatomical target, they may choose to 'lock' the tip of the device in place, which may be similar to the technique of inflating a distal balloon. Alternatively, they could choose to inflate their sheath 4807 over a much longer length to get traction over more anatomy, as illustrated in FIG. 48. Positive pressure could be applied with a gas, or with a liquid (e.g., saline).

Figure 49:
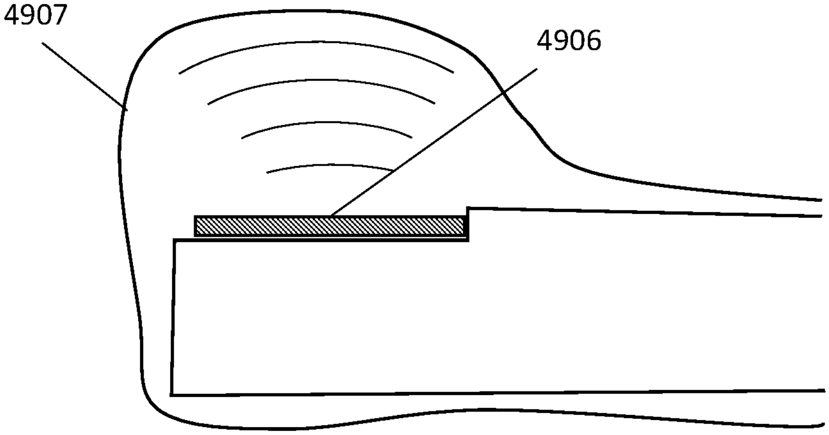
FIG. 49 schematically illustrates an example of an inflatable endoscope sheath used in which the endoscope includes a sensor (e.g., ultrasound sensor).

These apparatuses may be used with a side mounted ultrasound, as shown in FIG. 49. Thus, the saline-inflated external sheath may act as a saline-filled balloon when combined with ultrasound, which may help to localize targets that cannot be visually seen. FIG. 49 illustrates a side-mounted ultrasound device including an ultrasound transducer 4906 within an inflated external sheath 4907.

Installing Handle

Figure 50A:
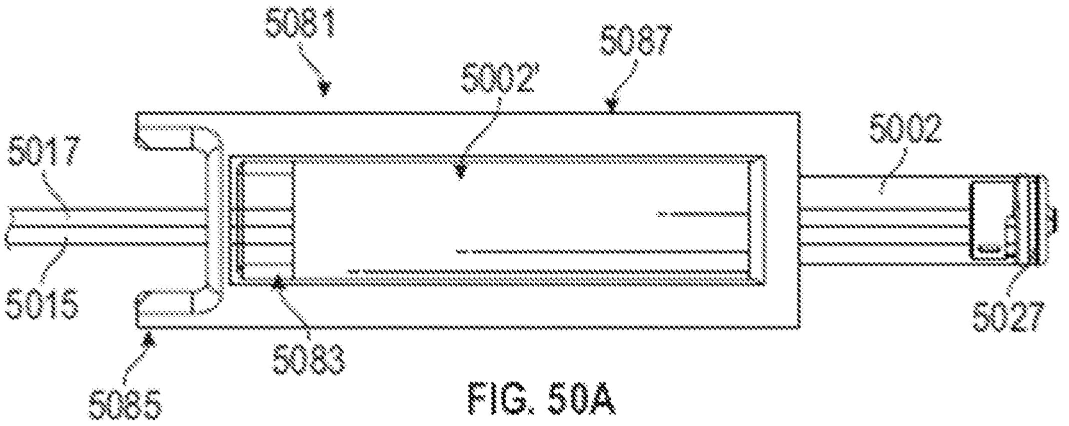
FIGS. 50A-50C illustrate one example of an endoscope sheath apparatus (e.g., endoscope sheath device) including an installing handle.

Any of the endoscope sheath apparatuses (e.g., endoscope sheath devices) described herein may include an installing handle for applying and/or removing the apparatus from an endoscope. For example, FIG. 50A shows an endoscope sheath apparatus including a cap 5027 that is configured to securely couple to an endoscope, an external sheath 5002, 5002', a pair of internal sheaths 5015, 5017 and an installing handle 5081.

Figure 50B:
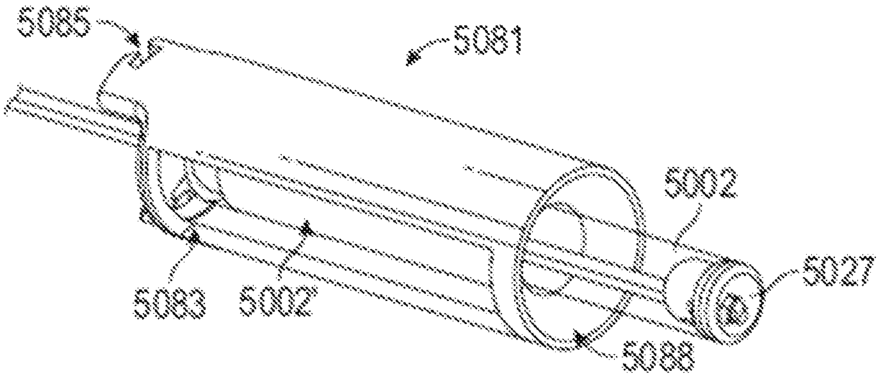
Figure 50C:
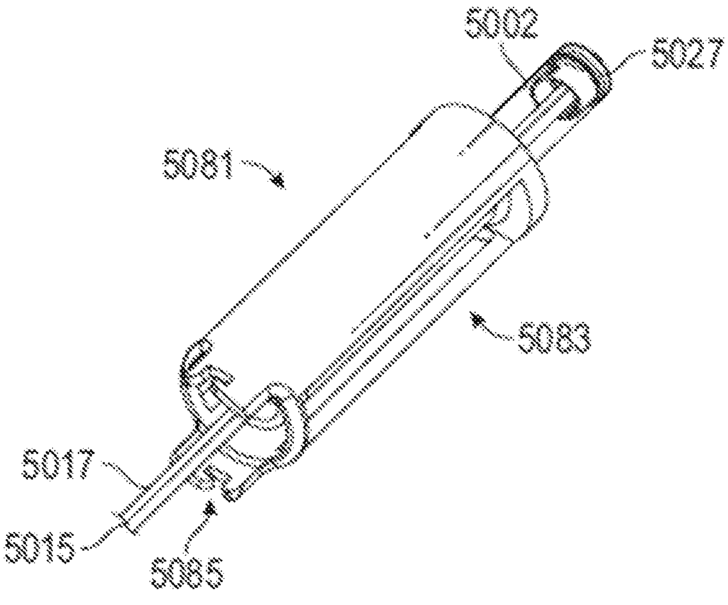

In general an installing handle is configured to hold or gather the flexible/compressible external sheath in a compact and easy to manipulate form, while permitting easy placement of the one or more inner sheath members. The installing handle may include a body, which in FIGS. 50A-50C is cylindrical, but any appropriate shape may be used, and an inner chamber into which the external sheath 5002' may be gathered. The external sheath may be gathered by pleating, folding (e.g., accordion folding, bellows folding, etc.), scrunching, etc. The external sheath may be gathered so that there remains a passage through the gathered external sheath that the endoscope may be inserted through as the inner sheath(s) 5015, 5017 are inserted into the lumen(s) of the endoscope as will be illustrated in FIGS. 51A-51D.

The installing handle 5081 may include an outer gripping region 5087, which may be configured to fit into a user's hand. The installing handle may also include a distal-facing conical surface (or distal funnel) 5088 that may be particularly useful when removing the external sheath, as described in FIGS. 54A-54C. Any of the installing handles described herein may be configured to couple or attach to the endoscope, such as to the proximal end of an endoscope. Thus, in some examples the installing handle may include a coupler at the distal end of the installing handle that is configured to couple to a matching attachment on the endoscope. In FIGS. 50A-50C the coupler 5085 is configured as a BNC-type coupler that may engage a pin on the endoscope, but any appropriate coupler (and complementary attachment on the endoscope) may be used.

In the installing handle 5081 example shown the installing handle includes a window or opening 5083 that may open into the internal chamber holding a portion of the external sheath 5002'.

Figures 51A, 51B, 51C, 51D:
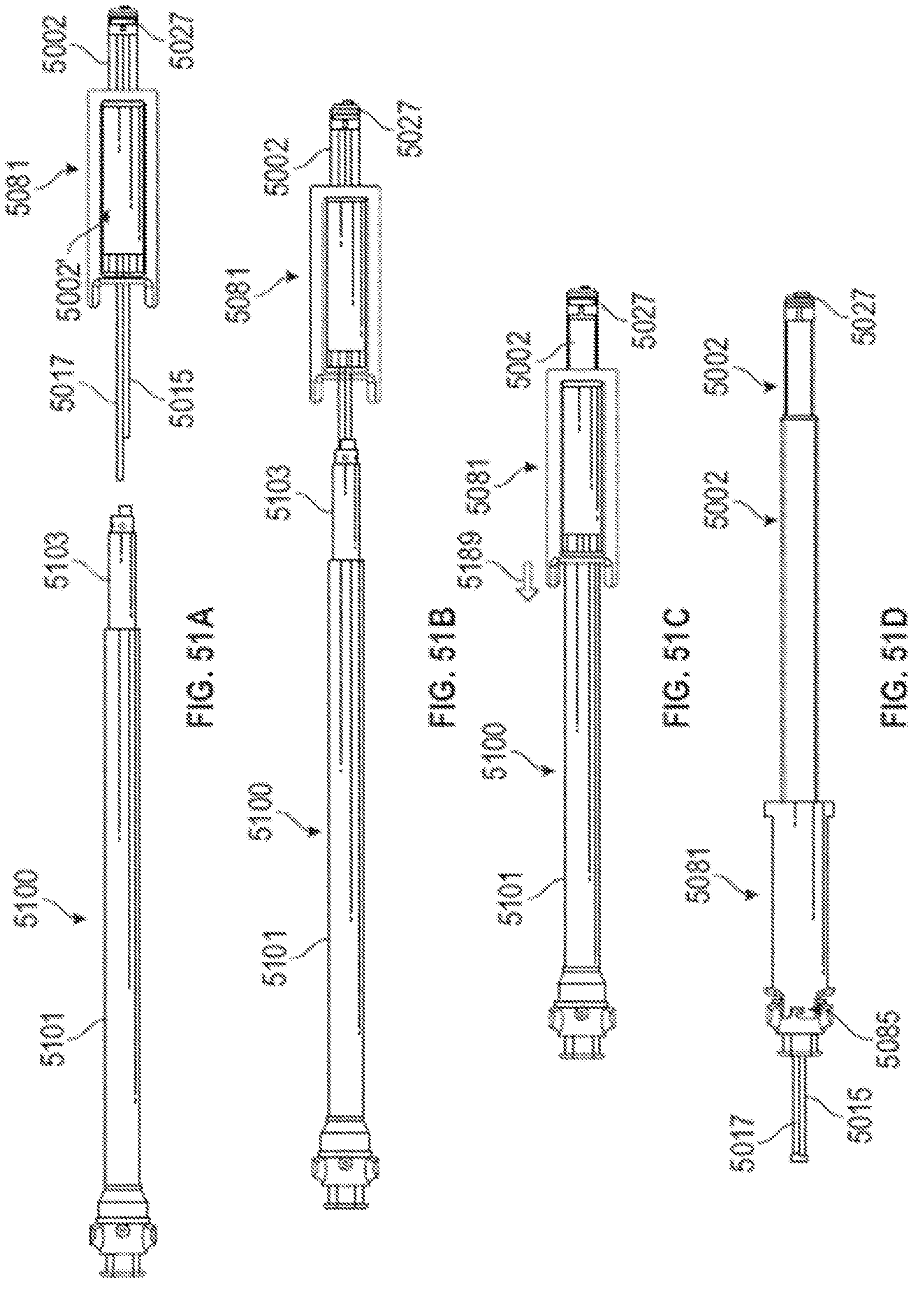
FIGS. 51A-51D illustrate one example of a method of applying an endoscope sheath apparatus over an endoscope as described herein, using an installing handle.

FIGS. 51A-51D illustrate the application of the endoscope sheath apparatus shown in FIGS. 50A-50C onto an endoscope assembly 5100. The endoscope assembly shown in this example include a nested pair of endoscopes including an inner endoscope 5103 that is nested within, and may be slidably coupled to, the outer endoscope 5201 (e.g., overtube). In this example the inner sheaths 5015, 5017 that extend proximally from the endoscope sheath apparatus are first inserted into a pair of lumens in the endoscope from the distal end of the endoscope, as illustrated in FIG. 51B. The distal end of the endoscope is inserted through the proximal end of the installing handle 5081, into the lumen of the tubular external sheath that is held gathered in the chamber of the installing handle, until, as shown in FIG. 51C, the distal end of the endoscope (e.g., inner endoscope 5103) is engaged with the cap 5027 of the endoscope sheath assembly. The user may then pull 5189 the installing handle 5081 proximally so that the external sheath 5002 is pulled over the endoscope, as shown in FIG. 51D. Drawing the installing handle proximally relative to the endoscope causes the external sheath to be dispensed distally out of the installing handle. In FIG. 51D the external sheath is shown matching the outer diameter of the different regions of the inner endoscope 5103 that is nested onto the outer endoscope 5101 (e.g., as it may when negative pressure is applied between the external sheath and the endoscope(s), as described above. In any of these apparatuses and methods the external sheath may have a uniform diameter that may accommodate the outer diameter of both the inner and outer endoscopes. The same apparatus and techniques illustrated here may be used with a single (e.g., non-nested) endoscope.

Figure 52A:
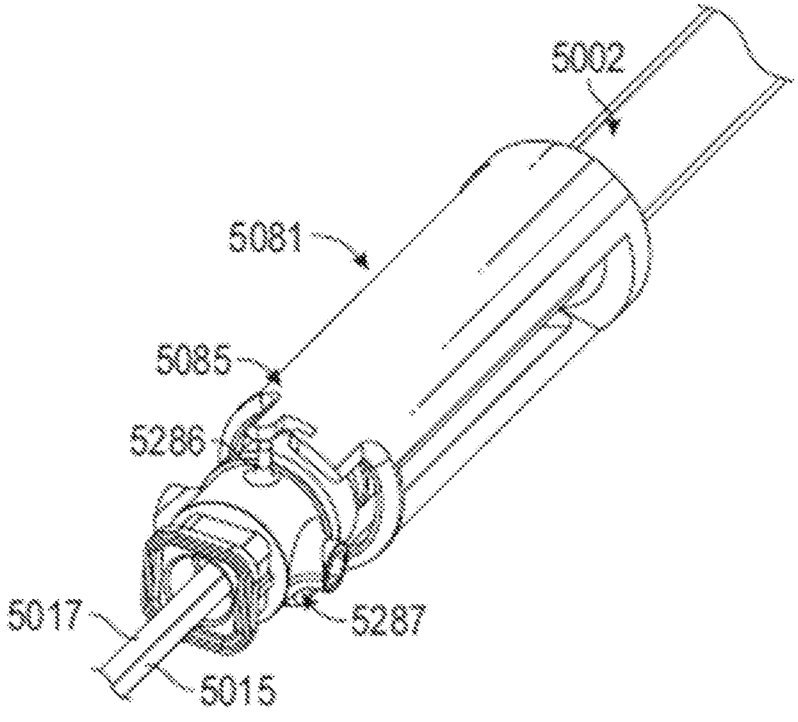
FIGS. 52A-52B show a back (proximal) view of an endoscope sheath apparatus including an installing handle, showing coupling of the installing handle to the proximal end of the endoscope.
Figure 52B:
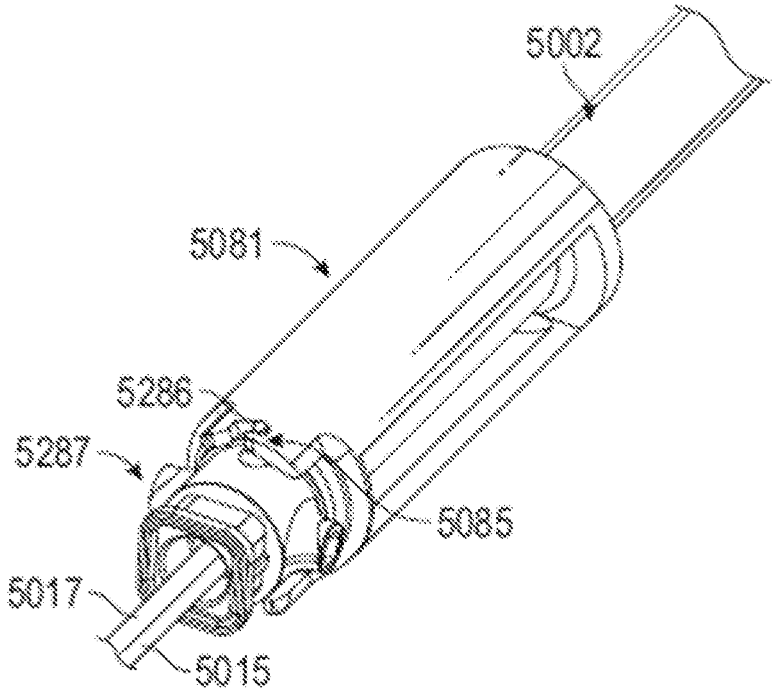

In FIG. 51D the installing handle 5081 may be coupled to the outer endoscope 5101 by engaging the coupler 5085 with a complementary attachment on the endoscope, as illustrated in greater detail in FIGS. 52A-52B. As shown in this example the proximal end of the outer endoscope 5287 includes an attachment 5286 (shown in this example a pin) that may be engaged with the coupler 5085 (shown in this example as a channel, e.g., having a BNC-type configuration) of the installing handle. FIG. 52B shows the installing handle engaged with the pin of the endoscope. Any appropriate coupler may be used (e.g., magnetic, mechanical, etc.).

Figure 53:
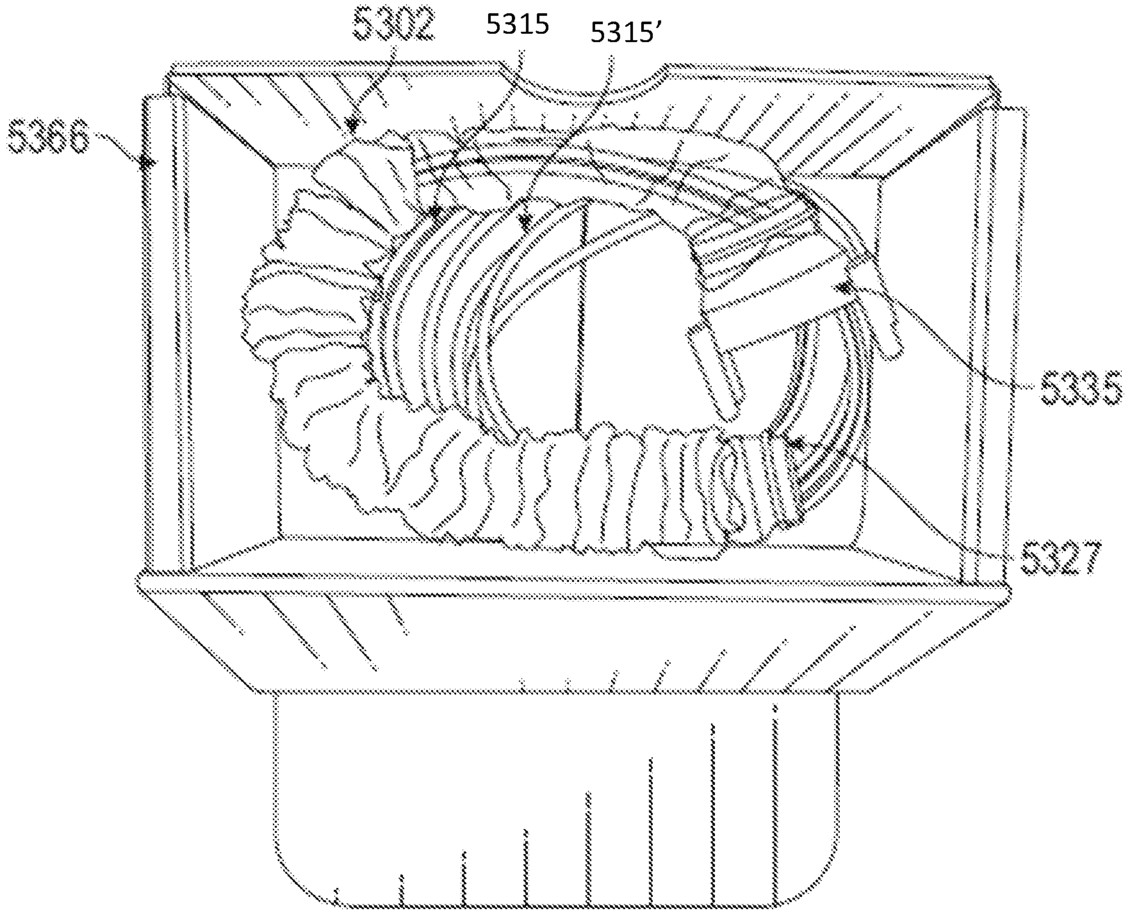
FIG. 53 illustrate an example of a method of packaging an endoscope sheath apparatus as described herein. Illustrating the compact, coiled configuration.

The endoscope sheath apparatuses described herein may generally be packaged in a primed state, ready for applying over an endoscopy or endoscope assembly. This may include packaging with the installing handle. The primed state may include inverting and/or compressing (e.g., pleating, folding, scrunching, etc.) the external sheath and/or loading it into the installing handle. For example FIG. 53 shows an examples of an endoscope sheath apparatus including an external sheath 5302 that is inverted and compressed (but without an installing handle in this example), a tip 5327, a proximal base 5335, and a pair of inner sheaths 5315, 5317. The endoscope sheath apparatus is shown coiled and positioned within a packaging (e.g., box 5366).

Figure 54A:
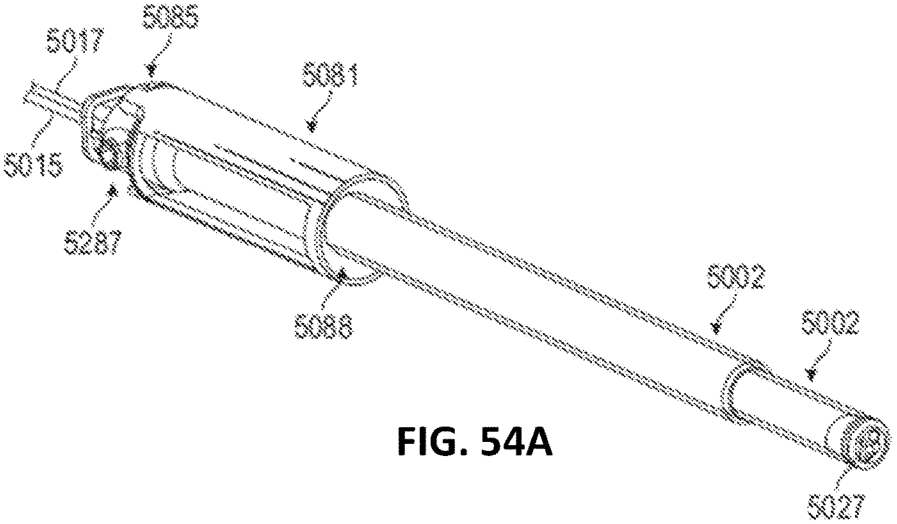
FIGS. 54A-54C illustrate removal of an endoscope sheath apparatus from an endoscope using an installing handle.
Figure 54B:
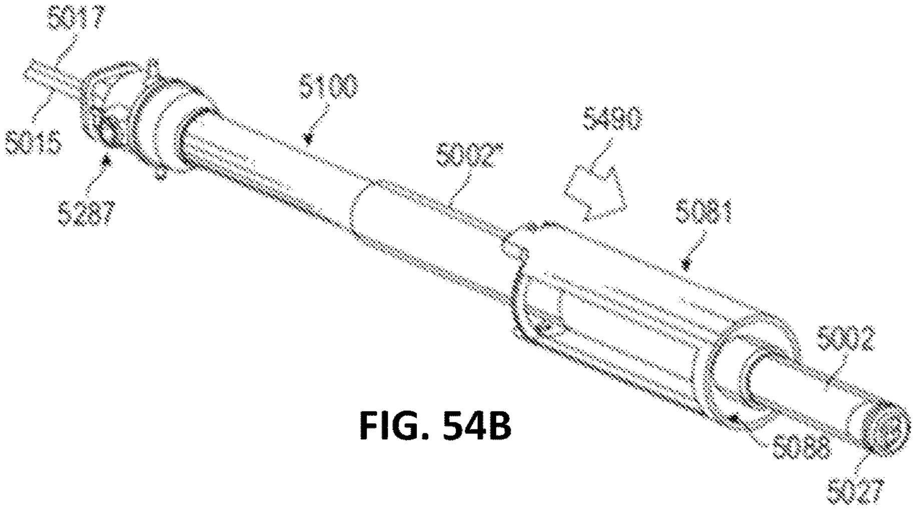
Figure 54C:
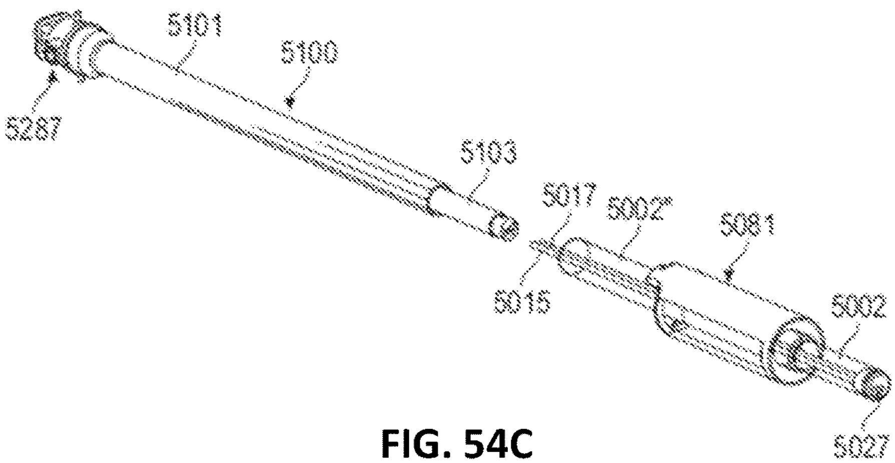

As mentioned above, the installing handles described herein may also be useful for removing the endoscope sheath apparatus form the endoscope(s). For example, FIGS. 54A-54C illustrate removal of the apparatus from the endoscope assemblies shown in FIGS. 51A-51D. The installing handle 5081 may first be disengaged from the endoscope proximal end region 5287, and then driven 5490 (by pushing, pulling, etc.) distally as shown in FIG. 54B. as the installing handle moves distally, the external sheath is pulled over itself and inverts so that any contamination is held between the folded-over (inverted) portions of the external sheath 5002" so that only the inner (uncontaminated) portion is exposed proximally. The distal funnel-shape 5088 on the installing handle may help collect any contaminant material and invert the external sheath 5002.

As mentioned above, the inner sheaths 5015, 5017 may be sealed at their proximal end (e.g., by crimping, heating, etc.) preventing contamination before the cap is disengaged and they are withdrawn distally, as shown in FIG. 54C. Thereafter, the endoscope sheath assembly may be disposed of. Prior to removing the endoscope sheath assembly the assembly may be pressurized to confirm that no leaks have developed that may otherwise indicate contamination of the endoscope(s) was likely to have occurred.

Method of Making

Figure 55:
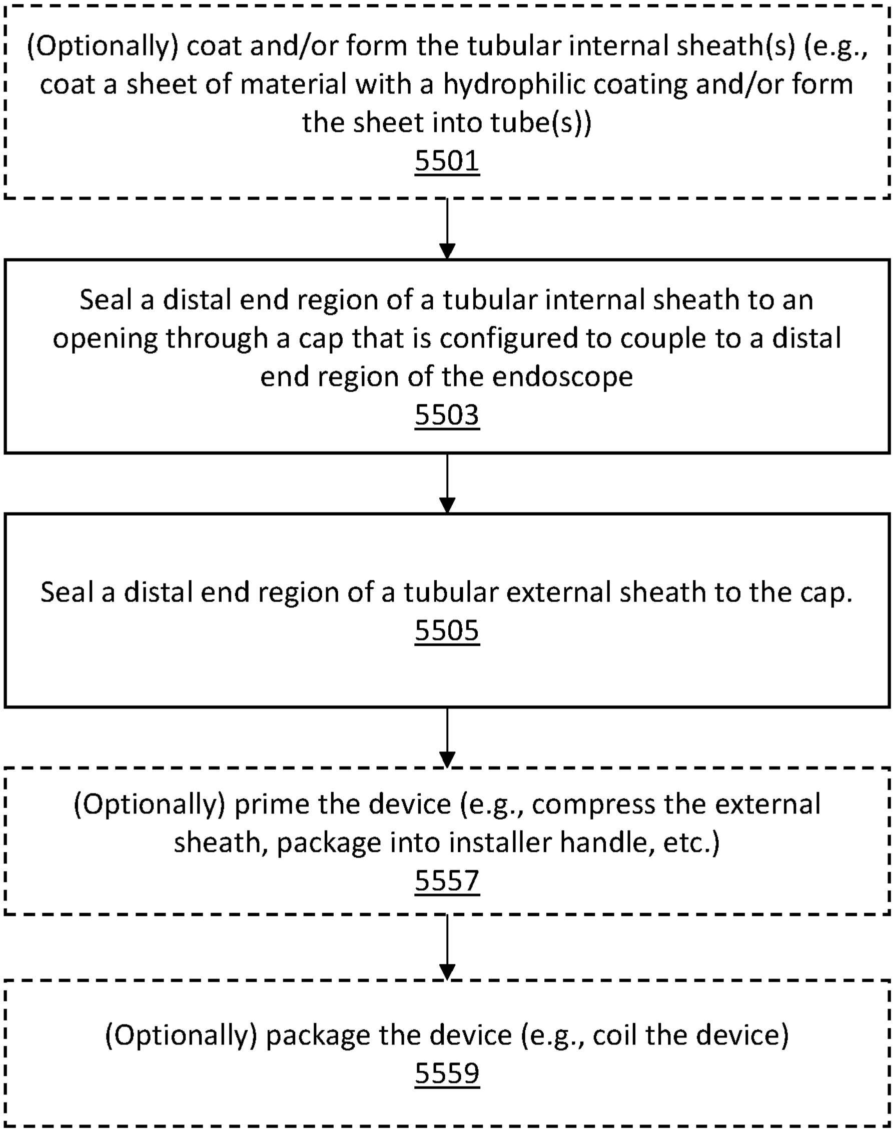
FIG. 55 schematically illustrates one method of making an endoscope sheath apparatus as described herein.

Also described herein are methods of making any of these apparatuses. For example, a method of making an endoscope sheath device that is configured to prevent contamination of an endoscope is schematically illustrated in FIG. 55. In general these methods may include sealing a distal end region of a tubular internal sheath to an opening through a cap that is configured to couple to a distal end region of the endoscope 5503. Sealing may be performed by any appropriate technique, including adhesive bonding, laser bonding (welding), etc. The tubular inner sheath(s) may be sealed by inserted into a hole through the cap and secured with the outer surface of the internal sheath bonded to the inner diameter of the hole. The tubular internal sheath may be configured to be inserted through a lumen of the endoscope. Thereafter the distal end region of a tubular external sheath may be sealed to the cap, including sealing around an outer perimeter of the cap 5505. The tubular external sheath may be configured to fit over an outer surface of the endoscope. The tubular external sheath may be sealed to the cap by an adhesive and/or a weld, or the like. In some example a gasket or ring (e.g. elastomeric material) may be used to seal and secure the tubular external sheath to the cap.

In some cases the parts may be formed and/or assembled first. For example, as shown in FIG. 55, an optional step may include coating the device, e.g., the inner sheath(s) and/or the cap and/or the external sheath with a material, such as a hydrophilic coating. In particular the internal tubular members may be coated with a hydrophilic coating by first coating a flat layer (e.g., sheet) of material, then forming the tubular inner sheath 5501. In some examples the cap may be formed as well. Optionally in some examples the internal sheath may be reinforced along a portion (e.g. distal end) or all of it length to prevented collapse when bending.

Optionally, the assembly including the cap, tubular external sheath and tubular internal sheath(s) may be primed or prepared by loading into an installing handle, as described above 5557. For example, the tubular external sheath may be compressed (e.g., scrunched, folded, etc.) into a chamber of the installing handle with the internal sheath(s) extending proximally from the cap through the installing handle and the external sheath. The assembly (with or without the installing handle) may be sterilized. Finally, the endoscope sheath apparatus assembly may be packaged 5559. In some example the endoscope sheath apparatus may be packaged in a compact, coiled configuration.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An endoscope sheath device configured to prevent contamination of an endoscope, the endoscope sheath device comprising:

an external sheath that is configured to be transitioned between a flexible configuration and a rigid configuration, the external sheath having a lumen;

a cap sealingly coupled to a distal end of the external sheath, the cap comprising an engagement region configured to secure the cap to a distal end of the endoscope, wherein the engagement region is configured to mate with the distal end of the endoscope when compressed from an oval resting cross-sectional configuration into a substantially circular mating cross-sectional configuration; and one or more internal sheaths each comprising an elongate flexible body extending within the lumen of the external sheath, wherein each of the one or more internal sheaths has one or more internal lumens and is configured to pass through a lumen of the endoscope to form a fluid-impermeable internal contamination barrier, further wherein each of the one or more internal sheaths is sealingly coupled to the cap so that the one or more internal lumens is open through the cap.

2. The endoscope sheath device of claim 1, wherein the external sheath is shorter than the one or more internal sheaths.

3. The endoscope sheath device of claim 1, wherein the cap is at least partially transparent.

4. The endoscope sheath device of claim 1, wherein the cap comprises a transparent region configured to align with a camera of the endoscope.

5. The endoscope sheath device of claim 1, wherein the engagement region is configured to secure to the cap to the distal end of the endoscope comprises one or more of: a friction fitting configured to secure the cap to the distal end of the endoscope, a snap fit configured to secure the cap to the distal end of the endoscope, a magnet configured to secure the cap to the distal end of the endoscope, a bayonet connector configured to secure the cap to the distal end of the endoscope, or a threaded region configured to secure the cap to the distal end of the endoscope.

6. The endoscope sheath device of claim 1, wherein at least one of the one or more internal sheaths comprises a multi-lumen catheter.

7. The endoscope sheath device of claim 1, wherein at least one of the one or more internal sheaths comprises a working channel liner having a working channel lumen.

8. The endoscope sheath device of claim 1, further comprising a proximal attachment on the external sheath configured to seal the external sheath to an outer surface of the endoscope.

9. The endoscope sheath device of claim 8, wherein the proximal attachment comprises an elastic attachment.

10. The endoscope sheath device of claim 1, wherein the external sheath is flexible and is configured to form an external fluid-impermeable contamination barrier.

11. The endoscope sheath device of claim 1, wherein the one or more internal sheaths comprises a working channel liner configured to form an internal fluid- impermeable contamination barrier within a working channel of the endoscope.

12. The endoscope sheath device of claim 1, further comprising a sealing region at a proximal end region of the internal sheath that is configured to be heat sealed to close off the one or more internal lumens after use to prevent contamination during removal of the one or more internal sheaths from within the lumen of the endoscope.

13. The endoscope sheath device of claim 12, wherein the sealing region is configured to be heat sealed and/or pressure sealed.

14. The endoscope sheath device of claim 1, wherein an internal lumen of the one or more internal sheaths comprises a hydrophilic coating.

15. An endoscope sheath device configured to prevent contamination of an endoscope, the endoscope sheath device comprising:

a tubular external sheath having a lumen, the tubular external sheath configured to form a fluid-impermeable external contamination barrier when the endoscope is within the lumen of the tubular external sheath, wherein the tubular external sheath is configured to be transitioned between a flexible configuration and a rigid configuration by an application or release of pressure;

a cap sealingly coupled to a distal end of the tubular external sheath, wherein the cap comprises an engagement region that is configured to secure to a distal end of the endoscope, wherein the engagement region is configured to mate with the distal end of the endoscope when compressed from an oval resting cross-sectional configuration into a substantially circular mating cross-sectional configuration; and one or more internal sheaths each comprising an elongate flexible body having one or more internal lumens, each of the one or more internal sheaths extending within the lumen of the tubular external sheath, wherein each of the one or more internal sheaths are configured to pass through a lumen of the endoscope to form a fluid-impermeable internal contamination barrier, wherein each of the one or more internal sheaths is sealingly coupled to the cap so that the one or more internal lumens are open through the cap.

16. An endoscope sheath device configured to prevent contamination of an endoscope, the endoscope sheath device comprising:

a tubular external sheath configured to fit over the endoscope, wherein the tubular external sheath has a lumen and is configured to be transitioned between a flexible configuration and a rigid configuration by an application or release of pressure;

a cap sealingly coupled to a distal end of the tubular external sheath, the cap comprising an engagement region configured to secure the cap to a distal end of the endoscope, wherein the engagement region is configured to mate with the distal end of the endoscope when compressed from an oval resting cross-sectional configuration into a substantially circular mating cross-sectional configuration;

one or more internal sheaths each comprising an elongate flexible body extending within the lumen of the tubular external sheath and configured to fit within a lumen extending through the endoscope, wherein each of the one or more internal sheaths has one or more internal lumens, further wherein each of the one or more internal sheaths is sealingly coupled to the cap so that the one or more internal lumens is open through the cap; and a sealing region at a proximal end of the one or more internal sheaths that is configured to be sealed after use to prevent contamination during removal of the one or more internal sheaths from within the lumen extending through the endoscope.

17. The endoscope sheath device of claim 16, wherein the sealing region comprises a crimping region.

18. The endoscope sheath device of claim 16, wherein the sealing region is configured to be heat sealed.

19. The endoscope sheath device of claim 16, wherein the sealing region is configured to be pressure sealed.

20. The endoscope sheath device of claim 16, wherein the tubular external sheath is shorter than the one or more internal sheaths.

21. The endoscope sheath device of claim 16, wherein the cap is at least partially transparent.

22. The endoscope sheath device of claim 16, wherein the cap comprises a transparent region configured to align with a camera of the endoscope.

23. The endoscope sheath device of claim 16, wherein the engagement region configured to secure the cap to the distal end of the endoscope comprises: a friction fitting configured to secure the cap to the distal end of the endoscope, a snap fit configured to secure the cap to the distal end of the endoscope, a magnet configured to secure the cap to the distal end of the endoscope, a bayonet connector configured to secure the cap to the distal end of the endoscope, or a threaded region configured to secure the cap to the distal end of the endoscope.

24. An endoscope sheath device configured to prevent contamination of an endoscope, the endoscope sheath device comprising:

an external sheath having a lumen therethrough that is configured to be transitioned between a flexible configuration and a rigid configuration;

a cap sealingly coupled to a distal end of the external sheath, the cap comprising an engagement region configured to secure the cap to a distal end of the endoscope, wherein the engagement region is configured to mate with the distal end of the endoscope when compressed from an oval resting cross-sectional configuration into a substantially circular mating cross-sectional configuration; and an internal sheath comprising a catheter extending within the lumen of the external sheath, wherein the internal sheath is sealingly coupled to the cap so that a lumen of the catheter is open through the cap, further wherein the internal sheath is configured to extend through a lumen of the endoscope; and a sealing region at a proximal end region of the internal sheath that is configured to heat sealed to close off the lumen of the catheter after use to prevent contamination during removal of the internal sheath from within the lumen of the endoscope.

* * * * *